(12) United States Patent
Bjorsell

(10) Patent No.: US 12,395,425 B2
(45) Date of Patent: *Aug. 19, 2025

(54) DETERMINING A TIME TO PERMIT A COMMUNICATIONS SESSION TO BE CONDUCTED

(71) Applicant: VoIP-Pal.com, Inc., Bellevue, WA (US)

(72) Inventor: Johan Emil Viktor Bjorsell, Vancouver (CA)

(73) Assignee: VoIP-Pal.com, Inc. (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/521,836

(22) Filed: Nov. 8, 2021

(65) Prior Publication Data

US 2022/0070088 A1 Mar. 3, 2022

Related U.S. Application Data

(63) Continuation of application No. 14/853,705, filed on Sep. 14, 2015, now Pat. No. 11,171,864, which is a
(Continued)

(51) Int. Cl.
*H04L 12/725* (2013.01)
*A61K 39/395* (2006.01)
(Continued)

(52) U.S. Cl.
CPC .... *H04L 45/3065* (2013.01); *A61K 39/39558* (2013.01); *A61K 45/06* (2013.01);
(Continued)

(58) Field of Classification Search
None
See application file for complete search history.

(56) References Cited

U.S. PATENT DOCUMENTS

| 3,725,596 A | 4/1973 | Maxon et al. |
| 4,661,974 A | 4/1987 | Bales et al. |

(Continued)

FOREIGN PATENT DOCUMENTS

| BR | PI 0718312-7 A2 | 11/2013 |
| BR | PI 0719682-2 A2 | 1/2014 |

(Continued)

OTHER PUBLICATIONS

Canadian Office Action dated Oct. 24, 2018 for Canadian Patent Application No. CA 2,670,510.
(Continued)

*Primary Examiner* — Kouroush Mohebbi
(74) *Attorney, Agent, or Firm* — Thorpe North & Western, LLP.

(57) ABSTRACT

A method, apparatus and system for routing a communication in a communication system between a first participant device, on an Internet Protocol (IP) network, associated with a first participant, and a second participant device associated with a second participant. The method comprises receiving a second participant identifier associated with the second participant device, causing the at least one processor to access a user profile that is specific to the first participant and associated with a plurality of first participant attributes, comparing the second participant and at least one first participant attribute and identifying whether at least one route exists, producing route information to an Internet Protocol (IP) address on a first communication network or associated with a gateway to the second communication network, and establishing the communication to the second participant. At least one of the networks may utilize Public Switched Telephone Network (PSTN) compatible numbers for identifying a route for the communication.

40 Claims, 32 Drawing Sheets

Related U.S. Application Data continuation of application No. 14/029,671, filed on Sep. 17, 2013, now Pat. No. 9,137,385, which is a continuation of application No. 12/513,147, filed as application No. PCT/CA2007/001956 on Nov. 1, 2007, now Pat. No. 8,542,815.

(60) Provisional application No. 60/856,212, filed on Nov. 2, 2006.

(51) Int. Cl.

| | | |
|---|---|---|
| *A61K 45/06* | (2006.01) | |
| *C07K 16/18* | (2006.01) | |
| *H04L 9/32* | (2006.01) | |
| *H04L 12/14* | (2006.01) | |
| *H04L 12/66* | (2006.01) | |
| *H04L 45/302* | (2022.01) | |
| *H04L 61/5007* | (2022.01) | |
| *H04L 65/1033* | (2022.01) | |
| *H04L 65/1069* | (2022.01) | |
| *H04M 3/42* | (2006.01) | |
| *H04M 7/00* | (2006.01) | |
| *H04M 15/00* | (2006.01) | |
| *H04M 15/02* | (2006.01) | |
| *H04Q 3/66* | (2006.01) | |
| *H04Q 3/70* | (2006.01) | |

(52) U.S. Cl.
CPC ............ *C07K 16/18* (2013.01); *H04L 9/3226* (2013.01); *H04L 12/14* (2013.01); *H04L 12/1439* (2013.01); *H04L 12/1496* (2013.01); *H04L 12/66* (2013.01); *H04L 61/5007* (2022.05); *H04L 65/1033* (2013.01); *H04L 65/1069* (2013.01); *H04M 3/4211* (2013.01); *H04M 7/006* (2013.01); *H04M 7/0075* (2013.01); *H04M 15/51* (2013.01); *H04M 15/56* (2013.01); *H04M 15/8083* (2013.01); *H04M 15/8228* (2013.01); *H04M 15/887* (2013.01); *H04M 15/888* (2013.01); *H04Q 3/66* (2013.01); *H04Q 3/70* (2013.01); *H04Q 2213/13091* (2013.01); *H04Q 2213/13141* (2013.01); *H04Q 2213/13196* (2013.01); *H04Q 2213/1322* (2013.01); *H04Q 2213/13384* (2013.01)

(56) References Cited

U.S. PATENT DOCUMENTS

| | | |
|---|---|---|
| 4,747,124 A | 5/1988 | Ladd |
| 4,799,255 A | 1/1989 | Billinger et al. |
| 4,916,491 A | 4/1990 | Katoh |
| 4,992,971 A | 2/1991 | Hayashi |
| 5,146,491 A | 9/1992 | Silver et al. |
| 5,247,571 A | 9/1993 | Kay et al. |
| 5,303,297 A | 4/1994 | Hillis |
| 5,325,421 A | 6/1994 | Hou et al. |
| 5,359,642 A | 10/1994 | Castro |
| 5,425,085 A | 6/1995 | Weinberger et al. |
| 5,440,621 A | 8/1995 | Castro |
| 5,454,030 A | 9/1995 | de Oliveira et al. |
| 5,469,497 A | 11/1995 | Pierce et al. |
| 5,506,893 A | 4/1996 | Buscher et al. |
| 5,511,114 A | 4/1996 | Stimson et al. |
| 5,519,769 A | 5/1996 | Weinberger et al. |
| 5,559,871 A | 9/1996 | Smith |
| 5,561,707 A | 10/1996 | Katz |
| 5,572,583 A | 11/1996 | Wheeler, Jr. et al. |
| 5,590,133 A | 12/1996 | Billstrom et al. |
| 5,602,907 A | 2/1997 | Hata et al. |
| 5,608,786 A | 3/1997 | Gordon |
| 5,621,787 A | 4/1997 | McKoy et al. |
| 5,633,913 A | 5/1997 | Talarmo |
| 5,661,790 A | 8/1997 | Hsu |
| 5,677,955 A | 10/1997 | Doggett et al. |
| 5,712,907 A | 1/1998 | Wegner et al. |
| 5,719,926 A | 2/1998 | Hill |
| 5,722,067 A | 2/1998 | Fougnies et al. |
| 5,724,355 A | 3/1998 | Bruno et al. |
| 5,726,984 A | 3/1998 | Kubler et al. |
| 5,737,414 A | 4/1998 | Walker et al. |
| 5,742,596 A | 4/1998 | Baratz et al. |
| 5,751,961 A | 5/1998 | Smyk |
| 5,768,521 A | 6/1998 | Dedrick |
| 5,778,187 A | 7/1998 | Monteiro et al. |
| 5,793,762 A | 8/1998 | Penners et al. |
| 5,799,072 A | 8/1998 | Vulcan et al. |
| 5,802,502 A | 9/1998 | Gell et al. |
| 5,825,863 A | 10/1998 | Walker |
| 5,828,740 A | 10/1998 | Khuc et al. |
| 5,838,682 A | 11/1998 | Dekelbaum et al. |
| 5,845,267 A | 12/1998 | Ronen |
| 5,850,433 A | 12/1998 | Rondeau |
| 5,864,610 A | 1/1999 | Ronen |
| 5,867,495 A | 2/1999 | Elliott et al. |
| 5,875,240 A | 2/1999 | Silverman |
| 5,881,139 A | 3/1999 | Romines |
| 5,883,810 A | 3/1999 | Franklin et al. |
| 5,883,891 A | 3/1999 | Williams et al. |
| 5,889,774 A | 3/1999 | Mirashrafi et al. |
| 5,905,736 A | 5/1999 | Ronen et al. |
| 5,907,547 A | 5/1999 | Foladare et al. |
| 5,910,946 A | 6/1999 | Csapo |
| 5,915,005 A | 6/1999 | He |
| 5,915,093 A | 6/1999 | Berlin et al. |
| 5,917,899 A | 6/1999 | Moss et al. |
| 5,923,659 A | 7/1999 | Curry et al. |
| 5,923,745 A | 7/1999 | Hurd |
| 5,930,343 A | 7/1999 | Vasquez |
| 5,937,045 A | 8/1999 | Yaoya et al. |
| 5,937,053 A | 8/1999 | Lee et al. |
| 5,940,598 A | 8/1999 | Strauss et al. |
| 5,953,504 A | 9/1999 | Sokal et al. |
| 5,956,391 A | 9/1999 | Melen et al. |
| 5,970,477 A | 10/1999 | Roden |
| 5,974,043 A | 10/1999 | Solomon |
| 5,991,291 A | 11/1999 | Asai et al. |
| 5,991,378 A | 11/1999 | Apel |
| 6,005,870 A | 12/1999 | Leung et al. |
| 6,005,926 A | 12/1999 | Mashinsky |
| 6,014,379 A | 1/2000 | White et al. |
| 6,021,126 A | 2/2000 | White et al. |
| 6,029,062 A | 2/2000 | Hanson |
| 6,036,090 A | 3/2000 | Rahman et al. |
| 6,044,263 A | 3/2000 | Valentine et al. |
| 6,052,445 A | 4/2000 | Bashoura et al. |
| 6,058,300 A | 5/2000 | Hanson |
| 6,069,890 A | 5/2000 | White et al. |
| 6,073,013 A | 6/2000 | Agre et al. |
| 6,073,142 A | 6/2000 | Geiger et al. |
| 6,078,647 A | 6/2000 | D'Eletto |
| 6,104,704 A | 8/2000 | Buhler et al. |
| 6,104,711 A | 8/2000 | Voit |
| 6,108,704 A | 8/2000 | Hutton et al. |
| 6,115,737 A | 9/2000 | Ely et al. |
| 6,122,357 A | 9/2000 | Farris et al. |
| 6,128,304 A | 10/2000 | Gardell et al. |
| 6,137,869 A | 10/2000 | Voit et al. |
| 6,141,404 A | 10/2000 | Westerlage et al. |
| 6,151,385 A | 11/2000 | Reich et al. |
| 6,173,272 B1 | 1/2001 | Thomas et al. |
| 6,185,414 B1 | 2/2001 | Brunner et al. |
| 6,185,565 B1 | 2/2001 | Meubus et al. |
| 6,188,752 B1 | 2/2001 | Lesley |
| 6,192,044 B1 | 2/2001 | Mack |
| 6,192,123 B1 | 2/2001 | Grunsted et al. |
| 6,205,135 B1 | 3/2001 | Chinni et al. |
| 6,236,851 B1 | 5/2001 | Fougnies et al. |
| 6,240,449 B1 | 5/2001 | Nadeau |
| 6,243,689 B1 | 6/2001 | Norton |

(56) References Cited

U.S. PATENT DOCUMENTS

| | | |
|---|---|---|
| 6,249,573 B1 | 6/2001 | Hudson |
| 6,282,574 B1 | 8/2001 | Voit |
| 6,289,010 B1 | 9/2001 | Voit et al. |
| 6,292,547 B1 | 9/2001 | Katz |
| 6,292,553 B1 | 9/2001 | Fellingham et al. |
| 6,298,062 B1 | 10/2001 | Gardell et al. |
| 6,298,250 B1 | 10/2001 | Nilsson |
| 6,310,859 B1 | 10/2001 | Morita et al. |
| 6,320,947 B1 | 11/2001 | Joyce et al. |
| 6,324,280 B2 | 11/2001 | Dunn et al. |
| 6,327,351 B1 | 12/2001 | Walker et al. |
| 6,351,464 B1 | 2/2002 | Galvin et al. |
| 6,359,880 B1 | 3/2002 | Curry et al. |
| 6,363,065 B1 | 3/2002 | Thornton et al. |
| 6,430,275 B1 | 8/2002 | Voit et al. |
| 6,434,143 B1* | 8/2002 | Donovan ............ H04L 65/103 379/900 |
| 6,445,694 B1 | 9/2002 | Swartz |
| 6,449,353 B1 | 9/2002 | Hyndes, Jr. |
| 6,460,050 B1 | 10/2002 | Pace et al. |
| 6,480,885 B1 | 11/2002 | Olivier |
| 6,498,791 B2 | 12/2002 | Pickett et al. |
| 6,507,644 B1 | 1/2003 | Henderson et al. |
| 6,553,025 B1 | 4/2003 | Kung et al. |
| 6,560,224 B1 | 5/2003 | Kung et al. |
| 6,574,328 B1 | 6/2003 | Wood et al. |
| 6,594,254 B1 | 7/2003 | Kelly |
| 6,597,686 B1 | 7/2003 | Smyk |
| 6,597,783 B1 | 7/2003 | Tada et al. |
| 6,603,977 B1 | 8/2003 | Walsh et al. |
| 6,608,831 B1 | 8/2003 | Beckstrom et al. |
| 6,636,833 B1 | 10/2003 | Flitcroft et al. |
| 6,650,641 B1 | 11/2003 | Albert et al. |
| 6,665,293 B2 | 12/2003 | Thornton et al. |
| 6,674,745 B1 | 1/2004 | Schuster et al. |
| 6,674,850 B2 | 1/2004 | Vu et al. |
| 6,707,901 B1 | 3/2004 | Hodges et al. |
| 6,714,793 B1 | 3/2004 | Carey et al. |
| 6,718,032 B1 | 4/2004 | Vrenjak |
| 6,724,860 B2 | 4/2004 | Stumer et al. |
| 6,731,630 B1 | 5/2004 | Schuster et al. |
| 6,744,858 B1 | 6/2004 | Ryan et al. |
| 6,754,181 B1 | 6/2004 | Elliott et al. |
| 6,760,324 B1* | 7/2004 | Scott ............ H04M 7/1225 370/352 |
| 6,766,159 B2 | 7/2004 | Lindholm |
| 6,772,188 B1 | 8/2004 | Cloutier |
| 6,772,210 B1 | 8/2004 | Edholm |
| 6,775,269 B1 | 8/2004 | Kaczmarczyk et al. |
| 6,775,534 B2 | 8/2004 | Lindgren et al. |
| 6,785,266 B2 | 8/2004 | Swartz |
| 6,798,767 B1* | 9/2004 | Alexander ............ H04L 12/66 455/445 |
| 6,804,346 B1 | 10/2004 | Mewhinney |
| 6,819,929 B2 | 11/2004 | Antonucci et al. |
| 6,829,232 B1 | 12/2004 | Takeda et al. |
| 6,850,762 B1 | 2/2005 | Ala-Luukko et al. |
| 6,870,827 B1 | 3/2005 | Voit et al. |
| 6,873,599 B1 | 3/2005 | Han |
| 6,892,184 B1 | 5/2005 | Komen et al. |
| 6,928,070 B2 | 8/2005 | Emerson, III |
| 6,928,479 B1 | 8/2005 | Meyer et al. |
| 6,934,279 B1 | 8/2005 | Sollee et al. |
| 6,937,713 B1 | 8/2005 | Kung et al. |
| 6,940,950 B2 | 9/2005 | Dickinson et al. |
| 6,947,531 B1 | 9/2005 | Lewis et al. |
| 6,954,453 B1 | 10/2005 | Schindler |
| 6,954,455 B1 | 10/2005 | Al Hakim et al. |
| 6,954,654 B2 | 10/2005 | Ejzak |
| 6,961,334 B1 | 11/2005 | Kaczmarczyk |
| 6,963,557 B2 | 11/2005 | Knox |
| 6,963,739 B2 | 11/2005 | Dorenbosch et al. |
| 6,985,440 B1 | 1/2006 | Albert et al. |
| 6,993,015 B2 | 1/2006 | Kobayashi |
| 7,002,970 B1 | 2/2006 | Veschi |
| 7,006,508 B2 | 2/2006 | Bondy et al. |
| 7,010,727 B1 | 3/2006 | Stucker |
| 7,016,343 B1 | 3/2006 | Mermel et al. |
| 7,016,675 B1 | 3/2006 | Schuster et al. |
| 7,020,256 B2 | 3/2006 | Jain et al. |
| 7,027,564 B2 | 4/2006 | James |
| 7,027,582 B2 | 4/2006 | Khello et al. |
| 7,035,390 B2 | 4/2006 | Elliott |
| 7,042,985 B1 | 5/2006 | Wright |
| 7,046,658 B1 | 5/2006 | Kundaje |
| 7,047,561 B1 | 5/2006 | Lee |
| 7,050,426 B2 | 5/2006 | Veschi |
| 7,051,072 B2 | 5/2006 | Stewart et al. |
| 7,055,174 B1 | 5/2006 | Cope et al. |
| 7,068,668 B2 | 6/2006 | Feuer |
| 7,068,772 B1 | 6/2006 | Widger et al. |
| 7,079,526 B1 | 7/2006 | Wipliez et al. |
| 7,103,168 B2 | 9/2006 | Bedingfield, Sr. et al. |
| 7,110,523 B2 | 9/2006 | Gagle et al. |
| 7,111,035 B2 | 9/2006 | McClellan et al. |
| 7,120,682 B1 | 10/2006 | Salama |
| 7,127,488 B1 | 10/2006 | Scott et al. |
| 7,151,772 B1 | 12/2006 | Kalmanek, Jr. et al. |
| 7,174,156 B1 | 2/2007 | Mangal |
| 7,177,399 B2 | 2/2007 | Dawson et al. |
| 7,193,971 B2 | 3/2007 | McClellan |
| 7,203,478 B2 | 4/2007 | Benco et al. |
| 7,212,522 B1 | 5/2007 | Shankar et al. |
| 7,218,722 B1 | 5/2007 | Turner et al. |
| 7,239,629 B1 | 7/2007 | Olshansky et al. |
| 7,277,528 B2 | 10/2007 | Rao et al. |
| 7,283,507 B2 | 10/2007 | Buckley et al. |
| 7,289,493 B1 | 10/2007 | Vera |
| 7,298,833 B2 | 11/2007 | Klein et al. |
| 7,330,835 B2 | 2/2008 | Deggendorf |
| 7,346,156 B1 | 3/2008 | Choupak et al. |
| 7,359,368 B1 | 4/2008 | Pearce |
| 7,366,157 B1 | 4/2008 | Valentine et al. |
| 7,400,881 B2 | 7/2008 | Kallio |
| 7,412,049 B1 | 8/2008 | Koch |
| 7,426,492 B1 | 9/2008 | Bishop et al. |
| 7,436,835 B2 | 10/2008 | Castleberry et al. |
| 7,437,665 B2 | 10/2008 | Perham |
| 7,440,441 B2 | 10/2008 | Lakhani et al. |
| 7,440,442 B2 | 10/2008 | Grabelsky et al. |
| 7,447,707 B2 | 11/2008 | Gaurav et al. |
| 7,453,990 B2 | 11/2008 | Welenson et al. |
| 7,454,200 B2 | 11/2008 | Cai et al. |
| 7,454,510 B2 | 11/2008 | Kleyman et al. |
| 7,457,865 B2 | 11/2008 | Ramakrishnan et al. |
| 7,477,843 B1 | 1/2009 | Peeters et al. |
| 7,486,664 B2 | 2/2009 | Swartz |
| 7,486,667 B2 | 2/2009 | Feuer |
| 7,486,684 B2 | 2/2009 | Chu et al. |
| 7,512,117 B2 | 3/2009 | Swartz |
| 7,545,761 B1 | 6/2009 | Kalbag |
| 7,565,131 B2 | 7/2009 | Rollender |
| 7,573,982 B2 | 8/2009 | Breen et al. |
| 7,580,886 B1 | 8/2009 | Schulz |
| 7,587,036 B2 | 9/2009 | Wood et al. |
| 7,593,390 B2 | 9/2009 | Lebizay |
| 7,593,884 B2 | 9/2009 | Rothman et al. |
| 7,599,944 B2 | 10/2009 | Gaurav et al. |
| 7,602,886 B1 | 10/2009 | Beech et al. |
| 7,616,753 B2 | 11/2009 | Cope et al. |
| 7,623,447 B1 | 11/2009 | Faccin et al. |
| 7,639,792 B2 | 12/2009 | Qiu et al. |
| 7,644,037 B1 | 1/2010 | Ostrovsky |
| 7,647,500 B2 | 1/2010 | Machiraju et al. |
| 7,657,011 B1 | 2/2010 | Zielinski et al. |
| 7,664,495 B1 | 2/2010 | Bonner et al. |
| 7,668,159 B2 | 2/2010 | Buckley |
| 7,676,215 B2 | 3/2010 | Chin et al. |
| 7,676,431 B2 | 3/2010 | O'Leary et al. |
| 7,680,114 B2 | 3/2010 | Yazaki et al. |
| 7,680,737 B2 | 3/2010 | Smith et al. |
| 7,702,308 B2 | 4/2010 | Rollender |
| 7,710,950 B2 | 5/2010 | Buckley |
| 7,715,413 B2 | 5/2010 | Vaziri et al. |

(56) References Cited

U.S. PATENT DOCUMENTS

| | | | |
|---|---|---|---|
| 7,715,821 | B2 | 5/2010 | Rollender |
| 7,715,829 | B2 | 5/2010 | Li et al. |
| 7,734,544 | B2 | 6/2010 | Schleicher |
| 7,738,384 | B2 | 6/2010 | Pelletier |
| 7,760,707 | B1 | 7/2010 | Bates |
| 7,764,777 | B2 | 7/2010 | Wood et al. |
| 7,764,944 | B2 | 7/2010 | Rollender |
| 7,765,261 | B2 | 7/2010 | Kropivny |
| 7,765,263 | B1 | 7/2010 | Alfke |
| 7,765,266 | B2 | 7/2010 | Kropivny |
| 7,774,711 | B2 * | 8/2010 | Valeski ............... G06F 3/0482 715/752 |
| 7,797,459 | B1 | 9/2010 | Roy et al. |
| 7,822,188 | B1 | 10/2010 | Kirchhoff et al. |
| 7,830,868 | B2 | 11/2010 | Buckley |
| 7,836,136 | B1 | 11/2010 | Alfke |
| 7,882,011 | B2 | 2/2011 | Sandhu et al. |
| 7,894,441 | B2 | 2/2011 | Yazaki et al. |
| 7,899,742 | B2 | 3/2011 | Berkert et al. |
| 7,907,551 | B2 | 3/2011 | Croy et al. |
| 7,907,714 | B2 | 3/2011 | Baniak et al. |
| 7,916,846 | B1 | 3/2011 | Farah |
| 7,929,955 | B1 | 4/2011 | Bonner |
| 7,944,909 | B2 | 5/2011 | James |
| 7,950,046 | B2 | 5/2011 | Kropivny |
| 7,958,233 | B2 | 6/2011 | Gutierrez |
| 7,965,645 | B2 | 6/2011 | Pelletier |
| 7,979,529 | B2 | 7/2011 | Kreusch et al. |
| 7,995,565 | B2 | 8/2011 | Buckley |
| 7,995,589 | B2 | 8/2011 | Sollee et al. |
| 8,024,785 | B2 | 9/2011 | Andress et al. |
| 8,027,333 | B2 | 9/2011 | Grabelsky et al. |
| 8,036,362 | B1 | 10/2011 | Skinner |
| 8,036,366 | B2 | 10/2011 | Chu |
| 8,041,022 | B1 | 10/2011 | Andreasen et al. |
| 8,050,273 | B2 | 11/2011 | Gass |
| 8,060,887 | B2 | 11/2011 | Kropivny |
| 8,078,164 | B2 | 12/2011 | Ganesan |
| 8,111,690 | B2 | 2/2012 | Hussain et al. |
| 8,116,307 | B1 | 2/2012 | Thesayi et al. |
| 8,125,982 | B2 | 2/2012 | Feuer |
| 8,127,005 | B2 | 2/2012 | Gutierrez |
| 8,145,182 | B2 | 3/2012 | Rudolf et al. |
| 8,160,559 | B2 | 4/2012 | Buckley |
| 8,161,078 | B2 | 4/2012 | Gaurav et al. |
| 8,166,533 | B2 | 4/2012 | Yuan |
| 8,166,547 | B2 | 4/2012 | Bevan et al. |
| 8,189,568 | B2 | 5/2012 | Qiu et al. |
| 8,190,739 | B2 | 5/2012 | Gutierrez |
| 8,200,575 | B2 | 6/2012 | Torres et al. |
| 8,204,044 | B2 | 6/2012 | Lebizay |
| 8,219,115 | B1 | 7/2012 | Nelissen |
| 8,223,927 | B2 | 7/2012 | Di Serio et al. |
| 8,228,837 | B2 | 7/2012 | Sheriff et al. |
| 8,228,897 | B2 | 7/2012 | Mitchell |
| 8,243,730 | B1 | 8/2012 | Wong et al. |
| 8,244,204 | B1 | 8/2012 | Chen et al. |
| 8,275,404 | B2 | 9/2012 | Berger et al. |
| 8,300,632 | B2 | 10/2012 | Davis et al. |
| 8,306,021 | B2 | 11/2012 | Lawson et al. |
| 8,306,063 | B2 | 11/2012 | Erdal et al. |
| 8,315,521 | B2 | 11/2012 | Leiden et al. |
| 8,339,997 | B2 | 12/2012 | Dye et al. |
| 8,351,591 | B2 | 1/2013 | Kirchhoff et al. |
| 8,363,647 | B2 | 1/2013 | Fangman et al. |
| 8,364,172 | B2 | 1/2013 | Guanfeng et al. |
| 8,396,445 | B2 | 3/2013 | Crawford et al. |
| 8,410,907 | B2 | 4/2013 | Twitchell, Jr. |
| 8,417,791 | B1 | 4/2013 | Peretz et al. |
| 8,422,507 | B2 | 4/2013 | Björsell et al. |
| 8,423,791 | B1 | 4/2013 | Yu et al. |
| 8,427,981 | B2 | 4/2013 | Wyss et al. |
| 8,437,340 | B2 | 5/2013 | James |
| 8,462,915 | B2 | 6/2013 | Breen et al. |
| 8,468,196 | B1 | 6/2013 | Roskind et al. |
| 8,493,931 | B1 | 7/2013 | Nix |
| 8,509,225 | B2 | 8/2013 | Grabelsky et al. |
| 8,526,306 | B2 | 9/2013 | Jungck et al. |
| 8,532,075 | B2 | 9/2013 | Rassool et al. |
| 8,537,805 | B2 | 9/2013 | Björsell et al. |
| 8,542,815 | B2 | 9/2013 | Perreault et al. |
| 8,543,477 | B2 | 9/2013 | Love et al. |
| 8,594,298 | B2 | 11/2013 | Klein et al. |
| 8,599,747 | B1 | 12/2013 | Saleem et al. |
| 8,599,837 | B2 | 12/2013 | Kyle |
| 8,605,714 | B2 | 12/2013 | Lebizay |
| 8,605,869 | B1 | 12/2013 | Mobarak et al. |
| 8,607,323 | B2 | 12/2013 | Yuan |
| 8,611,354 | B2 | 12/2013 | Keränen et al. |
| 8,625,578 | B2 | 1/2014 | Roy et al. |
| 8,627,211 | B2 | 1/2014 | Kropivny |
| 8,630,234 | B2 | 1/2014 | Björsell et al. |
| 8,634,838 | B2 | 1/2014 | Hellwig et al. |
| 8,675,566 | B2 | 3/2014 | Huttunen et al. |
| 8,682,919 | B1 | 3/2014 | Golliher |
| 8,702,505 | B2 | 4/2014 | Kropivny |
| 8,713,098 | B1 | 4/2014 | Adya et al. |
| 8,724,643 | B2 | 5/2014 | Feuer |
| 8,731,163 | B1 | 5/2014 | Bates |
| 8,738,051 | B2 | 5/2014 | Nowack et al. |
| 8,749,610 | B1 | 6/2014 | Gossweiler et al. |
| 8,750,290 | B2 | 6/2014 | Vance et al. |
| 8,755,376 | B2 | 6/2014 | Lawson et al. |
| 8,763,081 | B2 | 6/2014 | Bogdanovic et al. |
| 8,767,717 | B2 | 7/2014 | Siegel et al. |
| 8,768,951 | B2 | 7/2014 | Crago |
| 8,774,171 | B2 | 7/2014 | Mitchell |
| 8,774,378 | B2 | 7/2014 | Björsell et al. |
| 8,774,721 | B2 | 7/2014 | Hertel et al. |
| 8,780,703 | B1 | 7/2014 | Eidelson et al. |
| 8,792,374 | B1 | 7/2014 | Jain et al. |
| 8,792,905 | B1 | 7/2014 | Li et al. |
| 8,804,705 | B2 | 8/2014 | Fangman et al. |
| 8,805,345 | B2 | 8/2014 | Ling et al. |
| 8,810,392 | B1 | 8/2014 | Teller et al. |
| 8,819,566 | B2 | 8/2014 | Mehin et al. |
| 8,837,360 | B1 | 9/2014 | Mishra et al. |
| 8,837,465 | B2 | 9/2014 | Lawson et al. |
| 8,838,539 | B1 | 9/2014 | Ashcraft et al. |
| 8,848,887 | B2 | 9/2014 | Willman et al. |
| 8,862,701 | B2 | 10/2014 | Havriluk |
| 8,885,609 | B2 | 11/2014 | Nix |
| 8,903,051 | B2 | 12/2014 | Li et al. |
| 8,903,360 | B2 | 12/2014 | Celi, Jr. et al. |
| 8,909,556 | B2 | 12/2014 | Huxham |
| 8,938,209 | B2 | 1/2015 | Crawford et al. |
| 8,938,534 | B2 | 1/2015 | Le et al. |
| 8,948,061 | B2 | 2/2015 | Sridhar |
| 8,972,612 | B2 | 3/2015 | Le et al. |
| 8,982,719 | B2 | 3/2015 | Seetharaman et al. |
| 8,995,428 | B2 | 3/2015 | Haster |
| 9,003,306 | B2 | 4/2015 | Mehin et al. |
| 9,094,525 | B2 | 7/2015 | Dye et al. |
| 9,137,385 | B2 | 9/2015 | Björsell et al. |
| 9,143,608 | B2 | 9/2015 | Björsell et al. |
| 9,154,417 | B2 | 10/2015 | Huttunen et al. |
| 9,179,005 | B2 * | 11/2015 | Perreault ............. H04M 15/888 |
| 9,253,332 | B2 | 2/2016 | Dye et al. |
| 9,432,830 | B2 | 8/2016 | Lahtiranta et al. |
| 9,462,122 | B1 | 10/2016 | Bates |
| 9,537,762 | B2 * | 1/2017 | Perreault ................. H04Q 3/70 |
| 9,549,071 | B2 | 1/2017 | Björsell et al. |
| 9,565,307 | B2 | 2/2017 | Björsell et al. |
| 9,813,330 | B2 * | 11/2017 | Perreault ............... A61K 45/06 |
| 9,826,002 | B2 * | 11/2017 | Perreault ............. H04L 65/1033 |
| 9,935,872 | B2 * | 4/2018 | Perreault ............... H04L 9/3226 |
| 9,948,549 | B2 * | 4/2018 | Perreault ............... A61K 45/06 |
| 9,998,363 | B2 | 6/2018 | Björsell et al. |
| 10,021,729 | B2 | 7/2018 | Huttunen et al. |
| 10,038,779 | B2 | 7/2018 | Björsell et al. |
| 10,218,606 | B2 * | 2/2019 | Perreault ........... H04M 15/8055 |
| 10,880,721 | B2 | 12/2020 | Bjorsell et al. |
| 11,171,864 | B2 | 11/2021 | Bjorsell |
| 2001/0027478 | A1 | 10/2001 | Meier et al. |

(56) References Cited

U.S. PATENT DOCUMENTS

| | | |
|---|---|---|
| 2001/0028642 A1 | 10/2001 | Veschi |
| 2001/0052081 A1 | 12/2001 | Mckibben et al. |
| 2002/0002041 A1 | 1/2002 | Lindgren et al. |
| 2002/0018445 A1 | 2/2002 | Kobayashi |
| 2002/0051518 A1 | 5/2002 | Bondy et al. |
| 2002/0057764 A1 | 5/2002 | Salvucci et al. |
| 2002/0068545 A1 | 6/2002 | Oyama et al. |
| 2002/0101974 A1 | 8/2002 | Zbib |
| 2002/0102973 A1 | 8/2002 | Rosenberg |
| 2002/0116464 A1 | 8/2002 | Mak |
| 2002/0122391 A1 | 9/2002 | Shalit |
| 2002/0122547 A1 | 9/2002 | Hinchey et al. |
| 2002/0141352 A1 | 10/2002 | Fangman et al. |
| 2002/0150080 A1 | 10/2002 | Bhattacharya |
| 2003/0008635 A1 | 1/2003 | Ung et al. |
| 2003/0012178 A1 | 1/2003 | Mussman et al. |
| 2003/0012196 A1 | 1/2003 | Ramakrishnan |
| 2003/0043974 A1 | 3/2003 | Emerson, III |
| 2003/0091028 A1 | 5/2003 | Chang et al. |
| 2003/0095539 A1 | 5/2003 | Feuer |
| 2003/0095541 A1 | 5/2003 | Chang et al. |
| 2003/0114145 A1 | 6/2003 | Boda et al. |
| 2003/0121967 A1 | 7/2003 | Goldberg et al. |
| 2003/0161458 A1 | 8/2003 | Da Palma et al. |
| 2003/0179747 A1 | 9/2003 | Pyke et al. |
| 2003/0200311 A1 | 10/2003 | Baum |
| 2003/0211840 A1 | 11/2003 | Castrogiovanni et al. |
| 2003/0219103 A1 | 11/2003 | Rao et al. |
| 2004/0009761 A1 | 1/2004 | Money et al. |
| 2004/0019539 A1 | 1/2004 | Raman et al. |
| 2004/0022237 A1 | 2/2004 | Elliot et al. |
| 2004/0034793 A1 | 2/2004 | Yuan |
| 2004/0157629 A1 | 8/2004 | Kallio et al. |
| 2004/0160968 A1 | 8/2004 | Ko et al. |
| 2004/0165709 A1 | 8/2004 | Pence et al. |
| 2004/0174975 A1 | 9/2004 | Sylvain et al. |
| 2004/0181599 A1 | 9/2004 | Kreusch et al. |
| 2004/0202160 A1 | 10/2004 | Westphal |
| 2004/0202295 A1 | 10/2004 | Shen et al. |
| 2004/0203565 A1 | 10/2004 | Chin et al. |
| 2004/0203582 A1 | 10/2004 | Dorenbosch et al. |
| 2004/0218748 A1 | 11/2004 | Fisher |
| 2004/0240439 A1 | 12/2004 | Castleberry et al. |
| 2004/0255126 A1 | 12/2004 | Reith |
| 2005/0007999 A1 | 1/2005 | Becker et al. |
| 2005/0021939 A1 | 1/2005 | Le et al. |
| 2005/0025043 A1 | 2/2005 | Mussman et al. |
| 2005/0058125 A1 | 3/2005 | Mutikainen et al. |
| 2005/0063519 A1 | 3/2005 | James |
| 2005/0068942 A1 | 3/2005 | Chu et al. |
| 2005/0069097 A1 | 3/2005 | Hanson et al. |
| 2005/0083911 A1 | 4/2005 | Grabelsky et al. |
| 2005/0094651 A1 | 5/2005 | Lutz et al. |
| 2005/0131813 A1 | 6/2005 | Gallagher et al. |
| 2005/0135401 A1 | 6/2005 | Schmidt |
| 2005/0164704 A1 | 7/2005 | Winsor |
| 2005/0169248 A1 | 8/2005 | Truesdale et al. |
| 2005/0171898 A1 | 8/2005 | Bishop et al. |
| 2005/0174937 A1 | 8/2005 | Scoggins et al. |
| 2005/0177843 A1 | 8/2005 | Williams |
| 2005/0186960 A1 | 8/2005 | Jiang |
| 2005/0188081 A1 | 8/2005 | Gibson et al. |
| 2005/0190892 A1 | 9/2005 | Dawson et al. |
| 2005/0192897 A1 | 9/2005 | Rogers et al. |
| 2005/0192901 A1 | 9/2005 | McCoy et al. |
| 2005/0195762 A1 | 9/2005 | Longoni et al. |
| 2005/0198499 A1 | 9/2005 | Salapaka et al. |
| 2005/0202799 A1 | 9/2005 | Rollender |
| 2005/0222952 A1 | 10/2005 | Garrett et al. |
| 2005/0249134 A1 | 11/2005 | Lin |
| 2005/0267842 A1 | 12/2005 | Weichert et al. |
| 2005/0287979 A1 | 12/2005 | Rollender |
| 2006/0006224 A1 | 1/2006 | Modi |
| 2006/0007940 A1 | 1/2006 | Sollee et al. |
| 2006/0013266 A1 | 1/2006 | Vega-Garcia et al. |
| 2006/0025122 A1 | 2/2006 | Harris et al. |
| 2006/0030290 A1 | 2/2006 | Rudolf et al. |
| 2006/0034270 A1 | 2/2006 | Haase et al. |
| 2006/0036522 A1 | 2/2006 | Perham |
| 2006/0072547 A1 | 4/2006 | Florkey et al. |
| 2006/0072550 A1 | 4/2006 | Davis et al. |
| 2006/0078094 A1 | 4/2006 | Breen et al. |
| 2006/0093135 A1 | 5/2006 | Fiatal et al. |
| 2006/0095320 A1 | 5/2006 | Jones |
| 2006/0109960 A1 | 5/2006 | D'Evelyn et al. |
| 2006/0111116 A1 | 5/2006 | Palmer et al. |
| 2006/0116892 A1 | 6/2006 | Grimes et al. |
| 2006/0142011 A1 | 6/2006 | Kallio |
| 2006/0146797 A1 | 7/2006 | Lebizay |
| 2006/0153342 A1 | 7/2006 | Sasaki |
| 2006/0160565 A1 | 7/2006 | Singh et al. |
| 2006/0177035 A1 | 8/2006 | Cope et al. |
| 2006/0189303 A1 | 8/2006 | Rollender |
| 2006/0195398 A1 | 8/2006 | Dheer et al. |
| 2006/0195584 A1 | 8/2006 | Baumann |
| 2006/0205383 A1 | 9/2006 | Rollender et al. |
| 2006/0209768 A1 | 9/2006 | Yan et al. |
| 2006/0233317 A1 | 10/2006 | Coster et al. |
| 2006/0248186 A1 | 11/2006 | Smith |
| 2006/0251056 A1 | 11/2006 | Feuer |
| 2006/0258328 A1 | 11/2006 | Godoy |
| 2006/0264200 A1 | 11/2006 | Laiho et al. |
| 2006/0268921 A1 | 11/2006 | Ekstrom et al. |
| 2006/0281437 A1 | 12/2006 | Cook |
| 2006/0291643 A1 | 12/2006 | Pfaff et al. |
| 2007/0016524 A1 | 1/2007 | Diveley et al. |
| 2007/0036139 A1 | 2/2007 | Patel et al. |
| 2007/0036143 A1 | 2/2007 | Alt et al. |
| 2007/0047548 A1 | 3/2007 | Yazaki et al. |
| 2007/0053382 A1 | 3/2007 | Bevan et al. |
| 2007/0060097 A1 | 3/2007 | Edge et al. |
| 2007/0061397 A1 | 3/2007 | Gregorat et al. |
| 2007/0064919 A1 | 3/2007 | Chen et al. |
| 2007/0092070 A1 | 4/2007 | Croy et al. |
| 2007/0112964 A1 | 5/2007 | Guedalia et al. |
| 2007/0115935 A1 | 5/2007 | Qiu et al. |
| 2007/0121590 A1* | 5/2007 | Turner .................. H04M 7/009 370/352 |
| 2007/0121593 A1 | 5/2007 | Vance et al. |
| 2007/0121602 A1 | 5/2007 | Sin |
| 2007/0121866 A1 | 5/2007 | Kniveton et al. |
| 2007/0127449 A1 | 6/2007 | Nix et al. |
| 2007/0127452 A1 | 6/2007 | Croy |
| 2007/0127676 A1 | 6/2007 | Khadri |
| 2007/0165612 A1 | 7/2007 | Buckley |
| 2007/0174469 A1 | 7/2007 | Andress et al. |
| 2007/0217354 A1 | 9/2007 | Buckley |
| 2007/0220038 A1 | 9/2007 | Crago |
| 2007/0230423 A1 | 10/2007 | Yoshida et al. |
| 2007/0238468 A1 | 10/2007 | Buckley et al. |
| 2007/0238472 A1 | 10/2007 | Wanless |
| 2007/0253407 A1 | 11/2007 | Wang et al. |
| 2007/0253418 A1 | 11/2007 | Shiri et al. |
| 2007/0253429 A1 | 11/2007 | James |
| 2007/0263609 A1 | 11/2007 | Mitchell |
| 2007/0286170 A1 | 12/2007 | Khan et al. |
| 2007/0297376 A1 | 12/2007 | Gass |
| 2008/0013523 A1 | 1/2008 | Nambakkam |
| 2008/0014901 A1 | 1/2008 | Motley et al. |
| 2008/0037715 A1 | 2/2008 | Prozeniuk et al. |
| 2008/0037729 A1 | 2/2008 | Mobin et al. |
| 2008/0043659 A1 | 2/2008 | Richards et al. |
| 2008/0043718 A1 | 2/2008 | Chu |
| 2008/0056235 A1 | 3/2008 | Albina et al. |
| 2008/0056243 A1 | 3/2008 | Roy et al. |
| 2008/0056302 A1 | 3/2008 | Erdal et al. |
| 2008/0063153 A1 | 3/2008 | Krivorot et al. |
| 2008/0097845 A1 | 4/2008 | Altberg et al. |
| 2008/0107254 A1 | 5/2008 | Yamartino |
| 2008/0137642 A1 | 6/2008 | Teodosiu et al. |
| 2008/0160953 A1 | 7/2008 | Mia et al. |
| 2008/0166999 A1 | 7/2008 | Guedalia et al. |
| 2008/0167019 A1 | 7/2008 | Guedalia et al. |
| 2008/0167020 A1 | 7/2008 | Guedalia et al. |

(56) References Cited

U.S. PATENT DOCUMENTS

| | | |
|---|---|---|
| 2008/0167039 A1 | 7/2008 | Guedalia et al. |
| 2008/0187122 A1 | 8/2008 | Baker |
| 2008/0188198 A1 | 8/2008 | Patel et al. |
| 2008/0188227 A1 | 8/2008 | Guedalia et al. |
| 2008/0205378 A1 | 8/2008 | Wyss et al. |
| 2008/0261560 A1 | 10/2008 | Ruckart |
| 2008/0280617 A1 | 11/2008 | Aguilar et al. |
| 2008/0310599 A1 | 12/2008 | Purnadi et al. |
| 2009/0003535 A1 | 1/2009 | Grabelsky et al. |
| 2009/0012851 A1 | 1/2009 | Marc |
| 2009/0017842 A1 | 1/2009 | Fukasaku |
| 2009/0028146 A1 | 1/2009 | Kleyman et al. |
| 2009/0047922 A1 | 2/2009 | Buckley |
| 2009/0129566 A1 | 5/2009 | Feuer |
| 2009/0135724 A1 | 5/2009 | Zhang et al. |
| 2009/0135735 A1 | 5/2009 | Zhang et al. |
| 2009/0141883 A1 | 6/2009 | Bastien |
| 2009/0213839 A1 | 8/2009 | Davis et al. |
| 2009/0214000 A1 | 8/2009 | Patel et al. |
| 2009/0238168 A1 | 9/2009 | Lavoie et al. |
| 2009/0268615 A1 | 10/2009 | Pelletier |
| 2009/0292539 A1 | 11/2009 | Jaroker |
| 2009/0296900 A1 | 12/2009 | Breen et al. |
| 2009/0325558 A1 | 12/2009 | Pridmore et al. |
| 2010/0002701 A1 | 1/2010 | Hsieh et al. |
| 2010/0008345 A1 | 1/2010 | Lebizay |
| 2010/0039946 A1 | 2/2010 | Imbimbo et al. |
| 2010/0083364 A1 | 4/2010 | Gutierrez |
| 2010/0086119 A1 | 4/2010 | De Luca et al. |
| 2010/0105379 A1 | 4/2010 | Bonner et al. |
| 2010/0114896 A1 | 5/2010 | Clark et al. |
| 2010/0115018 A1 | 5/2010 | Yoon et al. |
| 2010/0128729 A1 | 5/2010 | Yazaki et al. |
| 2010/0142382 A1 | 6/2010 | Jungck et al. |
| 2010/0150138 A1 | 6/2010 | Björsell et al. |
| 2010/0150328 A1 | 6/2010 | Perrault et al. |
| 2010/0172345 A1 | 7/2010 | Björsell et al. |
| 2010/0177671 A1 | 7/2010 | Qiu et al. |
| 2010/0220852 A1 | 9/2010 | Willman et al. |
| 2010/0233991 A1 | 9/2010 | Crawford et al. |
| 2010/0246589 A1 | 9/2010 | Pelletier |
| 2010/0272242 A1 | 10/2010 | Croy et al. |
| 2010/0278534 A1 | 11/2010 | Leiden et al. |
| 2010/0316195 A1 | 12/2010 | Di Serio et al. |
| 2011/0013541 A1 | 1/2011 | Croy et al. |
| 2011/0072095 A1 | 3/2011 | Havriluk |
| 2011/0122827 A1 | 5/2011 | Björsell et al. |
| 2011/0153809 A1 | 6/2011 | Ghanem et al. |
| 2011/0167164 A1 | 7/2011 | Gutierrez |
| 2011/0176541 A1 | 7/2011 | James |
| 2011/0201321 A1 | 8/2011 | Bonner |
| 2011/0208859 A1 | 8/2011 | Gutierrez |
| 2011/0235543 A1 | 9/2011 | Seetharaman et al. |
| 2011/0255553 A1 | 10/2011 | Bobba et al. |
| 2011/0261717 A1 | 10/2011 | Akuzuwa et al. |
| 2011/0267986 A1 | 11/2011 | Grabelsky et al. |
| 2011/0273526 A1 | 11/2011 | Mehin et al. |
| 2011/0276903 A1 | 11/2011 | Mehin et al. |
| 2011/0276904 A1 | 11/2011 | Mehin et al. |
| 2011/0292929 A1 | 12/2011 | Haster |
| 2012/0014383 A1 | 1/2012 | Geromel et al. |
| 2012/0089717 A1 | 4/2012 | Chen |
| 2012/0096145 A1 | 4/2012 | Le et al. |
| 2012/0099599 A1 | 4/2012 | Keränen et al. |
| 2012/0113981 A1 | 5/2012 | Feuer |
| 2012/0155333 A1 | 6/2012 | Yoon et al. |
| 2012/0170574 A1 | 7/2012 | Huttunen et al. |
| 2012/0195236 A1 | 8/2012 | Knight |
| 2012/0195415 A1 | 8/2012 | Wyss et al. |
| 2012/0227101 A1 | 9/2012 | Yuan |
| 2012/0250624 A1 | 10/2012 | Lebizay |
| 2012/0259975 A1 | 10/2012 | Le et al. |
| 2012/0270554 A1 | 10/2012 | Hellwig et al. |
| 2012/0282881 A1 | 11/2012 | Mitchell |
| 2012/0314699 A1 | 12/2012 | Qiu et al. |
| 2013/0039226 A1 | 2/2013 | Sridhar |
| 2013/0097308 A1 | 4/2013 | Le et al. |
| 2013/0114589 A1 | 5/2013 | Fangman et al. |
| 2013/0128879 A1 | 5/2013 | Kyle |
| 2013/0148549 A1 | 6/2013 | Crawford et al. |
| 2013/0173534 A1 | 7/2013 | Nelakonda et al. |
| 2013/0223276 A1 | 8/2013 | Padgett |
| 2013/0229950 A1 | 9/2013 | Björsell et al. |
| 2013/0237198 A1 | 9/2013 | Vashi et al. |
| 2013/0254301 A1 | 9/2013 | Lin et al. |
| 2013/0272297 A1 | 10/2013 | Breen et al. |
| 2013/0281147 A1 | 10/2013 | Denman et al. |
| 2013/0287006 A1 | 10/2013 | Nix |
| 2013/0310002 A1 | 11/2013 | Celi, Jr. et al. |
| 2013/0318166 A1 | 11/2013 | Jungck et al. |
| 2013/0329722 A1 | 12/2013 | Perrault et al. |
| 2013/0329864 A1 | 12/2013 | Björsell et al. |
| 2014/0010119 A1 | 1/2014 | Björsell et al. |
| 2014/0016764 A1 | 1/2014 | Björsell et al. |
| 2014/0024367 A1 | 1/2014 | Björsell et al. |
| 2014/0101749 A1 | 4/2014 | Yuan |
| 2014/0141884 A1 | 5/2014 | Kropivny |
| 2014/0153477 A1 | 6/2014 | Huttunen et al. |
| 2014/0211789 A1 | 7/2014 | Feuer |
| 2014/0215642 A1 | 7/2014 | Huxham |
| 2014/0220944 A1 | 8/2014 | Balasubramanian |
| 2014/0244393 A1 | 8/2014 | Rimmer et al. |
| 2014/0247730 A1 | 9/2014 | Thota et al. |
| 2014/0269624 A1 | 9/2014 | Khay-Ibbat et al. |
| 2014/0307858 A1 | 10/2014 | Li et al. |
| 2014/0321333 A1 | 10/2014 | Björsell et al. |
| 2014/0324969 A1 | 10/2014 | Riddle |
| 2014/0337961 A1 | 11/2014 | Chien et al. |
| 2014/0337962 A1 | 11/2014 | Brandstatter |
| 2014/0349602 A1 | 11/2014 | Majumdar et al. |
| 2015/0327320 A1 | 11/2015 | Huttunen et al. |
| 2015/0358470 A1 | 12/2015 | Björsell et al. |
| 2016/0006882 A1 | 1/2016 | Björsell et al. |
| 2016/0028619 A1 | 1/2016 | Perreault et al. |
| 2017/0104868 A1 | 4/2017 | Björsell et al. |
| 2017/0111265 A1 | 4/2017 | Perreault et al. |
| 2017/0126752 A1 | 5/2017 | Perreault et al. |
| 2017/0142256 A1 | 5/2017 | Björsell et al. |
| 2019/0199621 A1 | 6/2019 | Perreault et al. |

FOREIGN PATENT DOCUMENTS

| | | |
|---|---|---|
| CA | 2 218 218 A1 | 10/1997 |
| CA | 2249668 A1 | 4/1999 |
| CA | 2 299 037 A1 | 8/2000 |
| CA | 2 437 275 A1 | 10/2002 |
| CA | 2598200 A1 | 2/2008 |
| CA | 2668025 A1 | 5/2008 |
| CA | 3045681 A1 | 5/2008 |
| CA | 3045683 A1 | 5/2008 |
| CA | 3045694 A1 | 5/2008 |
| CA | 2670510 A1 | 6/2008 |
| CA | 2 681 984 A1 | 10/2008 |
| CA | 2 690 236 A1 | 12/2008 |
| CA | 2 659 007 A1 | 9/2009 |
| CA | 2732148 A1 | 2/2010 |
| CA | 2 778 905 A1 | 8/2010 |
| CA | 2812174 A1 | 3/2011 |
| CA | 2812174 C | 5/2018 |
| CA | 2732148 C | 6/2018 |
| CA | 2668025 C | 2/2020 |
| CA | 3045672 C | 1/2021 |
| CA | 3032707 C | 2/2021 |
| CN | 1498029 A | 5/2004 |
| CN | 1498482 A | 5/2004 |
| CN | 1668137 A | 9/2005 |
| CN | 1274114 C | 9/2006 |
| CN | 101005503 A | 7/2007 |
| CN | 101069390 A | 11/2007 |
| CN | 101095329 A | 12/2007 |
| CN | 101584150 A | 11/2009 |
| CN | 101584166 A | 11/2009 |
| CN | 101605342 A | 12/2009 |
| CN | 1498029 B | 5/2010 |

(56) References Cited

FOREIGN PATENT DOCUMENTS

| | | |
|---|---|---|
| CN | 101772929 A | 7/2010 |
| CN | 101069390 B | 12/2010 |
| CN | 102137024 A | 7/2011 |
| CN | 102457494 A | 5/2012 |
| CN | 102484656 A | 5/2012 |
| CN | 102572123 A | 7/2012 |
| CN | 101095329 B | 10/2012 |
| CN | 101605342 B | 12/2012 |
| CN | 102833232 A | 12/2012 |
| CN | 101005503 B | 1/2013 |
| CN | 101772929 B | 7/2014 |
| CN | 102457494 B | 10/2014 |
| DE | 602 01 827 T2 | 11/2005 |
| DE | 11 2005 003 306 T5 | 1/2008 |
| DE | 601 33 316 T2 | 7/2008 |
| DE | 603 17 751 T2 | 11/2008 |
| EP | 0 841 832 A2 | 5/1998 |
| EP | 0 841 832 A3 | 5/1999 |
| EP | 1 032 224 A2 | 8/2000 |
| EP | 1054569 A1 | 11/2000 |
| EP | 1 032 224 A3 | 2/2001 |
| EP | 1 244 250 A1 | 9/2002 |
| EP | 1 266 516 A2 | 12/2002 |
| EP | 1 362 456 A2 | 11/2003 |
| EP | 1 371 173 A1 | 12/2003 |
| EP | 1 389 862 A1 | 2/2004 |
| EP | 1 411 743 A1 | 4/2004 |
| EP | 1168781 B1 | 5/2004 |
| EP | 1 389 862 B1 | 11/2004 |
| EP | 1 526 697 A2 | 4/2005 |
| EP | 1 362 456 A4 | 5/2005 |
| EP | 1 575 327 A1 | 9/2005 |
| EP | 1 610 583 A1 | 12/2005 |
| EP | 1 526 697 A3 | 3/2006 |
| EP | 1 721 446 A1 | 11/2006 |
| EP | 1806899 A1 | 7/2007 |
| EP | 1816823 B1 | 8/2007 |
| EP | 1 829 300 A1 | 9/2007 |
| EP | 1 371 173 B1 | 11/2007 |
| EP | 1 411 743 B1 | 11/2007 |
| EP | 1887752 A1 | 2/2008 |
| EP | 1 362 456 B1 | 3/2008 |
| EP | 1909451 B1 | 4/2008 |
| EP | 1 974 304 A2 | 10/2008 |
| EP | 1 974 304 A4 | 10/2008 |
| EP | 1 610 583 B1 | 8/2009 |
| EP | 2 084 868 A0 | 8/2009 |
| EP | 2 090 024 A0 | 8/2009 |
| EP | 2 127 232 A1 | 12/2009 |
| EP | 2 165 489 A1 | 3/2010 |
| EP | 2 215 755 A1 | 8/2010 |
| EP | 2 227 048 A1 | 9/2010 |
| EP | 2 127 232 A4 | 3/2011 |
| EP | 2 165 489 A4 | 3/2011 |
| EP | 2 311 292 A0 | 4/2011 |
| EP | 1 829 300 A4 | 5/2012 |
| EP | 2 449 749 A1 | 5/2012 |
| EP | 2 478 678 A0 | 7/2012 |
| EP | 2 215 755 A4 | 10/2012 |
| EP | 1 829 300 B1 | 11/2012 |
| EP | 2 449 749 B1 | 3/2014 |
| EP | 1 266 516 B1 | 5/2014 |
| EP | 2084868 B1 | 5/2018 |
| EP | 3386155 A1 | 10/2018 |
| GB | 2 332 337 A | 6/1999 |
| GB | 2 331 197 A | 12/1999 |
| IN | 24/2009 | 6/2009 |
| IN | 29/2009 | 7/2009 |
| IN | 287412 | 9/2017 |
| JP | 2011-199384 A | 10/2011 |
| KR | 10-2009-0086428 A | 8/2009 |
| KR | 10-2009-0095621 A | 9/2009 |
| MX | 2009004811 A | 8/2009 |
| MX | 2009005751 A | 8/2009 |
| SG | 151991 A1 | 6/2009 |
| SG | 152752 A1 | 6/2009 |
| SG | 155474 | 10/2009 |
| WO | WO 2000/069156 A1 | 11/2000 |
| WO | WO 2001/006740 A2 | 1/2001 |
| WO | WO 01/50693 A1 | 7/2001 |
| WO | WO 2001061947 A1 | 8/2001 |
| WO | WO 01/69899 A2 | 9/2001 |
| WO | WO 01/69899 A3 | 9/2001 |
| WO | WO 01/80587 A1 | 10/2001 |
| WO | WO 01/89145 A2 | 11/2001 |
| WO | WO 0223851 A2 | 3/2002 |
| WO | WO 0225889 A2 | 3/2002 |
| WO | WO 02/082728 A1 | 10/2002 |
| WO | WO 02/082782 A2 | 10/2002 |
| WO | WO 02/082782 A3 | 10/2002 |
| WO | WO 03/027801 A2 | 4/2003 |
| WO | WO 2003028355 A1 | 4/2003 |
| WO | WO 2003/096559 A1 | 11/2003 |
| WO | WO 2004/008786 A1 | 1/2004 |
| WO | WO 2004/102941 A1 | 11/2004 |
| WO | WO 2005/077054 A1 | 8/2005 |
| WO | WO 2005/084002 A1 | 9/2005 |
| WO | WO 2005/122541 A2 | 12/2005 |
| WO | WO 2005/125163 A1 | 12/2005 |
| WO | WO 2006/067269 A1 | 6/2006 |
| WO | WO 2006/072099 A1 | 7/2006 |
| WO | WO 2006/078175 A2 | 7/2006 |
| WO | WO 2006/078175 A3 | 7/2006 |
| WO | WO 2007016447 A2 | 2/2007 |
| WO | WO 2007/044454 A2 | 4/2007 |
| WO | WO 2007/056158 A2 | 5/2007 |
| WO | WO 2007/087077 A2 | 8/2007 |
| WO | WO 2007/087077 A3 | 8/2007 |
| WO | WO 2008/027065 A1 | 3/2008 |
| WO | WO 2008/052340 A1 | 5/2008 |
| WO | WO 2008/064481 A1 | 6/2008 |
| WO | WO 2008/085614 A2 | 7/2008 |
| WO | WO 2008/085614 A3 | 7/2008 |
| WO | WO 2008/086350 A2 | 7/2008 |
| WO | WO 2008/086350 A3 | 7/2008 |
| WO | WO 2008/103652 A1 | 8/2008 |
| WO | WO 2008/116296 A1 | 10/2008 |
| WO | WO 2008/085614 A8 | 12/2008 |
| WO | WO 2008/151406 A1 | 12/2008 |
| WO | WO 2008/151406 A8 | 12/2008 |
| WO | WO 2009/070202 A1 | 6/2009 |
| WO | WO 2009/070278 A1 | 6/2009 |
| WO | WO0200902627 | 9/2009 |
| WO | WO 2010/012090 A2 | 2/2010 |
| WO | WO 2011/000405 A1 | 1/2011 |
| WO | WO 2011/032256 A1 | 3/2011 |
| WO | WO 2013/013189 A2 | 1/2013 |
| WO | WO 2013/120069 A1 | 8/2013 |
| WO | WO 2014/066155 A2 | 5/2014 |
| WO | WO 2014/117599 A1 | 8/2014 |
| WO | WO 2014/166258 A1 | 10/2014 |

OTHER PUBLICATIONS

Abrazhevich, Dennis. "Electronic Payment Systems: a User-Centered Perspective and Interaction Design," *Thesis under the auspices of the J.F. Schouten School for User-System Interaction Research*, Technische Universiteit Eindhoven, Netherlands, 2004, pages Cover page-p. 189.

Baker et al., "Cisco Support for Lawful Intercept In IP Networks," Internet Draft—working document of the Internet Engineering Task Force (IETF), accessible at http://www.ietf.org/ietf/lid-abstracts.txt, Apr. 2003, expires Sep. 30, 2003, pp. 1-15.

F. Baker et al. "RFC 3924—Cisco Architecture for Lawful Intercept in IP Networks." Oct. 2004.

Bhushan et al., "Federated Accounting: Service Charging and Billing in a Business-to-Business Environment," 0-7803-6719-7/01, @ 2001 IEEE, pp. 107-121.

Cisco. "Lawful Intercept Requirements Summary." http://www.fags.org/rfcs/rfcs3924.html. Nov. 8, 2006.

DOTS IP Address Validation, "Overview", http://www.serviceobjects.com/products/dots_ipgeo.asp; printed Jun. 21, 2012.

(56) References Cited

OTHER PUBLICATIONS

DOTS Phone Exchange, "Overview", http://www.serviceobjects.com/demos/PhoneExchangeDemo.asp (URL No. longer valid, current URL is http://www.serviceobjects.com/products/phone/phone-exchange); printed Jun. 21, 2012.
ETSI Technical Specification. "Lawful Interception (LI); Handover Interface and Service-Specific|Details (SSD) for IP delivery; Part 5: Service-specific details for IP Multimedia Services." Apr. 2008, 25 pgs, v.2.3.1, France.
Handley, M. et al. "RFC 2543—SIP: Session Initiation Protocol." Mar. 1999.
IETF ENUM WG R STASTNY OEFEG Informational Numbering for Voip and Other IP |Communications: "Numbering for ViOP and other IP Communications, draft-stastny-enum-numbering-voip-00.txt", 20031001, Oct. 1, 2003, pp. 1-43, XP015035676, Issn: 0000-0004.
Ip2Location, http://www.ip2location.com/; printed Jun. 20, 2012.
ETSI TS 122 173 V12.7.0 (Oct. 2014) Digital cellular telecommunications system (Phase 2+); Technical Specification 8.2.2.3—Interoperability with PSTN/ISDN and mobile CS Networks, Contents and Forward, pp. 1-9; Sec. 8, pp. 14-17.
Huitema et al., "Architecture for Internet Telephony Service for Residential Customers," Academic Paper for *Bellcore*, Mar. 2, 1999, pp. 1-14.
Jajszczyk et al., "Emergency Calls in Flow-Aware Networks," *IEEE Communications Letters*, vol. 11, No. 9, Sep. 2007, pp. 753-755.
Ketchpel et al. "U-Pai: A universal payment application interface" Second *USENIX Workshop on Electronic Commerce Proceedings*, 1996-8, pp. 1-17.
Kim et al., "An Enhanced VoIP Emergency Services Prototype," *Proceedings of the 3$^{rd}$ International ISCRAM Conference (B. Van de Walle and M. Turoff, eds.)*, Newark, NJ (USA), May 2006, pp. 1-8.
Kornfeld et al., "DVB-H and IP Datacast—Broadcast to Handheld Devices," *IEEE Transactions On Broadcasting*, vol. 53, No. 1, Mar. 2007, pp. 161-170.
Kortebi et al., "SINR-Based Routing in Multi-Hop Wireless Networks to Improve VoIP Applications Support," 1-4244-0667-6/07, @ 2007 IEEE, pp. 491-496.
Lee et al., "VoIP Interoperation with KT-NGN," in *The 6$^{th}$ International Conference on AdvancedCommunication Technology*, Technical Proceedings, 2004, pp. 126-128, accompanied by Title and Contents—4 pages.
Lin et al., "Effective VoIP Call Routing in WLAN and Cellular Integration," *IEEE Communications Letters*, vol. 9, No. 10, Oct. 2005, pp. 874-876.
Lind AT&T S: "ENUM Call Flows for VoIP Interworking; draft-lind-enum-callflows-03.txt", 20020201, No. 3, Feb. 1, 2002, pp. 1-17, XP015004214, ISSN: 0000-0004.
List of North American Numbering Plan area codes, http://en.wikipedia.org/wiki/List_of_NANP_area_codes; printed Jun. 20, 2012.
Ma et al., "Realizing MPEG4 Video Transmission Based on Mobile Station over GPRS," 0-7803-9335-X/05, C 2005 IEEE, pp. 1241-1244.
Mintz-Habib et al., "A VoIP Emergency Services Architecture and Prototype," {mm2571,asr,hgs,xiaotaow}@cs.columbia.edu, 0-7803-9428-3/05, @ 2005 IEEE, pp. 523-528.
Moberg & Drummond, "MIME-Based Secure Peer-to-Peer Business Data Interchange Using HTTP, Applicability Statement 2 (AS2)," *Network Working Group, Request for Comments: 4130, Category: Standards Track*, Copyright @ The Internet Society Jul. 2005, pp. 1-47.
Munir, Muhammad Farukh, "Study of an Adaptive Scheme for Voice Transmission on IP in a Wireless Networking Environment 802.11e," *Dept. of Networks and Distributed Computing, Ecole Supérieure En Sciences Informatiques (ESSI), Université De Nice*, Jun. 2005, (pp. 1-35), Best Available Copy—pp. 1-11.
Rosenberg, et al.; "RFC 3261—SIP: Session Initiation Protocol", Jun. 2002.
Sippy Sip B2BUA. "About Sipov RTPproxy." http://www.rtpproxy.org, Jul. 15, 2009.
Sripanidkulchai et al., "Call Routing Management in Enterprise VoIP Networks," *Copyright 2007 ACM* 978-1-59593-788-9/07/0008, 6 pages.
Stallings, William, "The Session Initiation Protocol," *The Internet Protocol Journal*, vol. 6, No. 1, Mar. 2003, pp. 20-30.
Technical Report, "3rd Generation Partnership Project; Technical Specification Group Core Network and Terminals; Study into routeing of MT-SMs via the HPLMN (Release 7)," *3GPP TR 23.840 V0.1.0* (Feb. 2006), 13 pages.
Thernelius, Fredrik, "SIP, NAT, and Firewalls," Master's Thesis, *Ericsson*, Department of Teleinformatics, May 2000, pp. 1-69.
Townsley, et al.; "RFC 2661—Layer Two Tunneling Protocol 'L2TP' ", Aug. 1999.
Trad et al., "Adaptive VoIP Transmission over Heterogeneous Wired/Wireless Networks," *V. Roca and F. Rousscau (Eds.): MIPS 2004, LNCS* 3311, pp. 25-36, 2004, @ Springer-Verlag Berlin Heidelberg 2004.
Wikipedia, "International mobile subscriber identity (IMSI)," http://en.wikipedia.org/wiki/IMSI, Jul. 16, 2013.
Wikipedia, "Roaming," http://en.wikipedia.org/wiki/Roaming, Jul. 16, 2013.
Yu et al., "Service-Oriented Issues: Mobility, Security, Charging and Billing Management in Mobile Next Generation Networks," IEEE BcN2006, 1-4244-0146-1/06, @ 2006 IEEE, pp. 1-10.
International Search Report and Written Opinion of the International Searching Authority completed Jun. 6, 2008 for PCT/CA2008/000545.
International Search Report and Written Opinion of the International Searching Authority completed Feb. 6, 2008 for PCT/CA2007/001956.
International Preliminary Report on Patentability mailed May 14, 2009 for PCT/CA2007/001956.
International Search Report and Written Opinion of the International Searching Authority completed Mar. 3, 2008 for PCT/CA2007/002150.
International Preliminary Report on Patentability mailed Feb. 13, 2009 for PCT/CA2007/002150.
International Preliminary Report on Patentability and Written Opinion of the International Searching Authority mailed Feb. 10, 2011 for PCT/CA2009/001062.
International Search Report and Written Opinion completed on Jun. 18, 2010 for PCT/CA2009/001317.
International Search Report and Written Opinion mailed on Mar. 12, 2010 for PCT/CA2009/001062.
International Preliminary Report on Patentability issued on Sep. 29, 2009 for PCT/CA2008/000545.
International Preliminary Report on Patentability issued on Mar. 20, 2012 for PCT/CA2009/001317.
Canadian Office Action dated Jan. 27, 2015 for Canadian Patent Application No. CA 2,681,984.
Canadian Office Action dated Nov. 18, 2015 for Canadian Patent Application No. CA 2,681,984.
Canadian Office Action dated Dec. 1, 2015 for Canadian Patent Application No. CA 2,812,174.
Canadian Office Action dated Jan. 22, 2016 for Canadian Patent Application No. CA 2,916,220.
Canadian Office Action dated Mar. 3, 2016 for Canadian Patent Application No. CA 2,670,510.
Canadian Office Action dated Jun. 8, 2016 for Canadian Patent Application No. CA 2,916,217.
Canadian Office Action dated Aug. 16, 2016 for Canadian Patent Application No. CA 2,681,984.
Canadian Office Action dated Mar. 31, 2017 for Canadian Patent Application No. CA 2,916,220.
Canadian Office Action dated Apr. 27, 2018 for Canadian Patent Application No. CA 2,916,220.
Canadian Office Action dated Nov. 7, 2014 for Canadian Patent Application No. CA 2,668,025.
Canadian Office Action dated May 14, 2018 for Canadian Patent Application No. CA 2,668,025.
Canadian Office Action dated May 29, 2017 for Canadian Patent Application No. CA 2,668,025.

(56) References Cited

OTHER PUBLICATIONS

Canadian Office Action dated Jun. 9, 2017 for Canadian Patent Application No. CA 2,916,217.
Canadian Office Action dated Aug. 2, 2017 for Canadian Patent Application No. CA 2,681,984.
Canadian Office Action dated Sep. 18, 2014 for Canadian Patent Application No. CA 2,670,510.
Canadian Office Action dated Aug. 18, 2015 for Canadian Patent Application No. CA 2,732,148.
Chinese Office Action dated Mar. 24, 2011 for Chinese Patent Application No. CN 200780049791.5.
Chinese Office Action dated Jun. 23, 2011 for Chinese Patent Application No. CN 200780049136.X.
Extended European Search Report dated Nov. 2, 2012 for European Application No. EP 07 855 436.7.
Extended European Search Report dated Dec. 20, 2013 for European Application No. EP 09 849 358.8.
Extended European Search Report dated Apr. 16, 2014 for European Patent Application No. EP 09 802 316.1.
Supplementary European Search Report for European Application No. 07 816 106, dated Jun. 18, 2012.
European Examination Report dated Nov. 26, 2015 for European Patent Application No. EP 07 816 106.4.
Communication for European Patent Application No. EP 07 816 106.4—Invitation pursuant to Article 94(3) and Rule 71(1) EPC dated Apr. 15, 2016. All pages.
European Examination Report dated Aug. 29, 2016 for European Patent Application No. EP 07 855 436.7.
Communication under Rule 71(3) EPC—Intention to Grant—dated Oct. 14, 2016 for European Patent Application No. EP 07 816 106.4.
European Examination Report dated May 12, 2017 for European Patent Application No. EP 09-802-316.1.
Extended European Search Report dated Jul. 5, 2018 for European Application No. 18 174 930.0.
European Examination Report and Summons to Oral Proceedings dated Jun. 4, 2018 for European Patent Application No. 07 855 436.7.
First Examination Report dated Dec. 9, 2015, India Patent Application No. 1047/MUMNP/2009, which corresponds to subject U.S. Appl. No. 14/802,929.
Indian Office Action dated Jun. 21, 2017 for Indian Patent Application No. IN 1227/MUMNP/2009.
Intimation of the grant and recordal of India Patent No. 28/7412 entitled "Producing Routing Messages for Voice Over IP Communications", dated Sep. 15, 2017, for India Patent Application No. IN 1047/MUMNP/2009 filed Nov. 1, 2007.
Indonesian Examination Report dated Jul. 5, 2012 for Indonesian Patent Application No. W-00200901414.
Indonesian Examination Report dated Feb. 8, 2013 for Indonesian Patent Application No. W-00200901165.
Mexican Exam Report dated Jul. 11, 2011 for Mexican Patent Application No. MX/a/2009/004811.
Mexican Notice of Allowance dated Sep. 2, 2011 for Mexican Patent Application No. MX/a/2009/005751.
Document Title: Complaint for Patent Infringement [Jury Demand]; Case Title: *VoIp-Pal.Com, Inc., a Nevada corporation, Plaintiff*, v. *Verizon Wireless Services, LLC, a Delaware limited liability corporation; Verizon Communications, Inc., a Delaware corporation; AT&T, Inc., a Delaware corporation; AT&T Corp., a Delaware corporation*; and Does I through X, inclusive, Defendants; Case No. 2:16-CV-00271; Court: United States District Court District of Nevada. Attachments: Table of Exhibits; Exhibit A; Exhibit B; Exhibit C; Exhibit D; Exhibit E; Chart 1 to Exhibit E; Chart 2 to Exhibit E; Chart 3 to Exhibit E; Chart 4 to Exhibit E; Chart 5 to Exhibit E; Chart 6 to Exhibit E; Exhibit F; Chart 1 to Exhibit F; Chart 2 to Exhibit F; Chart 3 to Exhibit F; Chart 4 to Exhibit F; Chart 5 to Exhibit F; Chart 6 to Exhibit F; Exhibit G; Exhibit H; and Addendum 1 to Exhibit H.
Document Title: Complaint for Patent Infringement [Jury Demand]; Case Title: *VoIp-Pal.Com, Inc., a Nevada corporation, Plaintiff*, v. *Apple, Inc., a California corporation*; Defendants; Case No. 2:16-CV-00260; Court: United States District Court District Attachments: Table of Exhibits; Exhibit A; Exhibit B; Exhibit C; Exhibit D; Chart 1 to Exhibit D; Chart 2 to Exhibit D; Chart 3 to Exhibit D; Chart 4 to Exhibit D; Exhibit E; Exhibit F; and Addendum 1 to Exhibit F.
Letter dated Nov. 30, 2015, from VoIP-Pal.com Inc. giving notice and inviting the company listed herein below to contact VoIP-Pal.com about U.S. Pat. No. 9,179,005 and 8,542,815 and related patents listed in the accompanying Attachment A. Sent to the following company: Apple Inc. in the U.S.
Letter dated Dec. 1, 2015, from VoIP-Pal.com Inc. giving notice and inviting the company listed herein below to contact VoIP-Pal.com about U.S. Pat. No. 9,179,005 and 8,542,815 and related patents listed in the accompanying Attachment A. Sent to the following company: Verizon Communications in the U.S.
Letters dated Dec. 18, 2015, from VoIP-Pal.com Inc. giving notice and inviting the companies listed herein below to contact VoIP-Pal.com about U.S. Pat. No. 9,179,005 and 8,542,815 and related patents listed in the accompanying Attachment A. (Please Note: Attachment A is attached here only to the first letter.) Sent to the following companies: Airtel in India; Alcatel-Lucent in France; Avaya Inc. in the U.S.; AT&T in the U.S.; Blackberry in Canada; Cable One in the U.S.; CenturyLink in the U.S.; Charter Communications in the U.S.; Cisco Systems in the U.S.; Comcast in the U.S.; Cox Communications in the U.S.; Cricket Wireless in the U.S.; Facebook in the U.S.; Freedom Pop in the U.S.; Frontier Communications in the U.S.; Google Inc. in the U.S.; HP in the U.S.; Juniper Networks in the U.S.; LoopPay, Inc. in the U.S.; Magic Jack in the U.S.; MetroPCS in the U.S.; Ooma in the U.S.; PayPal in the U.S.; Republic Wireless in the U.S.; Rok Mobile in the U.S.; Samsung Electronics—America in the U.S.; ShoreTel, Inc. in the U.S.;.
Sent to the following companies: Letters dated Jan. 4, 2016, from VoIP-Pal.com Inc. giving notice and inviting the companies listed herein below to contact VoIP-Pal.com about U.S. Patents 9,179,005 and 8,542,815 and related patents listed in the accompanying Attachment A. (Please Note: Attachment A is attached here only to the first letter.) Rogers Communications Inc. in Canada; Shaw Cable in Canada; Walmart in Alaska; and WIND Mobile in Canada.
Letters dated Jan. 21, 2016, from VoIP-Pal.com Inc. giving notice and inviting the companies listed herein below to contact VoIP-Pal.com about U.S. Patents 9, 179,005 and 8,542,815 and related patents listed in the accompanying Attachment A. (Please Note: Attachment A is attached here only to the first letter.) Sent to the following companies: Alibaba (China) Co., Ltd in China; Comwave Telecommunications in Canada; and Intel in the U.S.
Letters dated Feb. 2, 2016, from VoIP-Pal.com Inc. giving notice and inviting the companies listed herein below to contact VoIP-Pal.com about U.S. Patents 9, 179,005 and 8,542,815 and related patents listed in the accompanying Attachment A. (Please Note: Attachment A is attached here only to the first letter.) Sent to the following companies: Netflix Inc. in the U.S.; Skype Technologies in the U.S.; and WhatsApp Inc. in the U.S.
Document Title: Petition for Inter Partes Review of U.S. Pat. No. 8,542,815; United States Patent and Trademark Office; Before the Patent Trial and Appeal Board; Unified Patents Inc., Petitioner v. Voip-Pal.Com Inc., Patent Owner; IPR2016-01082; Patent 8,542,815; Producing Routing Messages for Voice Over IP Communications; Dated May 24, 2016. 64 sheets.
Document Title: Declaration of Michael Caloyannides; United States Patent and Trademark Office; Before the Patent Trial and Appeal Board; Unifiedpatents Inc., Petitioner v. Voip-Pal.Com Inc., Patent Owner; IPR2016-01082; Patent 8,542,815; Producing Routing Messages for Voice Over IP Communications; Signed May 23, 2016; Filed May 24, 2016. 84 sheets.
Document Title: Public Switched Telephone Networks: A Network Analysis of Emerging Networks; Daniel Livengood, Jijun Lin and Chintan Vaishnav; Engineering Systems Division; Massachusetts Institute of Technology; Submitted May 16, 2006; To Dan Whitney, Joel Moses and Chris Magee. 27 sheets.
Document Title: A Brief History of VoIP; Document One—The Past; Joe Hallock; joe@sitedifference.com; date on cover page:

(56) References Cited

OTHER PUBLICATIONS

Nov. 26, 2004; Evolution and Trends in Digital Media Technologies—COM 538; Masters of Communication in Digital Media; University of Washington. 17 sheets.
Document Title: Petitioner's Voluntary Interrogatory Responses; United States Patent and Trademark Office; Before the Patent Trial and Appeal Board; *Unified Patents Inc., Petitioner* v. *VoIP-Pal.Com Inc.*, Patent Owner; IPR20161082; U.S. Pat. No. 8,542,815; Producing Routing Messages for Voice Over IP Communications; Signed and Filed not later than May 24, 2016. 8 sheets.
Document Title: VoIP-PAL, The World is Calling!, "Over $7 Billion in Lawsuits File by *Voip-Pal.com Inc.* vs *Apple, Verizon and AT&T* for Various Patent Infringements," Business Wire@, A Berkshire Hathaway Company, Feb. 11, 2016. 2 sheets.
Document Title: United States Patent and Trademark Office; Before the Patent Trial and Appeal Board; *Apple Inc., Petitioner* v. *Voip-Pal.Com Inc.*, Patent Owner; Case No. TBD, U.S. Pat. No. 9,179,005; Petition for Inter Partes Review of U.S. Pat. No. 9,179,005; Dated Jun. 15, 2016. 70 sheets.
Document Title: in the United States Patent and Trademark Office; Petition for Inter Partes Review Pursuant To 37 C.F.R. §42.100 Et Seq.; In re U.S. Pat. No. 9,179,005; Currently in Litigation Styled: *VoIP-Pal.com, Inc.* v. *Apple Inc.*, Case No. 2:16-cv-00260-RFB-VCF; Issued: Nov. 3, 2015; Application Filed: Aug. 13, 2013; Applicant: Clay Perreault, et al.; Title: Producing Routing Messages for Voice Over IP Communications; Declaration of Henry H. Houh, PhD; Signed Jun. 14, 2016. 143 sheets.
Document Title: United States Patent and Trademark Office; Before the Patent Trial and Appeal Board; *Apple Inc., Petitioner* v. *Voip-Pal.Com Inc.*, Patent Owner; Case No. Tbd, U.S. Pat. No. 8,542,815; Petition for Inter Partes Review of U.S. Pat. No. 8,542,815; Dated Jun. 15, 2016. 67 sheets.
Document Title: in the United States Patent and Trademark Office; Petition for Inter Partes Review Pursuant To 37 C.F.R. §42.100 Et Seq .; In re U.S. Pat. No. 8,542,815; Currently in Litigation Styled: *VoIP-Pal.com, Inc.* v. *Apple Inc.*, Case No. 2:16-cv-00260-RFB-VCF; Issued: Sep. 24, 2013; Application Filed: Nov. 1, 2007; Applicant: Clay Perreault, et al.; Title: Producing Routing Messages for Voice Over IP Communications; Declaration of Henry H. Houh, PhD; Signed Jun. 14, 2016. 143 sheets.
Complaint for Patent Infringement, United States District Court, District of Nevada, Case No. 2:16-cv-2338, *Voip-Pal.Com, Inc., a Nevada corporation, Plaintiff* v. *Twitter, Inc., a California corporation, Defendant*, Filed Oct. 6, 2016, 8 pages.
Civil Docket for Case #: 2:16-cv-02338-RFB-CWH, United States District Court, District of Nevada (Las Vegas), *Voip-Pal.com, Inc.* v. *Twitter, Inc.*, Date Filed: Oct. 6, 2016, 2 pages.
Table of Exhibits, Case 2:16-cv-02338-RFB-CWH, Filed Oct. 6, 2016, 1 page.
Exhibit A, Case 2:16-cv-02338-RFB-CWH, Filed Oct. 6, 2016, U.S. Pat. No. 8,542,815 B2, Issued Sep. 24, 2013, to Clay Perrault et al., 60 pages.
Exhibit B, Case 2:16-cv-02338-RFB-CWH, Filed Oct. 6, 2016, U.S. Pat. No. 9,179,005 B2, Issued Nov. 3, 2015, to Clay Perrault et al., 63 pages.
Exhibit C, Case 2:16-cv-02338-RFB-CWH, Filed Oct. 6, 2016, Letter dated Dec. 18, 2015 giving notice of U.S. Pat. No. 8,542,815 B2; 9,179,005 B2; and related Patents listed in Attachment A, 4 pages.
Exhibit D, Case 2:16-cv-02338-RFB-CWH, Filed Oct. 6, 2016, Asserted Claims and Infringement Conditions, United States District Court, District of Nevada, *Voip-Pal.Com, Inc., a Nevada corporation, Plaintiff* v. *Twitter, Inc., a California corporation, Defendants*, 6 pages.
Chart 1 to Exhibit D, Case 2:16-cv-02338-RFB-CWH, Filed Oct. 6, 2016, Chart 1, Asserted Claims and Infringement Conditions Concerning U.S. Pat. No. 8,542,815, United States District Court, District of Nevada, *Voip-Pal.Com, Inc., a Nevada corporation, Plaintiff* v. *Twitter, Inc., a California corporation, Defendants*, 20 pages.
Chart 2 to Exhibit D, Case 2:16-cv-02338-RFB-CWH, Filed Oct. 6, 16, Chart 2, Asserted Claims and Infringement Conditions Concerning U.S. Pat. No. 9,179,005, United States District Court, District of Nevada, *Voip-Pal.Com, Inc., a Nevada corporation, Plaintiff* v. *Twitter, Inc., a California corporation, Defendants*, 28 pages.
Exhibit E, Case 2:16-cv-02338-RFB-CWH, Filed Oct. 6, 2016, VPLM Active U.S. Patent Matters as of Oct. 1, 2016, 2 pages.
Exhibit F, Case 2:16-cv-02338-RFB-CWH, Filed Oct. 6, 16, Twitter Royalty Monetization Analysis Overview, 4 pages.
Patent Owner's Preliminary Response, Case No. IPR2016-01082, U.S. Pat. No. 8,542,815, *Unified Patents Inc., Petitioner,* v. *Voip-Pal.Com Inc., Patent Owner*, Filing Date: Aug. 26, 2016, 80 pages.
Voip-Pal.com, Inc. Exhibit 2001, Comparison of portions of Petition with portions of Declaration, IPR2016-01082, *Unified Patents* v. *Voip-Pal*, Filing Date: Aug. 26, 2016, 9 pages.
Patent Owner's Preliminary Response To Petition for Inter Partes Review, Case No. IPR2016-01201, U.S. Pat. No. 8,542,815, *Apple Inc., Petitioner,* v. *Voip-Pal.Com Inc., Patent Owner*, Filing Date: Sep. 19, 2016, 74 pages.
Voip-Pal.com, Inc. Exhibit 2001, Comparison of Petition (Ground 1) with Petition (Ground 2), IPR2016-01201, *Apple* v. *Voip-Pal*, Filing Date: Sep. 19, 2016, 19 pages.
Patent Owner's Preliminary Response To Petition for Inter Partes Review, Case No. IPR2016-01198, U.S. Pat. No. 9,179,005, *Apple Inc., Petitioner,* v. *Voip-Pal.Com Inc., Patent Owner*, Filing Date: Sep. 21, 2016, 74 pages.
Voip-Pal.com, Inc. Exhibit 2001, Comparison of Petition (Ground 1) with Petition (Ground 2), IPR2016-01198, *Apple* v. *Voip-Pal*, Filing Date: Sep. 21, 2016, 21 pages.
Decision: Denying Institution of Inter Partes Review, 37 C.F.R. § 42.108, United States Patent and Trademark Office, Before the Patent Trial and Appeal Board, *Unified Patents Inc., Petitioner* v. *Voip-Pal.Com Inc., Patent Owner*, Case IPR2016-01082, U.S. Pat. No. 8,542,815 B2, Paper 8, Entered: Nov. 18, 2016.
Decision: Institution of Inter Partes Review, 37 C.F.R. § 42.108, United States Patent and Trademark Office, Before the Patent Trial and Appeal Board, *Apple Inc., Petitioner* v. *Voip-Pal.Com Inc., Patent Owner*, Case IPR2016-01201, U.S. Pat. No. 8,542,815 B2, Paper 6, Entered: Nov. 21, 2016.
Decision: Institution of Inter Partes Review, 37 C.F.R. § 42.108, United States Patent and Trademark Office, Before the Patent Trial and Appeal Board, *Apple Inc., Petitioner* v. *Voip-Pal.Com Inc., Patent Owner*, Case IPR2016-01198, U.S. Pat. No. 9,179,005 B2, Paper 6, Entered: Nov. 21, 2016.
Scheduling Order: United States Patent and Trademark Office, Before the Patent Trial and Appeal Board, *Apple Inc., Petitioner* v. *Voip-Pal.Com Inc., Patent Owner*, Cases IPR2016-01201, IPR2016-01198, U.S. Pat. No. 8,542,815 B2, U.S. Pat. No. 9,179,005 B2, Paper 7, Entered: Nov. 21, 2016.
Patent Owner Response To Petition, *Apple Inc., Petitioner,* v. *Voip-Pal.Com, Inc., Patent Owner*, Case No. IPR2016-01201, U.S. Pat. No. 8,542,815, United States Patent and Trademark Office, Before the Patent Trial and Appeal Board, Filed: Feb. 10, 2017, 76 pages.
Patent Owner Updated Exhibit List, *Apple Inc., Petitioner,* v. *Voip-Pal.Com, Inc., Patent Owner*, Case No. IPR2016-01201, U.S. Pat. No. 8,542,815, United States Patent and Trademark Office, Before the Patent Trial and Appeal Board, Filed: Feb. 10, 2017, 6 pages.
Voip-Pal Ex. 2002, IPR2016-01201, "Declaration of Ryan Thomas in Support of Pro Hac Vice Motion," *Apple Inc., Petitioner,* v. *Voip-Pal.Com, Inc., Patent Owner*, Case No. IPR2016- 01201, U.S. Pat. No. 8,542,815, United States Patent and Trademark Office, Before the Patent Trial and Appeal Board, Dated: Jan. 20, 2017, 4 pages.
Voip-Pal Ex. 2003, IPR2016-01201, "Technical Review of Digifonica VoIP System," DIGIFONICA,Global Telephone Solutions, Author: John Rutter, Stuart Gare, Version V0.7 (Draft), Date: May 7, 2005, 35 pages.
Voip-Pal Ex. 2004, IPR2016-01201, Memo—"Subject: Smart 421 Contract signed and Faxed," From: Clay S. Perreault, Date: Jun. 6, 2005, 8:53 AM, To: Steve Nicholson, et al., 2 pages.

(56) References Cited

OTHER PUBLICATIONS

Voip-Pal Ex. 2005, IPR2016-01201, Memo—"Subject: Digifonica TEchnology review," From: Clay Perreault, Date: Jun. 6, 2005, 5:37 PM; To: John Rutter, et al., 5 pages.
Voip-Pal Ex. 2006, IPR2016-01201, Memo—"Subject: Re: Sample code for review Next document upload complete," From: Clay Perreault, Date: Jun. 15, 2005, 3:28 PM, To: John Rutter, et al., 3 pages.
Voip-Pal Ex. 2007, IPR2016-01201, DigiFonica International Inc Memo—"[Fwd: Digifonica Technical Review—draft report]," From Clay Perreault, To: Rod Thomson, et al., Tue, Jul. 5, 2005 at 4:45 PM, 2 pages.
Voip-Pal Ex. 2008, IPR2016-01201, John Rutter—"Declaration in Support Patent Owner Response To Inter Partes Petition," *Apple Inc., Petitioner,* v. *Voip-Pal.Com, Inc., PatentOwner*, Case No. IPR2016-01201, U.S. Pat. No. 8,542,815, United States Patent and Trademark Office, Before the Patent Trial and Appeal Board, Dated: Jan. 31, 2017, 4 pages.
Voip-Pal Ex. 2009, IPR2016-01201, Stuart Gare—"Declaration in Support Patent Owner Response To Inter Partes Petition," *Apple Inc., Petitioner,* v. *Voip-Pal.Com, Inc., Patent Owner*, Case No. IPR2016-01201, U.S. Pat. No. 8,542,815, United States Patent and Trademark Office, Before the Patent Trial and Appeal Board, Dated: Feb. 2, 2017, 4 pages.
Voip-Pal Ex. 2010, IPR2016-01201, Pentti Kalevi Huttunen—"Declaration in Support Patent Owner Response To Inter Partes Petition," *Apple Inc., Petitioner,* v. *Voip-Pal.Com,Inc.*, Patent Owner, Case No. IPR2016-01201, U.S. Pat. No. 8,542,815, United States Patent and Trademark Office, Before the Patent Trial and Appeal Board, Dated: Feb. 3, 2017, 4 pages.
Voip-Pal Ex. 2011, IPR2016-01201, Ryan Purita—"Declaration in Support Patent Owner Response To Inter Partes Petition," *Apple Inc., Petitioner,* v. *Voip-Pal.Com, Inc., Patent Owner*, Case No. IPR2016-01201, U.S. Pat. No. 8,542,815, United States Patent and Trademark Office, Before the Patent Trial and Appeal Board, Dated: Jan. 31, 2017, 3 pages.
Voip-Pal Ex. 2012, IPR2016-01201, Johan Emil Viktor Björsell—"Declaration in Support Patent Owner Response To Inter Partes Petition," *Apple Inc., Petitioner,* v. *Voip-Pal.Com, Inc., Patent Owner*, Case No. IPR2016-01201, U.S. Pat. No. 8,542,815, United States Patent and Trademark Office, Before the Patent Trial and Appeal Board, Dated: Feb. 9, 2017, 9 pages.
Voip-Pal Ex. 2013, IPR2016-01201, Clay Perreault—"Declaration in Support Patent Owner Response To Inter Partes Petition," *Apple Inc., Petitioner,* v. *Voip-Pal.Com, Inc., Patent Owner*, Case No. IPR2016-01201, U.S. Pat. No. 8,542,815, United States Patent and Trademark Office, Before the Patent Trial and Appeal Board, Dated: Feb. 8, 2017, 6 pages.
Voip-Pal Ex. 2014, IPR2016-01201, RBR Source Code, Version 361, "call_e164.class.php RBR Version 361, Jun. 6, 2005 09:22:59," 45 pages.
Voip-Pal Ex. 2015, IPR2016-01201, RBR Source Code Log for Trunk Directory, "r1879 | cdelalande | Oct. 31, 2006 17:07:46-0800 (Tue, Oct. 31, 2006) | 3 lines," 56 pages.
Voip-Pal Ex. 2016, IPR2016-01201, William Henry Mangione-Smith—"Declaration in Support Patent Owner Response To Inter Partes Petition," *Apple Inc., Petitioner,* v. *Voip- Pal.Com, Inc., Patent Owner*, Case No. IPR2016-01201, U.S. Pat. No. 8,542,815, United States Patent and Trademark Office, Before the Patent Trial and Appeal Board, Dated: Feb. 10, 2017, 82 pages.
Voip-Pal Ex. 2017, IPR2016-01201, DF DigiFonica International Inc Memo—"notes from your presentation, 1 message" From Konstantin Kropivny, To: Emil Björsell, Tue, Jun. 14, 2005 at 7:33PM, 4 pages.
Voip-Pal Ex. 2018, IPR2016-01201, David Terry—"Declaration in Support Patent Owner Response To Inter Partes Petition," *Apple Inc., Petitioner,* v. *Voip-Pal.Com, Inc., PatentOwner*, Case No. IPR2016-01201, U.S. Pat. No. 8,542,815, United States Patent and Trademark Office, Before the Patent Trial and Appeal Board, Dated: Feb. 8, 2017, 5 pages.

Voip-Pal Ex. 2019, IPR2016-01201, DF DigiFonica International Inc Memo—"Software release 10:30 am PST—11:00am PST for Aug. 25, 2005. 1 message" From Samantha Edwards, To: everyone@digifonica.com, Wed., Aug. 24, 2005 at 4:02 PM, 8 pages.
Voip-Pal Ex. 2020, IPR2016-01201, "Next Generation Networks—A Migration Path Digifonica Voice Over IP Technologies. Technology Overview, DRAFT Jun. 3, 2005, Not for Distribution," by Clay S Perreault, CEO / CTO, Digifonica International Ltd, Gibraltar, 45 pages.
Voip-Pal Ex. 2021, IPR2016-01201, DF DigiFonica International Inc Memo—"Software roll out for supernodes.:: Salm Rev 341, RBR Rev 341 added, 1 message" Fuad A. To: E. Björsell, Tue, May 31, 2005 at 1:13 PM, 1 page.
Voip-Pal Ex. 2022, IPR2016-01201, DF DigiFonica International Inc Memo—"Salm Rev 341, RBR Rev 341, 2 messages" Emil Björsell To: Fuad, et al., Tue, May 31, 2005 at 2:38 and 2:44 PM, 1 page.
Voip-Pal Ex. 2023, IPR2016-01201, DF DigiFonica International Inc Memo—"Software roll out for supernodes.:: RBR Roll out Rev 353 added, 1 message" Fuad A. To: E. Björsell, Thu, Jun. 2, 2005 at 1:12 PM, 1 page.
Voip-Pal Ex. 2024, IPR2016-01201, DF DigiFonica International Inc Memo—"Software roll out for supernodes.:: RBR Roll out Rev 358 added, 1 message" Fuad A. To: E. Björsell, Sun, Jun. 5, 2005 at 1:18 PM, 1 page.
Voip-Pal Ex. 2025, IPR2016-01201, DF DigiFonica International Inc Memo—"Software roll out for supernodes.:: RBR Roll out Rev 361 updated, 1 message" Fuad A. To: E. Björsell, Mon., Jun. 6, 2005 at 9:26 AM, 1 page.
Voip-Pal Ex. 2026, IPR2016-01201, DF DigiFonica International Inc Memo—"RBR Roll out Rev 361, 1 message" David Terry To: Fuad, et al., Mon., Jun. 6, 2005 at 9:33 AM, 1 page.
Voip-Pal Ex. 2027, IPR2016-01201, DF DigiFonica International Inc Memo—"RBR Roll out Rev 361, 1 message" Emil Björsell To: Fuad, et al., Mon., Jun. 6, 2005 at 11:33 AM, 1 page.
Voip-Pal Ex. 2030, IPR2016-01201, DF DigiFonica International Inc Memo—"Software roll out for supernodes.:: RBR Rev 541 updated, 1 message" Fuad A. To: E. Björsell, Thu, Aug. 4, 2005 at 11:57 AM, 1 page.
Voip-Pal Ex. 2031, IPR2016-01201, DF DigiFonica International Inc Memo—"RBR Rev 541, 1 message" David Terry To: Fuad, et al., Thu, Aug. 4, 2005 at 1:58 PM, 1 page.
Voip-Pal Ex. 2032, IPR2016-01201, DF DigiFonica International Inc Memo—"RBR Rev 541, 1 message" Emil Björsell To: Fuad, et al., Thu, Aug. 4, 2005 at 3:59 PM, 1 page.
Voip-Pal Ex. 2033, IPR2016-01201, DF DigiFonica International Inc Memo—"Software roll out for supernodes.:: RBR Roll out Rev 554 added, 1 message" Fuad A. To: Emil Björsell, Mon, Aug. 8, 2005 at 10:55 AM, 1 page.
Voip-Pal Ex. 2034, IPR2016-01201, DF DigiFonica International Inc Memo—"RBR Roll out Rev 554, 2 messages" David Terry To: Fuad, et al., Mon, Aug. 8, 2005 at 11:48 AM and 12:00 PM, 1 page.
Voip-Pal Ex. 2035, IPR2016-01201, DF DigiFonica International Inc Memo—"RBR Roll out Rev 554, 1 message" Emil Björsell To: Fuad, et al., Mon, Aug. 8, 2005 at 12:09 PM, 1 page.
Voip-Pal Ex. 2036, IPR2016-01201, DF DigiFonica International Inc Memo—"Digifonica : RBR and Salma Deployment," Samantha Edwards To: everyone@digifonica.com, Mon, Aug. 8, 2005 at 4:12 PM, 4 pages.
Voip-Pal Ex. 2042, IPR2016-01201, DF DigiFonica International Inc Memo—"RBR Roll out Rev 693 == >694, 1 message" Chris Huff To: Fuad, et al., Tue, Aug. 23, 2005 at 1:33 PM, 1 page.
Voip-Pal Ex. 2043, IPR2016-01201, "Deposition of Henry H. Houh, Ph.D., vol. I, Taken On Behalf of the Patent Owner," *Apple Inc., Petitioner,* v. *Voip-Pal.Com, Inc., Patent Owner*, Case No. IPR2016-01201, U.S. Pat. No. 8,542,815, United States Patent and Trademark Office, Before the Patent Trial and Appeal Board, Dated: Jan. 25, 2017, 128 pages.
Voip-Pal Ex. 2044, IPR2016-01201, "Deposition of Henry H. Houh, Ph.D., vol. II, Taken On Behalf of the Patent Owner," *Apple Inc., Petitioner,* v. *Voip-Pal.Com, Inc., PatentOwner*, Case No. IPR2016-

(56) References Cited

OTHER PUBLICATIONS

01201, U.S. Pat. No. 8,542,815, United States Patent and Trademark Office, Before the Patent Trial and Appeal Board, Dated: Jan. 26, 2017, 158 pages.
Voip-Pal Ex. 2045, IPR2016-01201, Curriculum Vitae of William Henry Mangione-Smith, Ph. D., 23 pages.
Voip-Pal Ex. 2046, IPR2016-01201, U.S. Pat. No. 3,725,596, Issued Apr. 3, 1973, Rodney Robert Maxon et al., 18 pages.
Voip-Pal Ex. 2047, IPR2016-01201, "Merlin@ Communications System, Centrex/PBS Connection," Lucent Technologies, Bell Labs Innovations, @ 1984 AT&T, 999-500-138 IS, Issue 1, Mar. 1985, 26 pages.
Voip-Pal Ex. 2048, IPR2016-01201, "Telephone Features," Quick Reference Guide, Definity, Rockefeller Group, Telecommunications Services, Inc., 2000, 2 pages.
Voip-Pal Ex. 2049, IPR2016-01201, Valdar, Andy, Understanding Telecommunications Networks, @2006 The Institution of Engineering and Technology, London, UK, Title page, copyright page, pp. 38-39.
Voip-Pal Ex. 2050, IPR2016-01201, Horak, Ray, "Webster's New World@ Telecom Dictionary," @ 2008 by Wiley Publishing, Inc., Indianapolis, Indiana, Title page, copyright page, p. 133.
Patent Owner Response To Petition, *Apple Inc., Petitioner, v. Voip-Pal.Com, Inc., Patent Owner*, Case No. IPR2016-01198, U.S. Pat. No. 9,179,005, United States Patent and Trademark Office, Before the Patent Trial and Appeal Board, Filed: Feb. 10, 2017, 78 pages.
Patent Owner Updated Exhibit List, *Apple Inc., Petitioner, v. Voip-Pal.Com, Inc., Patent Owner*, Case No. IPR2016-01198, U.S. Pat. 9,179,005, United States Patent and Trademark Office, Before the Patent Trial and Appeal Board, Filed: Feb. 10, 2017, 6 pages.
Voip-Pal Ex. 2002, IPR2016-01198, "Declaration of Ryan Thomas in Support of Pro Hac Vice Motion," *Apple Inc., Petitioner, v. Voip-Pal.Com, Inc., Patent Owner*, Case No. IPR2016-01198, U.S. Pat. No. 9,179,005, United States Patent and Trademark Office, Before the Patent Trial and Appeal Board, Dated: Jan. 20, 2017, 4 pages.
Voip-Pal Ex. 2003, IPR2016-01198, "Technical Review of Digifonica VoIP System," DIGIFONICA, Global Telephone Solutions, Author: John Rutter, Stuart Gare, Version V0.7 (Draft), Date: May 7, 2005, 35 pages.
Voip-Pal Ex. 2004, IPR2016-01198, Memo—"Subject: Smart 421 Contract signed and Faxed," From: Clay S. Perreault, Date: Jun. 6, 05, 8:53 AM, To: Steve Nicholson, et al., 2 pages.
Voip-Pal Ex. 2005, IPR2016-01198, Memo—"Subject: Digifonica TEchnology review," From: Clay Perreault, Date: Jun. 6, 2005, 5:37 PM; To: John Rutter, et al., 5 pages.
Voip-Pal Ex. 2006, IPR2016-01198, Memo—"Subject: Re: Sample code for review Next document upload complete," From: Clay Perreault, Date: Jun. 15, 05, 3:28 PM, To: John Rutter, et al., 3 pages.
Voip-Pal Ex. 2007, IPR2016-01198, DigiFonica International Inc Memo—"[Fwd: Digifonica Technical Review—draft report]," From Clay Perreault, To: Rod Thomson, et al., Tue, Jul. 5, 2005 at 4:45 PM, 2 pages.
Voip-Pal Ex. 2008, IPR2016-01198, John Rutter—"Declaration in Support Patent Owner Response To Inter Partes Petition," *Apple Inc., Petitioner, v. Voip-Pal.Com, Inc., Patent Owner*, Case No. IPR2016-01198, U.S. Pat. No. 9,179,005, United States Patent and Trademark Office, Before the Patent Trial and Appeal Board, Dated: Jan. 31, 2017, 4 pages.
Voip-Pal Ex. 2009, IPR2016-01198, Stuart Gare—"Declaration in Support Patent Owner Response To Inter Partes Petition," *Apple Inc., Petitioner, v. Voip-Pal.Com, Inc., Patent Owner*, Case No. IPR2016-01198, U.S. Pat. No. 9,179,005, United States Patent and Trademark Office, Before the Patent Trial and Appeal Board, Dated: Feb. 2, 2017, 4 pages.
Voip-Pal Ex. 2010, IPR2016-01198, Pentti Kalevi Huttunen—"Declaration in Support Patent Owner Response To Inter Partes Petition," *Apple Inc., Petitioner, v. Voip-Pal.Com, Inc., Patent Owner*, Case No. IPR2016-01198, U.S. Pat. No. 9,179,005, United States Patent and Trademark Office, Before the Patent Trial and Appeal Board, Dated: Feb. 3, 2017, 4 pages.
Voip-Pal Ex. 2011, IPR2016-01198, Ryan Purita—"Declaration in Support Patent Owner Response To Inter Partes Petition," *Apple Inc., Petitioner, v. Voip-Pal.Com, Inc., Patent Owner*, Case No. IPR2016-01198, U.S. Pat. No. 9,179,005, United States Patent and Trademark Office, Before the Patent Trial and Appeal Board, Dated: Jan. 31, 2017, 3 pages.
Voip-Pal Ex. 2012, IPR2016-01198, Johan Emil Viktor Björsell—"Declaration in Support Patent Owner Response To Inter Partes Petition," *Apple Inc., Petitioner, v. Voip-Pal.Com, Inc., Patent Owner*, Case No. IPR2016-01198, U.S. Pat. No. 9,179,005, United States Patent and Trademark Office, Before the Patent Trial and Appeal Board, Dated: Feb. 9, 2017, 9 pages.
Voip-Pal Ex. 2013, IPR2016-01198, Clay Perreault—"Declaration in Support Patent Owner Response To Inter Partes Petition," *Apple Inc., Petitioner, v. Voip-Pal.Com, Inc., Patent Owner*, Case No. IPR2016-01198, U.S. Pat. No. 9,179,005, United States Patent and Trademark Office, Before the Patent Trial and Appeal Board, Dated: Feb. 8, 2017, 6 pages.
Voip-Pal Ex. 2014, IPR2016-01198, RBR Source Code, Version 361, "call_e164.class.php RBR Version 361, Jun. 6, 2005 09:22:59," 45 pages.
Voip-Pal Ex. 2015, IPR2016-01198, RBR Source Code Log for Trunk Directory, "r1879 | cdelalande | Oct. 31, 2006 17:07:46-0800 (Tue, Oct. 31, 2006) | 3 lines," 56 pages.
Voip-Pal Ex. 2016, IPR2016-01198, William Henry Mangione-Smith—"Declaration in Support Patent Owner Response To Inter Partes Petition," *Apple Inc., Petitioner, v. Voip-Pal.Com, Inc., Patent Owner*, Case No. IPR2016-01198, U.S. Pat. No. 9,179,005, United States Patent and Trademark Office, Before the Patent Trial and Appeal Board, Dated: Feb. 10, 2017, 96 pages.
Voip-Pal Ex. 2017, IPR2016-01198, DF DigiFonica International Inc Memo—"notes from your presentation, 1 message" From Konstantin Kropivny, To: Emil Björsell, Tue, Jun. 14, 2005 at 7:33PM, 4 pages.
Voip-Pal Ex. 2018, IPR2016-01198, David Terry—"Declaration in Support Patent Owner Response To Inter Partes Petition," *Apple Inc., Petitioner, v. Voip-Pal.Com, Inc., Patent Owner*, Case No. IPR2016-01198, U.S. Pat. No. 9,179,005, United States Patent and Trademark Office, Before the Patent Trial and Appeal Board, Dated: Feb. 8, 2017, 5 pages.
Voip-Pal Ex. 2019, IPR2016-01198, DF DigiFonica International Inc Memo—"Software release 10:30 am PST-11:00am PST for Aug. 25, 2005. 1 message" From Samantha Edwards, To: everyone@digifonica.com, Wed., Aug. 24, 2005 at 4:02 PM, 8 pages.
Voip-Pal Ex. 2020, IPR2016-01198, "Next Generation Networks—A Migration Path Digifonica VoiceOver IP Technologies. Technology Overview, DRAFT Jun. 3, 2005, Not for Distribution," by Clay S Perreault, CEO / CTO, Digifonica International Ltd, Gibraltar, 45 pages.
Voip-Pal Ex. 2021, IPR2016-01198, DF DigiFonica International Inc Memo—"Software roll out for supernodes.:: Salm Rev 341, RBR Rev 341 added, 1 message" Fuad A. To: E. Björsell, Tue, May 31, 2005 at 1:13 PM, 1 page.
Voip-Pal Ex. 2022, IPR2016-01198, DF DigiFonica International Inc Memo—"Salm Rev 341, RBR Rev 341, 2 messages" Emil Bjorsell To: Fuad, et al., Tue, May 31, 2005 at 2:38 and 2:44 PM, 1 page.
Voip-Pal Ex. 2023, IPR2016-01198, DF DigiFonica International Inc Memo—"Software roll out for supernodes.:: RBR Roll out Rev 353 added, 1 message" Fuad A. To: E. Björsell, Thu, Jun. 2, 2005 at 1:12 PM, 1 page.
Voip-Pal Ex. 2024, IPR2016-01198, DF DigiFonica International Inc Memo—"Software roll out for supernodes.:: RBR Roll out Rev 358 added, 1 message" Fuad A. To: E. Björsell, Sun, Jun. 5, 2005 at 1:18 PM, 1 page.
Voip-Pal Ex. 2025, IPR2016-01198, DF DigiFonica International Inc Memo—"Software roll out for supernodes.:: RBR Roll out Rev 361 updated, 1 message" Fuad A. To: E. Björsell, Mon., Jun. 6, 2005 at 9:26 AM, 1 page.

(56) References Cited

OTHER PUBLICATIONS

Voip-Pal Ex. 2026, IPR2016-01198, DF DigiFonica International Inc Memo—"RBR Roll out Rev 361, 1 message" David Terry To: Fuad, et al., Mon., Jun. 6, 2005 at 9:33 AM, 1 page.
Voip-Pal Ex. 2027, IPR2016-01198, DF DigiFonica International Inc Memo—"RBR Roll out Rev 361, 1 message" Emil Björsell To: Fuad, et al., Mon., Jun. 6, 2005 at 11:33 AM, 1 page.
Voip-Pal Ex. 2030, IPR2016-01198, DF DigiFonica International Inc Memo—"Software roll out for supernodes.:: RBR Rev 541 updated, 1 message" Fuad A. To: E. Björsell, Thu, Aug. 4, 2005 at 11:57 AM, 1 page.
Voip-Pal Ex. 2031, IPR2016-01198, DF DigiFonica International Inc Memo—"RBR Rev 541, 1 message" David Terry To: Fuad, et al., Thu, Aug. 4, 2005 at 1:58 PM, 1 page.
Voip-Pal Ex. 2032, IPR2016-01198, DF DigiFonica International Inc Memo—"RBR Rev 541, 1 message" Emil Björsell To: Fuad, et al., Thu, Aug. 4, 2005 at 3:59 PM, 1 page.
Voip-Pal Ex. 2033, IPR2016-01198, DF DigiFonica International Inc Memo—"Software roll out for supernodes.:: RBR Roll out Rev 554 added, 1 message" Fuad A. To: Emil Björsell, Mon, Aug. 8, 2005 at 10:55 AM, 1 page.
Voip-Pal Ex. 2034, IPR2016-01198, DF DigiFonica International Inc Memo—"RBR Roll out Rev 554, 2 messages" David Terry To: Fuad, et al., Mon, Aug. 8, 2005 at 11:48 AM and 12:00 PM, 1 page.
Voip-Pal Ex. 2035, IPR2016-01198, DF DigiFonica International Inc Memo—"RBR Roll out Rev 554, 1 message" Emil Björsell To: Fuad, et al., Mon, Aug. 8, 2005 at 12:09 PM, 1 page.
Voip-Pal Ex. 2036, IPR2016-01198, DF DigiFonica International Inc Memo—"Digifonica : RBR andSalma Deployment," Samantha Edwards To: everyone@digifonica.com, Mon, Aug. 8, 2005 at 4:12 PM, 4 pages.
Voip-Pal Ex. 2042, IPR2016-01198, DF DigiFonica International Inc Memo—"RBR Roll out Rev 693 == >694, 1 message" Chris Huff To: Fuad, et al., Tue, Aug. 23, 2005 at 1:33 PM, 1 page.
Voip-Pal Ex. 2043, IPR2016-01198, "Deposition of Henry H. Houh, Ph.D., vol. I, Taken On Behalf of the Patent Owner," *Apple Inc., Petitioner,* v. *Voip-Pal.Com, Inc., Patent Owner*, Case No. IPR2016-01201, U.S. Pat. No. 8,542,815, United States Patent and Trademark Office, Before the Patent Trial and Appeal Board, Dated: Jan. 25, 2017, 128 pages.
Voip-Pal Ex. 2044, IPR2016-01198, "Deposition of Henry H. Houh, Ph.D., vol. II, Taken On Behalf of the Patent Owner," *Apple Inc., Petitioner,* v. *Voip-Pal.Com, Inc., Patent Owner*, Case No. IPR2016-01201, U.S. Pat. No. 8,542,815, United States Patent and Trademark Office, Before the Patent Trial and Appeal Board, Dated: Jan. 26, 2017, 158 pages.
Voip-Pal Ex. 2045, IPR2016-01198, Curriculum Vitae of William Henry Mangione-Smith, Ph. D., 23 pages.
Voip-Pal Ex. 2046, IPR2016-01198, U.S. Pat. No. 3,725,596, Issued Apr. 3, 1973, Rodney Robert Maxon et al., 18 pages.
Voip-Pal Ex. 2047, IPR2016-01198, "Merling Communications System, Centrex/Pbs Connection," Lucent Technologies, Bell Labs Innovations, @ 1984 AT&T, 999-500-138 IS, Issue 1, Mar. 1985, 26 pages.
Voip-Pal Ex. 2048, IPR2016-01198, "Telephone Features," Quick Reference Guide, Definity, Rockefeller Group, Telecommunications Services, Inc., 2000, 2 pages.
Voip-Pal Ex. 2049, IPR2016-01198, Valdar, Andy, Understanding Telecommunications Networks, @2006 The Institution of Engineering and Technology, London, UK, Title page, copyright page, pp. 38-39.
Voip-Pal Ex. 2050, IPR2016-01198, Horak, Ray, "Webster's New World@ Telecom Dictionary," @ 2008 by Wiley Publishing, Inc., Indianapolis, Indiana, Title page, copyright page, p. 133.
Document Title: United States Patent and Trademark Office; Before the Patent Trial and Appeal Board; *Apple Inc., Petitioner* v. *Voip-Pal.Com Inc., Patent Owner*; Case No. IPR2017-01399-815; U.S. Pat. No. 8,542,815; Petition for Inter Partes Review of U.S. Pat. No. 8,542,815; Dated May 9, 2017, 63 pages.

Petitioner Apple Inc. Exhibit 1003, Case No. IPR2017-01399-815; U.S. Pat. No. 8,542,815: U.S. Pat. No. 7,486,684 to Chu, et al., 59 pages.
Petitioner Apple Inc. Exhibit 1004, Case No. IPR2017-01399-815; U.S. Pat. No. 8,542,815: U.S. Pat. No. 6,760,324 to Scott, et al., 65 pages.
Petitioner Apple Inc. Exhibit 1005, Case No. IPR2017-01399-815; U.S. Pat. No. 8,542,815: Declaration of Henry H. Hough, PhD, 45 pages.
Petitioner Apple Inc. Exhibit 1006, Case No. IPR2017-01399-815; U.S. Pat. No. 8,542,815: U.S. Publication No. 2002/0122547 to Hinchey et al., 21 pages.
Document Title: United States Patent and Trademark Office; Before the Patent Trial and Appeal Board; *Apple Inc., Petitioner* v. *Patent of Voip-Pal.Com Inc., Patent Owner*; Case No. IPR2017-01398-005; U.S. Pat. No. 9,179,005; Petition for Inter Partes Review of U.S. Pat. No. 9,179,005; Dated May 9, 2017. 54 pages.
Petitioner Apple Inc. Exhibit 1006, Case No. IPR2017-01398-005; U.S. Pat. No. 9,179,005: U.S. Pat. No. 7,486,684 to Chu, et al., 59 pages.
Petitioner Apple Inc. Exhibit 1007, Case No. IPR2017-01398-005; U.S. Pat. No. 9,179,005: U.S. Pat. No. 6,760,324 to Scott, et al., 65 pages.
Petitioner Apple Inc. Exhibit 1008, Case No. IPR2017-01398-005; U.S. Pat. No. 9,179,005: Declaration of Henry H. Hough, PhD, 41 pages.
Petitioner Apple Inc. Exhibit 1009, Case No. IPR2017-01398-005; U.S. Pat. No. 9,179,005: U.S. Publication No. 2002/0122547 to Hinchey et al., 21 pages.
Document Title: in the United States Patent and Trademark Office; Before the Patent Trial and Appeal Board; *AT&T Services, Inc., Petitioner* v. *Digifonica (International) Limited Patent Owner*, Case No. IPR2017-01382; U.S. Pat. No. 8,542,815; Petition for Inter Partes Review of U.S. Pat. No. 8,542,815; Dated May 8, 2017, 84 pages.
Petitioner AT&T Services, Inc. EXHIBIT 1003, United States Patent and Trademark Office; Before the Patent Trial and Appeal Board; *AT&T Services, Inc., Petitioner* v. *Digifonica (International) Limited Patent Owner*, U.S. Pat. No. 8,542,815, Inter Partes Review No. IPR2017-01382; Declaration of James Bress in Support of Petition for Inter Partes Review of U.S. Pat. No. 8,542,815; with Appendices A through II, 2113 pages.
Petitioner AT&T Services, Inc. EXHIBIT 1003, Case No. IPR2017-01382; Appendix A, James R. Bress, Curriculum Vitae, 26 pages.
Petitioner AT&T Services, Inc. EXHIBIT 1003, Case No. IPR2017-01382; Appendix B, Chapter 5, Telecommunications Essentials, Lillian Goleniewski, @ 2002, 40 pages.
Petitioner AT&T Services, Inc. EXHIBIT 1003, Case No. IPR2017-01382; Appendix C, Chapter 11, Telecommunications Essentials, Lillian Goleniewski, @ 2002, 41 pages.
Petitioner AT&T Services, Inc. EXHIBIT 1003, Case No. IPR2017-01382; Appendix D, ITU-T Recommendation E.164 (May 1997), 27 pages.
Petitioner AT&T Services, Inc. EXHIBIT 1003, Case No. IPR2017-01382; Appendix E, Telcordia Notes on the Networks, SR-2275, Issue 4, Oct. 2000, pp. 3-Aug. 3, 14, 9 pages.
Petitioner AT&T Services, Inc. EXHIBIT 1003, Case No. IPR2017-01382; Appendix F, Chapter 4, Telecommunications Essentials, Lillian Goleniewski, @ 2002, pp. 99-100, 4 pages.
Petitioner AT&T Services, Inc. EXHIBIT 1003, Case No. IPR2017-01382; Appendix G, Telcordia Notes on the Networks, SR-2275, Issue 4, Oct. 2000, pp. 18-Jan. 18, 20, 22 pages.
Petitioner AT&T Services, Inc. EXHIBIT 1003, Case No. IPR2017-01382; Appendix H, Softswitch, Architecture for VoIP, Franklin D. Ohrtman, Jr., @ 2003, Chapter 2, 32 pages.
Petitioner AT&T Services, Inc. EXHIBIT 1003, Case No. IPR2017-01382; Appendix I, Telecommunications Act of 1996, 104th Congress of the U.S.A., Jan. 1996, 128 pages.
Petitioner AT&T Services, Inc. EXHIBIT 1003, Case No. IPR2017-01382; Appendix J, Perspectives on the AIN Architecture, Berman et al., IEEE Communications Magazine, Feb. 1992, 6 pages.

(56) References Cited

OTHER PUBLICATIONS

Petitioner AT&T Services, Inc. EXHIBIT 1003, Case No. IPR2017-01382; Appendix K, U.S. Pat. No. 7,907,714 B2, to Baniak et al., 21 pages.
Petitioner AT&T Services, Inc. EXHIBIT 1003, Case No. IPR2017-01382; Appendix L, The IMS, Poikselka & Mayer, @ 2009, John Wiley & Sons Ltd, Chapter 1 Introduction, 14 pages.
Petitioner AT&T Services, Inc. EXHIBIT 1003, Case No. IPR2017-01382; Appendix M, The IMS, Poikselka & Mayer, @ 2009, John Wiley & Sons Ltd, pp. 24-25 and 86-94, 13 pages.
Petitioner AT&T Services, Inc. EXHIBIT 1003, Case No. IPR2017-01382; Appendix N, Chapter 9, Telecommunications Essentials, Lillian Goleniewski, @ 2002, 42 pages.
Petitioner AT&T Services, Inc. EXHIBIT 1003, Case No. IPR2017-01382; Appendix O, Softswitch, Architecture for VoIP, Franklin D. Ohrtman, Jr., @ 2003, pp. 238-239, 4 pages.
Petitioner AT&T Services, Inc. EXHIBIT 1003, Case No. IPR2017-01382; Appendix p. Softswitch, Architecture for VoIP, Franklin D. Ohrtman, Jr., @ 2003, Chapter 4, pp. 67-86, 22 pages.
Petitioner AT&T Services, Inc. EXHIBIT 1003, Case No. IPR2017-01382; Appendix Q, Softswitch, Architecture for VoIP, Franklin D. Ohrtman, Jr., @ 2003, Chapter 5, pp. 87-112, 28 pages.
Petitioner AT&T Services, Inc. EXHIBIT 1003, Case No. IPR2017-01382; Appendix R, Telecommunications Essentials, Lillian Goleniewski, @ 2002, p. 221, 3 pages.
Petitioner AT&T Services, Inc. EXHIBIT 1003, Case No. IPR2017-01382; Appendix S, NetworkWorking Group, RFC (Request for Comments): 1122, Internat Engineering Task Force, R. Braden, Ed., Oct. 1989, pp. 18-25, 9 pages.
Petitioner AT&T Services, Inc. EXHIBIT 1003, Case No. IPR2017-01382; Appendix T, RFC (Request for Comments): 791, Internet Protocol, Darpa Internet Program, Protocol Specification, Sep. 1981, by Information Sciences Institute, USC, 50 pages.
Petitioner AT&T Services, Inc. EXHIBIT 1003, Case No. IPR2017-01382; Appendix U, Network Working Group, RFC (Request for Comments): 1034, P. Mockapetris, ISI, Nov. 1987, pp. 1-55, 55 pages.
Petitioner AT&T Services, Inc. EXHIBIT 1003, Case No. IPR2017-01382; Appendix V, Network Working Group, RFC (Request for Comments): 1035, P. Mockapetris, ISI, Nov. 1987, pp. 1-55, 55 pages.
Petitioner AT&T Services, Inc. EXHIBIT 1003, Case No. IPR2017-01382; Appendix W, Network Working Group, RFC (Request for Comments): 3761, P. Faltstrom et al., Apr. 2004, pp. 1-18, 18 pages.
Petitioner AT&T Services, Inc. EXHIBIT 1003, Case No. IPR2017-01382; Appendix X, U.S. Pat. No. 6,594,254 B1, to Kelly, 18 pages.
Petitioner AT&T Services, Inc. EXHIBIT 1003, Case No. IPR2017-01382; Appendix Y, ITU-T Recommendation H.323 (Jul. 2003), 298 pages.
Petitioner AT&T Services, Inc. EXHIBIT 1003, Case No. IPR2017-01382; Appendix Z, Telcordia Notes on the Networks, SR-2275, Issue 4, Oct. 2000, pp. 6-306-6-309, 4 pages.
Petitioner AT&T Services, Inc. EXHIBIT 1003, Case No. IPR2017-01382; Appendix AA, Telcordia Notes on the Networks, SR-2275, Issue 4, Oct. 2000, pp. 14-10-14-13, 6 pages.
Petitioner AT&T Services, Inc. EXHIBIT 1003, Case No. IPR2017-01382; Appendix BB, The Internet Engineering Task Force (IETF®), May 5, 2017, 2 pages.
Petitioner AT&T Services, Inc. EXHIBIT 1003, Case No. IPR2017-01382; Appendix CC, Network Working Group, RFC (Request for Comments): 3261, J. Rosenberg et al., Jun. 2002, 269 pages.
Petitioner AT&T Services, Inc. EXHIBIT 1003, Case No. IPR2017-01382; Appendix DD, Network Working Group, RFC (Request for Comments): 3666, A. Johnston et al., Dec. 2003, 118 pages.
Petitioner AT&T Services, Inc. EXHIBIT 1003, Case No. IPR2017-01382; Appendix EE, Network Working Group, RFC (Request for Comments): 3665, A. Johnston et al., Dec. 2003, 94 pages.
Petitioner AT&T Services, Inc. EXHIBIT 1003, Case No. IPR2017-01382; Appendix FF, Network Working Group, RFC (Request for Comments): 2327, M. Handley et al., Apr. 1998, 42 pages.
Petitioner AT&T Services, Inc. EXHIBIT 1003, Case No. IPR2017-01382; Appendix GG, ITU-T Recommendation Q.931 (May 1998), 345 pages.
Petitioner AT&T Services, Inc. EXHIBIT 1003, Case No. IPR2017-01382; Appendix HH, Telcordia Notes on the Networks, SR-2275, Issue 4, Oct. 2000, pp. 14-76-14-77, 4 pages.
Petitioner AT&T Services, Inc. EXHIBIT 1003, Case No. IPR2017-01382; Appendix II, Telcordia Notes on the Networks, SR-2275, Issue 4, Oct. 2000, p. 10-7, 3 pages.
Petitioner AT&T Services, Inc. EXHIBIT 1004, Case No. IPR2017-01382; James R. Bress, Curriculum Vitae, 26 pages.
Petitioner AT&T Services, Inc. EXHIBIT 1005, Case No. IPR2017-01382; U.S. Pat. No. 6,240,449, Issued May 29, 2001 to Raymond Nadeau, 13 pages.
Petitioner AT&T Services, Inc. EXHIBIT 1006, Case No. IPR2017-01382; U.S. Pat. No. 6,594,254 B1, Issued Jul. 15, 2003 to Keith C. Kelly, 18 pages.
Petitioner AT&T Services, Inc. EXHIBIT 1007, Case No. IPR2017-01382; U.S. Pat. No. 7,715,413 B2, Issued May 11, 2010, to Vaziri et al., 53 pages.
Petitioner AT&T Services, Inc. EXHIBIT 1008, Case No. IPR2017-01382; Decision, Institution of Inter Partes Review, 37 C.F.R. § 42.108, Paper 6, Entered Nov. 21, 2016, United States Patent and Trademark Office, Before the Patent Trial and Appeal Board, *Apple Inc., Petitioner,* v. *Voip-Pal.Com Inc., Patent Owner*, Case IPR2016-01201, U.S. Pat. No. 8,542,815 B2, Before Barbara A. Benoit, Lynne E. Pettigrew, and Stacy B. Margolies, Administrative Patent Judges, 33 pages.
Petitioner AT&T Services, Inc. EXHIBIT 1009, Case No. IPR2017-01382; p. 221 and Chapter 11, Telecommunications Essentials, Lillian Goleniewski, @ 2002, 44 pages.
Petitioner AT&T Services, Inc. EXHIBIT 1010, Case No. IPR2017-01382; RFC (Request for lComments): 791, Internet Protocol, Darpa Internet Program, Protocol Specification, Sep. 1981, by Information Sciences Institute, USC, 50 pages.
Petitioner AT&T Services, Inc. EXHIBIT 1011, Case No. IPR2017-01382; ITU-T Recommendation H.323 (Jul. 2003), 298 pages.
Petitioner AT&T Services, Inc. EXHIBIT 1012, Case No. IPR2017-01382; Telcordia Notes on the Networks, SR-2275, Issue 4, Oct. 2000, p. 10-7, 3 pages.
Document Title: in the United States Patent and Trademark Office; Before the Patent Trial and Appeal Board; *AT&T Services, Inc., Petitioner* v. *Digifonica (International) Limited Patent Owner*, Case No. IPR2017-01383; U.S. Pat. No. 9,179,005; Petition for Inter Partes Review of U.S. Pat. No. 9,179,005; Dated May 8, 2017, 92 pages.
Petitioner AT&T Services, Inc. EXHIBIT 1003, United States Patent and Trademark Office; Before the Patent Trial and Appeal Board; *AT&T Services, Inc., Petitioner* v. *Digifonica (International) Limited Patent Owner*, U.S. Pat. No. 9,179,005, Inter Partes Review No.|IPR2017-01383; Declaration of James Bress in Support of Petition for Inter Partes Review of U.S. Pat. No. 9,179,005; with Appendices A through II, 2094 pages. Appendices A through II are identical to those previously listed hereinabove as cite Nos. 876-910.
Petitioner AT&T Services, Inc. EXHIBIT 1004, Case No. IPR2017-01383; James R. Bress, Curriculum Vitae, 26 pages.
Petitioner AT&T Services, Inc. EXHIBIT 1005, Case No. IPR2017-01383; U.S. Pat. No. 6,240,449, Issued May 29, 2001 to Raymond Nadeau, 13 pages.
Petitioner AT&T Services, Inc. EXHIBIT 1006, Case No. IPR2017-01383; U.S. Publication No. 2004/0218748 A1, Published Nov. 4, 2004, by Stephen Fisher, 18 pages.
Petitioner AT&T Services, Inc. EXHIBIT 1007, Case No. IPR2017-01383; U.S. Pat. No. 6,594,254 B1, Issued Jul. 15, 2003, to Keith C. Kelly, 18 pages.
Petitioner AT&T Services, Inc. EXHIBIT 1008, Case No. IPR2017-01383; U.S. Pat. No. 6,674,850 B2, Issued Jan. 6, 2004, to Vu et al., 10 pages.
Petitioner AT&T Services, Inc. EXHIBIT 1009, Case No. IPR2017-01383; Decision, Institution of Inter Partes Review, 37 C.F.R. § 42.108, Paper 6, Entered Nov. 21, 2016, United States Patent and Trademark Office, Before the Patent Trial and Appeal Board, *Apple*

(56) References Cited

OTHER PUBLICATIONS

Inc., Petitioner, v. Voip-Pal.Com Inc., Patent Owner, Case IPR2016-01198, U.S. Pat. No. 9,179,005 B2, Before Barbara A. Benoit, Lynne E. Pettigrew, and Stacy B. Margolies, Administrative Patent Judges, 32 pages.
Petitioner AT&T Services, Inc. EXHIBIT 1010, Case No. IPR2017-01383; Patent Owner Response To Petition, Filed Feb. 10, 2017, United States Patent and Trademark Office, Before the Patent Trial and Appeal Board, Apple Inc., Petitioner, v. Voip-Pal.Com, Inc., Patent Owner, Case IPR2016-01198, U.S. Pat. No. 9,179,005 B2, 78 pages.
Document Title: in the United States Patent and Trademark Office; Before the Patent Trial and Appeal Board; AT&T Services, Inc., Petitioner v. Digifonica (International) Limited Patent Owner, Case No. IPR2017-01384; U.S. Pat. No. 9,179,005; Petition for Inter Partes Review of U.S. Pat. No. 9,179,005; Dated May 7, 2017, 70 pages.
Petitioner AT&T Services, Inc. EXHIBIT 1003, United States Patent and Trademark Office; Before the Patent Trial and Appeal Board; AT&T Services, Inc., Petitioner v. Digifonica (International) Limited Patent Owner, U.S. Pat. No. 9,179,005, Inter Partes Review No. IPR2017-01384; Declaration of James Bress in Support of Petition for Inter Partes Review of U.S. Pat. No. 9,179,005; with Appendices A through II, 2085 pages. Appendices A through II are identical to those previously listed hereinabove as cite Nos. 876-910.
Petitioner AT&T Services, Inc. EXHIBIT 1004, Case No. IPR2017-01384; James R. Bress, Curriculum Vitae, 26 pages.
Petitioner AT&T Services, Inc. EXHIBIT 1005, Case No. IPR2017-01384; U.S. Pat. No. 6,240,449, Issued May 29, 2001 to Raymond Nadeau, 13 pages.
Petitioner AT&T Services, Inc. EXHIBIT 1006, Case No. IPR2017-01384; U.S. Pat. No. 6,594,254 B1, Issued Jul. 15, 2003, to Keith C. Kelly, 18 pages.
Petitioner AT&T Services, Inc. EXHIBIT 1007, Case No. IPR2017-01384; U.S. Pat. No. 7,715,413 B2, Issued May 11, 2010, to Vaziri et al., 53 pages.
Petitioner AT&T Services, Inc. EXHIBIT 1008, Case No. IPR2017-01384; Decision, Institution of Inter Partes Review, 37 C.F.R. § 42.108, Paper 6, Entered Nov. 21, 2016, United States Patent and Trademark Office, Before the Patent Trial and Appeal Board, Apple Inc., Petitioner, v. Voip-Pal.Com Inc., Patent Owner, Case IPR2016-01198, U.S. Pat. No. 9,179,005 B2, Before Barbara A. Benoit, Lynne E. Pettigrew, and Stacy B. Margolies, Administrative Patent Judges, 32 pages.
Petitioner AT&T Services, Inc. EXHIBIT 1009, Case No. IPR2017-01384; p. 221 and Chapter 11, Telecommunications Essentials, Lillian Goleniewski, @ 2002, 44 pages.
Petitioner AT&T Services, Inc. EXHIBIT 1010, Case No. IPR2017-01384; RFC (Request for Comments): 791, Internet Protocol, Darpa Internet Program, Protocol Specification, Sep. 1981, by Information Sciences Institute, USC, 50 pages.
Petitioner AT&T Services, Inc. EXHIBIT 1011, Case No. IPR2017-01384; ITU-T Recommendation H.323 (Jul. 2003), 298 pages.
Petitioner AT&T Services, Inc. EXHIBIT 1012, Case No. IPR2017-01384; Telcordia Notes on the Networks, SR-2275, Issue 4, Oct. 2000, p. 10-7, 3 pages.
Document Title: United States Patent and Trademark Office; Before the Patent Trial and Appeal Board; Apple Inc., Petitioner v. Voip-Pal.Com Inc., Patent Owner; Case No. IPR2016-01201; U.S. Pat. No. 8,542,815; Petitioner's Reply To Patent Owner's Response, Dated May 17, 2017, 34 pages.
Petitioner Apple Inc. Exhibit 1007, United States Patent and Trademark Office; Before the Patent Trial and Appeal Board; Apple Inc., Petitioner v. Voip-Pal.Com,Inc., Patent Owner; Case No. IPR2016-01201; U.S. Pat. No. 8,542,815; Discovery Deposition of William Henry Mangione-Smith, taken on Apr. 19, 2017 in Case No. IPR2016-01198; U.S. Pat. No. 9,179,005, 213 pages.
Petitioner Apple Inc. Exhibit 1008, United States Patent and Trademark Office; Before the Patent Trial and Appeal Board; Apple Inc.,
Petitioner v. Voip-Pal.Com, Inc., Patent Owner; Case No. IPR2016-01201; U.S. Pat. No. 8,542,815; Discovery Deposition of John Rutter, taken (by phone) on Apr. 5, 2017 in Case No. IPR2016-01198; U.S. Pat. No. 9,179,005, 43 pages.
Petitioner Apple Inc. Exhibit 1009, United States Patent and Trademark Office; Before the Patent Trial and Appeal Board; Apple Inc., Petitioner v. Voip-Pal.Com, Inc., Patent Owner; Case No. IPR2016-01201; U.S. Pat. No. 8,542,815; Discovery Deposition of David Terry, taken on Mar. 24, 2017 in Case No. IPR2016-01198; U.S. Pat. No. 9,179,005, 95 pages.
Petitioner Apple Inc. Exhibit 1010, United States Patent and Trademark Office; Before the Patent Trial and Appeal Board; Apple Inc., Petitioner v. Voip-Pal.Com, Inc., Patent Owner; Case No. IPR2016-01201; U.S. Pat. No. 8,542,815; Discovery Deposition of Clay Perreault, taken on Apr. 12, 2017 in Case No. IPR2016-01198; U.S. Pat. No. 9,179,005, 118 pages.
Petitioner Apple Inc. Exhibit 1011, United States Patent and Trademark Office; Before the Patent Trial and Appeal Board; Apple Inc., Petitioner v. Voip-Pal.Com, Inc., Patent Owner; Case No. IPR2016-01201; U.S. Pat. No. 8,542,815; Complaint for Patent Infringement [Jury Demand], United States District Court, District of Nevada, Case No. 2:16-CV-00260, Voip-Pal.Com, Inc., a Nevada corporation, Plaintiff, v. Apple, Inc., a California corporation, Defendants, filed Feb. 9, 2016, 8 pages.
Petitioner Apple Inc. Exhibit 1012, United States Patent and Trademark Office; Before the Patent Trial and Appeal Board; Apple Inc., Petitioner v. Voip-Pal.Com, Inc., Patent Owner; Case No. IPR2016-01201; U.S. Pat. No. 8,542,815; Discovery Deposition of Johan Emil Viktor Bjorsell, taken on Mar. 24, 2017 in Case No. IPR2016-01198; U.S. Pat. No. 9,179,005, 204 pages.
Petitioner Apple Inc. Exhibit 1013, United States Patent and Trademark Office; Before the Patent Trial and Appeal Board; Apple Inc., Petitioner v. Voip-Pal.Com, Inc., Patent Owner; Case No. IPR2016-01201; U.S. Pat. No. 8,542,815; Letter dated Apr. 21, 2017 to Adam P. Seitz et al., Erise IP, P.A., re: IPR2016-01198 & IPR1026-01201, "Pursuant to the Board Order of Apr. 19, 2017 (Paper 28) . . . " from Kerry Taylor, Knobbe, Martens, Olson & Bear, LLP, 1 page.
Petitioner Apple Inc. Exhibit 1014, United States Patent and Trademark Office; Before the Patent Trial and Appeal Board; Apple Inc., Petitioner v. Voip-Pal.Com, Inc., Patent Owner; Case No. IPR2016-01201; U.S. Pat. No. 8,542,815; Email dated May 1, 2017 to Adam P. Seitz et al., Erise IP, P.A., re: IPR2016-01198 & IPR1026-01201— Fuad Arafa, from Kerry Taylor, Knobbe, Martens, Olson & Bear, LLP, 2 pages.
Document Title: United States Patent and Trademark Office; Before the Patent Trial and Appeal Board; Apple Inc., Petitioner v. Voip-Pal.Com Inc., Patent Owner; Case No. IPR2016-01198; U.S. Pat. No. 9,179,005; Petitioner's Reply To Patent Owner's Response, Paper 34, Dated May 17, 2017, 33 pages.
Petitioner Apple Inc. Exhibit 1010, United States Patent and Trademark Office; Before the Patent Trial and Appeal Board; Apple Inc., Petitioner v. Voip-Pal.Com, Inc., Patent Owner; Case No. IPR2016-01198; U.S. Pat. No. 9,179,005; Discovery Deposition of William Henry Mangione-Smith, taken on Apr. 19, 2017 in Case No. IPR2016-01198; U.S. Pat. No. 9,179,005, 213 pages.
Petitioner Apple Inc. Exhibit 1011, United States Patent and Trademark Office; Before the Patent Trial and Appeal Board; Apple Inc., Petitioner v. Voip-Pal.Com, Inc., Patent Owner; Case No. IPR2016-01198; U.S. Pat. No. 9,179,005; Discovery Deposition of John Rutter, taken (by phone) on Apr. 5, 2017 in Case No. IPR2016-01198; U.S. Pat. No. 9,179,005, 43 pages.
Petitioner Apple Inc. Exhibit 1012, United States Patent and Trademark Office; Before the Patent Trial and Appeal Board; Apple Inc., Petitioner v. Voip-Pal.Com, Inc., Patent Owner; Case No. IPR2016-01198; U.S. Pat. No. 9,179,005; Discovery Deposition of David Terry, taken on Mar. 24, 2017 in Case No. IPR2016-01198; U.S. Pat. No. 9,179,005, 95 pages.
Petitioner Apple Inc. Exhibit 1013, United States Patent and Trademark Office; Before the Patent Trial and Appeal Board; Apple Inc., Petitioner v. Voip-Pal.Com, Inc., Patent Owner; Case No. IPR2016-01198; U.S. Pat. No. 9,179,005; Discovery Deposition of Clay Perreault, taken on Apr. 12, 2017 in Case No. IPR2016-01198; U.S. Pat. No. 9,179,005, 118 pages.

(56) References Cited

OTHER PUBLICATIONS

Petitioner Apple Inc. Exhibit 1014, United States Patent and Trademark Office; Before the Patent Trial and Appeal Board; *Apple Inc., Petitioner* v. *Voip-Pal.Com, Inc., Patent Owner*; Case No. IPR2016-01198; U.S. Pat. No. 9,179,005; Complaint for Patent Infringement [Jury Demand], United States District Court, District of Nevada, Case No. 2:16-CV-00260, *Voip-Pal.Com, Inc., a Nevada corporation, Plaintiff,* v. *Apple, Inc., a California corporation, Defendants*, filed Feb. 9, 2016, 8 pages.
Petitioner Apple Inc. Exhibit 1015, United States Patent and Trademark Office; Before the Patent Trial and Appeal Board; *Apple Inc., Petitioner* v. *Voip-Pal.Com, Inc., Patent Owner*; Case No. IPR2016-01198; U.S. Pat. No. 9,179,005; Discovery Deposition of Johan Emil Viktor Bjorsell, taken on Mar. 24, 2017 in Case No. IPR2016-01198; U.S Pat. No. 9,179,005, 204 pages.
Petitioner Apple Inc. Exhibit 1016, United States Patent and Trademark Office; Before the Patent Trial and Appeal Board; *Apple Inc., Petitioner* v. *Voip-Pal.Com, Inc., Patent Owner*; Case No. IPR2016-01198; U.S. Pat. No. 9,179,005; Letter dated Apr. 21, 2017 to Adam P. Seitz et al., Erise IP, P.A., re: IPR2016-01198 & IPR1026-01201, "Pursuant to the Board Order of Apr. 19, 2017 (Paper 28) . . . " from Kerry Taylor, Knobbe, Martens, Olson & Bear, LLP, 1 page.
Petitioner Apple Inc. Exhibit 1017, United States Patent and Trademark Office; Before the Patent Trial and Appeal Board; *Apple Inc., Petitioner* v. *Voip-Pal.Com, Inc., Patent Owner*; Case No. IPR2016-01198; U.S. Pat. No. 9,179,005; Email dated May 1, 2017 to Adam P. Seitz et al., Erise IP, P.A., re: IPR2016-01198 & IPR1026-01201—Fuad Arafa, from Kerry Taylor, Knobbe, Martens, Olson & Bear, LLP, 2 pages.
Document Title: United States Patent and Trademark Office; Before the Patent Trial and Appeal Board; *Apple Inc., Petitioner* v. *Voip-Pal.Com.Inc., Patent Owner*, CaseNo. IPR2016-01201, U.S. Pat. No. 8,542,815; Patent Owner Objections To Apple Evidence Served With Petitioner's Reply, Filed on behalf of Patent Owner Voip-Pal.com Inc., Filed: May 24, 2017, 6 pages.
Document Title: United States Patent and Trademark Office; Before the Patent Trial and Appeal Board; *Apple Inc., Petitioner* v. *Voip-Pal.Com.Inc., Patent Owner*, Case No. IPR2016-01198, U.S. Pat. No. 9,179,005; Patent Owner Objections To Apple Evidence Served With Petitioner's Reply, Filed on behalf of Patent Owner Voip-Pal.com Inc., Filed: May 24, 2017, 6 pages.
Petitioner's Request for Oral Argument, United States Patent and Trademarkoffice, Before the Patent Trial and Appeal Board, *Apple Inc., Petitioner* v. *Voip-Pal.Com.Inc., Patent Owner*, Case No. IPR2016-01201, U.S. Pat. No. 8,542,815, dated Jun. 14, 2017, 4 pages.
Patent Owner Sur-Reply in Response To Petitioner's Reply, United States Patent and Trademark Office, Before the Patent Trial and Appeal Board, *Apple Inc., Petitioner* v. *Voip-Pal.Com.Inc., Patent Owner*, Case No. IPR2016-01201, U.S. Pat. No. 8,542,815, dated Jun. 14, 2017, 8 pages.
Patent Owner Request for Oral Argument, United States Patent and Trademark Office, Before the Patent Trial and Appeal Board, *Apple Inc., Petitioner* v. *Voip-Pal.Com.Inc., Patent Owner*, Case No. IPR2016-01201, U.S. Pat. No. 8,542,815, dated Jun. 14, 2017, 4 pages.
Patent Owner Motion To Exclude, United States Patent and Trademark Office,Before the Patent Trial and Appeal Board, *Apple Inc., Petitioner* v. *Voip-Pal.Com.Inc., Patent Owner*, Case No. IPR2016-01201, U.S. Pat. No. 8,542,815, dated Jun. 14, 2017, 18 pages.
Voip-Pal Ex. 2052, IPR2016-01201, *Apple Inc.* vs. *Voip-Pal.com, Inc.*, Reporter's Transcript of Telephonic Hearing, Jun. 7, 2017, 16 sheets.
Petitioner's Request for Oral Argument, United States Patent and Trademarkoffice, Before the Patent Trial and Appeal Board, *Apple Inc., Petitioner* v. *Voip-Pal.Com.Inc., Patent Owner*, Case No. IPR2016-01198, U.S. Pat. No. 9,179,005, dated Jun. 14, 2017, 4 pages.
Patent Owner Sur-Reply in Response To Petitioner's Reply, United States Patent and Trademark Office, Before the Patent Trial and Appeal Board, *Apple Inc., Petitioner* v. *Voip-Pal.Com.Inc., Patent Owner*, Case No. IPR2016-01198, U.S. Pat. No. 9,179,005, dated Jun. 14, 2017, 8 pages.
Patent Owner Request for Oral Argument, United States Patent and Trademark Office, Before the Patent Trial and Appeal Board, *Apple Inc., Petitioner* v. *Voip-Pal.Com.Inc., Patent Owner*, Case No. IPR2016-01198, U.S. Pat. No. 9,179,005, dated Jun. 14, 2017, 4 pages.
Patent Owner Motion To Exclude, United States Patent and Trademark Office,Before the Patent Trial and Appeal Board, *Apple Inc., Petitioner* v. *Voip-Pal.Com.Inc., Patent Owner*, Case No. IPR2016-01198, U.S. Pat. No. 9,179,005, dated Jun. 14, 2017, 18 pages.
Voip-Pal Ex. 2052, IPR2016-01198, *Apple Inc.* vs. *Voip-Pal.com, Inc.*, Reporter's Transcript of Telephonic Hearing, Jun. 7, 2017, 16 sheets.
Order, Conduct of Proceeding, 37 C.F.R. § 42.5, United States Patent and Trademarkoffice, Before the Patent Trial and Appeal Board, *Apple Inc., Petitioner* v. *Voip-Pal.Com.Inc., Patent Owner*, Cases IPR2016-01198 and IPR2016-01201, U.S. Pat. No. 9,179,005 B2 and 8,542,815 B2, Paper No. 37, Filed: Jun. 13, 2017, 3 pages.
Voip-Pal Ex. 2053, IPR2016-01198, *Apple Inc.* vs. *Voip-Pal.com, Inc.*, Reporter's Transcript of Telephonic Hearing, Jun. 20, 2017, 25 pages.
Voip-Pal Ex. 2053, IPR2016-01201, *Apple Inc.* vs. *Voip-Pal.com, Inc.*, Reporter's Transcript of Telephonic Hearing, Jun. 20, 2017, 25 pages.
Order, Conduct of Proceeding, 37 C.F.R. § 42.5, United States Patent and Trademark Office, Before the Patent Trail and Appeal Board, *Apple Inc., Petitioner,* v. *Voip-Pal.Com, Inc., Patent Owner*. Cases IPR2016-01198 and IPR2016-01201, U.S. Pat. No. 9,179,005 B2 and 8,542,815 B2, Paper No. 43, Filed: Jun. 22, 2017, 4 pages.
Order, Trial Hearing, 37 C.F.R. § 42.70, United States Patent and Trademark Office, Before the Patent Trail and Appeal Board, *Apple Inc., Petitioner,* v. *Voip-Pal.Com, Inc., Patent Owner*. Cases IPR2016-01198 and IPR2016-01201, U.S. Pat. No. 9,179,005 B2 and 8,542,815 B2, Paper No. 45, Filed: Jun. 26, 2017, 4 pages.
Petitioner's Opposition To Patent Owner's Motion To Exclude, Unted Statespatent and Trademark Office, Before the Patent Trial and Appeal Board, *Apple Inc., Petitioner* v. *Voip-Pal.Com, Inc., Patent Owner*, Case No. IPR2016-01201, U.S. Pat. No. 8,542,815, Date: Jun. 26, 2017, 15 pages.
Petitioner's Opposition To Patent Owner's Motion To Exclude, Unted Statespatent and Trademark Office, Before the Patent Trial and Appeal Board, *Apple Inc., Petitioner* v. *Voip-Pal.Com, Inc., Patent Owner*, Case No. IPR2016-01198, U.S. Pat. No. 9,179,005, Date: Jun. 26, 2017, 15 pages.
Patent Owner Reply To Opposition To Motion To Exclude, United States Patent and Trademark Office, Before the Patent Trial and Appeal Board, *Apple Inc., Petitioner* v. *Voip-Pal.Com, Inc., Patent Owner*, Case No. IPR 2016-01198, U.S. Pat. No. 9,179,005, Filed: Jul. 3, 2017, 8 pages.
Patent Owner Reply To Opposition To Motion To Exclude, United States Patent and Trademark Office, Before the Patent Trial and Appeal Board, *Apple Inc., Petitioner* v. *Voip-Pal.Com, Inc., Patent Owner*, Case No. IPR 2016-01201, U.S. Pat. No. 8,542,815, Filed: Jul. 3, 2017, 8 pages.
Voip-Pal Ex. 2054, IPR2016-01198, Voip-PAL's Demonstratives For Oral Hearing, *Apple Inc. v. Voip-Pal.Com, Inc.*, Case IPR2016-01201 (U.S. Pat. No. 8,542,815), Case IPR2016-01198 (U.S. Pat. No. 9,179,005), Jul. 20, 2017, 34 pages.
Voip-Pal Ex. 2054, IPR2016-01201, Voip-PAL's Demonstratives For Oral Hearing, *Apple Inc. v. Voip-Pal.Com, Inc.*, Case IPR2016-01201 (U.S. Pat. No. 8,542,815), Case IPR2016-01198 (U.S. Pat. No. 9,179,005), Jul. 20, 2017, 34 pages.
Petitioner Apple Inc. Ex. 1018, Petitioner's Demonstrative Exhibits, Inter Partes Reviews, U.S. Pat. Nos. 9,179,005 & 8,542,815, Oral Argument, Jul. 20, 2017, *Apple Inc. v. Voip-Pal.Com, Inc.*, Case IPR2016-01198; U.S. Pat. No. 9,179,005, Case IPR2016-01201; U.S. Pat. No. 8,542,815, 46 pages.
Patent Owner's Preliminary Response To Petition for Inter Partes Review, United States Patent and Trademark Office, Before the Patent Trial and Appeal Board, *AT&T Services, Inc., Petitioner,* v.

(56) References Cited

OTHER PUBLICATIONS

*VoIP-PAL.COM, INC., Patent Owner*, Case No. IPR2017-01382, U.S. Pat. No. 8,542,815, dated Aug. 24, 2017, 71 pages.
Patent Owner's Preliminary Response To Petition for Inter Partes Review, United States Patent and Trademark Office, Before the Patent Trial and Appeal Board, *AT&T Services, Inc., Petitioner*, v. *Voip-Pal.Com, Inc., Patent Owner*, Case No. IPR2017-01383, U.S. Pat. No. 9,179,005, dated Aug. 24, 2017, 74 pages.
Patent Owner's Preliminary Response To Petition for Inter Partes Review, United States Patent and Trademark Office, Before the Patent Trial and Appeal Board, *AT&T Services, Inc., Petitioner*, v. *Voip-Pal.Com, Inc., Patent Owner*, Case No. IPR2017-01384, U.S. Pat. No. 9,179,005, dated Aug. 24, 2017, 61 pages.
Patent Owner's Preliminary Response To Petition for Inter Partes Review, United States Patent and Trademark Office, Before the Patent Trial and Appeal Board, *Apple Inc., Petitioner*, v. *Voip-Pal.Com, Inc., Patent Owner*, Case No. IPR2017-01398, U.S. Pat. No. 9,179,005, dated Aug. 25, 2017, 76 pages.
Patent Owner's Preliminary Response To Petition for Inter Partes Review, United States Patent and Trademark Office, Before the Patent Trial and Appeal Board, *Apple Inc., Petitioner*, v. *Voip-Pal.Com, Inc., Patent Owner*, Case No. IPR2017-01399, U.S. Pat. No. 8,542,815, dated Aug. 25, 2017, 77 pages.
United States Patent and Trademark Office; Before the Patent Trial and Appeal Board; *Apple Inc., Petitioner*, v. *Voip-Pal.Com, Inc., Patent Owner*; Cases IPR2016-01198 andIPR2016-01201; U.S. Pat. No. 9,179,005 B2 and 8,542,815 B2; Record of Oral Hearing, Held: Jul. 20, 2017; Before Josiah C. Cocks, Jennifer Meyer Chagnon, and John A. Hudalla, Administrative Patent Judges, 83 pages.
United States Patent and Trademark Office; Before the Patent Trial and Appealboard; *Apple Inc., Petitioner*, v. *Voip-Pal.Com, Inc., Patent Owner*; Case IPR2016-01198, U.S. Pat. No. 9,179,005 B2; Final Written Decision; Paper 53, Entered: Nov. 20, 2017; 29 pages.
United States Patent and Trademark Office; Before the Patent Trial and Appealboard; *Apple Inc., Petitioner*, v. *Voip-Pal.Com, Inc., Patent Owner*; Case IPR2016-01201, U.S. Pat. No. 8,542,815 B2; Final Written Decision; Paper 54, Entered: Nov. 20, 2017; 29 pages.
United States Patent and Trademark Office; Before the Patent Trial and Appeal Board; *Apple Inc., Petitioner*, v. *Voip-Pal.Com, Inc., Patent Owner*; Case IPR2017-01399, U.S. Pat. No. 8,542,815 B2; Decision: Denying Institution of Inter Partes Review; Paper No. 6, Entered: Nov. 20, 2017; 23 pages.
United States Patent and Trademark Office; Before the Patent Trial and Appeal Board; *Apple Inc., Petitioner*, v. *Voip-Pal.Com, Inc., Patent Owner*; Case IPR2017-01398, U.S. Pat. No. 9,179,005 B2; Decision: Denying Institution of Inter Partes Review; Paper No. 6, Entered: Nov. 20, 2017; 23 pages.
United States Patent and Trademark Office; Before the Patent Trial and Appeal Board; *AT&T Services, Inc., Petitioner*, v. *Voip-Pal.Com, Inc., Patent Owner*; Case IPR2017-01382, U.S. Pat. No. 8,542,815 B2; Decision: Denying Institution of Inter Partes Review; Paper No. 8, Entered: Nov. 20, 2017; 28 pages.
United States Patent and Trademark Office; Before the Patent Trial and Appeal Board; *AT&T Services, Inc., Petitioner*, v. *Voip-Pal.Com, Inc., Patent Owner*; Case IPR2017-01383, U.S. Pat. No. 9,179,005 B2; Decision: Denying Institution of Inter Partes Review; Paper No. 8, Entered: Nov. 20, 2017; 43 pages.
United States Patent and Trademark Office; Before the Patent Trial and Appeal Board; *AT&T Services, Inc., Petitioner*, v. *Voip-Pal.Com, Inc., Patent Owner*; Case IPR2017-01384, U.S. Pat. No. 9,179,005 B2; Decision: Denying Institution of Inter Partes Review; Paper No. 8, Entered: Nov. 20, 2017; 31 pages.
United States Patent and Trademark Office; Before the Patent Trial and Appeal Board; *Apple Inc., Petitioner*, v. *Voip-Pal.Com, Inc., Patent Owner*; Cases IPR2016-01198 and IPR2016-01201, U.S. Pat. No. 9,179,005 B2 and 8,542,815 B2; Order, Conduct of Proceeding, 37 C.F.R. § 42.5; Paper No. 54, Entered: Dec. 20, 2017; 4 pages.
United States Patent and Trademark Office; Before the Patent Trial and Appeal Board; *Apple Inc., Petitioner*, v. *Voip-Pal.Com, Inc.,*
*Patent Owner*; Case No. IPR2016-01201, U.S. Pat. No. 8,542,815; Petitioner's Motion for Entry of Judgment in Favor of Petitioner etc; Paper 55, Date: Dec. 20, 2017; 18 pages.
United States Patent and Trademark Office; Before the Patent Trial and Appeal Board; *Apple Inc., Petitioner*, v. *Voip-Pal.Com, Inc., Patent Owner*; Case No. IPR2016-01201, U.S. Pat. No. 8,542,815; Petitioner's Updated Exhibit List; Date: Dec. 22, 2017; 4 pages.
United States Patent and Trademark Office; Before the Patent Trial and Appeal Board; *Apple Inc., Petitioner*, v. *Voip-Pal.Com, Inc., Patent Owner*; Case No. IPR2016-01201, U.S. Appl. No. 8,542,815; EXHIBIT 1019—Sep. 18, 2017 Voip-Pal Website advertising Dr. Sawyer's Letters; Date: Dec. 20, 2017; 1 page.
United States Patent and Trademark Office; Before the Patent Trial and Appeal Board; *Apple Inc., Petitioner*, v. *Voip-Pal.Com, Inc., Patent Owner*; Case No. IPR2016-01201, U.S. Pat. No. 8,542,815; EXHIBIT 1020—Sep. 2017 Voip-Pal Website posting and linking all of Dr. Sawyer's Letters; Date: Dec. 20, 2017; 2 pages.
United States Patent and Trademark Office; Before the Patent Trial and Appeal Board; *Apple Inc., Petitioner*, v. *Voip-Pal.Com, Inc., Patent Owner*; Case No. IPR2016-01198,U.S. Pat. No. 9,179,005 B2 and Case No. IPR2016-01201, U.S. Pat. No. 8,542,815 B2; IPR2016-01201 Exhibit 1021—Telephonic Hearing Before the Administrative Patent Judges: Dec. 19, 2017; 25 pages.
United States Patent and Trademark Office; Before the Patent Trial and Appeal Board; *Apple Inc., Petitioner*, v. *Voip-Pal.Com, Inc., Patent Owner*; Case No. IPR2016-01198, U.S. Pat. No. 9,179,005; Petitioner's Motion for Entry of Judgment in Favor of Petitioner etc; Date: Dec. 20, 2017; 18 pages.
United States Patent and Trademark Office; Before the Patent Trial and Appeal Board; *Apple Inc., Petitioner*, v. *Voip-Pal.Com, Inc., Patent Owner*; Case No. IPR2016-01198, U.S. Pat. No. 9,179,005; Petitioner's Updated Exhibit List; Date: Dec. 22, 2017; 4 pages.
United States Patent and Trademark Office; Before the Patent Trial and Appeal Board; *Apple Inc., Petitioner*, v. *Voip-Pal.Com, Inc., Patent Owner*; Case IPR2016-01198, U.S. Pat. No. 9,179,005 B2; Exhibit 1019—Sep. 18, 2017 Voip-Pal Website advertising Dr. Sawyer's Letters; Date: Dec. 20, 2017; 1 page.
United States Patent and Trademark Office; Before the Patent Trial and Appeal Board; *Apple Inc., Petitioner*, v. *Voip-Pal.Com, Inc., Patent Owner*; Case IPR2016-01198, U.S. Pat. No. 9,179,005 B2; Exhibit 1020—Sep. 2017 Voip-Pal Website posting and linking all of Dr. Sawyer's Letters; Date: Dec. 20, 2017; 2 pages.
United States Patent and Trademark Office; Before the Patent Trial and Appeal Board; *Apple Inc., Petitioner*, v. *Voip-Pal.Com, Inc., Patent Owner*; Case No. IPR2016-01198,U.S. Pat. No. 9,179,005 B2 and Case No. IPR2016-01201, U.S. Pat. No. 8,542,815 B2; IPR2016-01198 Exhibit 1021—Telephonic Hearing Before the Administrative Patent Judges: Dec. 19, 2017; 25 pages.
Exhibit 3001 filed Dec. 20, 2017—Letter from Ryan L. Thomas dated Dec. 19, 2017 re Representation of VoIP-Pal.com, Inc. in Conference Call to the Administrative Patent Judges in re IPR2016-01198 and IPR-2016-01201; 1 page.
Exhibit 3002 filed Dec. 20, 2017—Email from Attorney Adam Seitz dated Dec. 15, 2017 to the Administrative Patent Judges in re IPR2016-01198 and IPR-2016-01201 re Authorization To File Motion for Sanctions; 1 page.
Exhibit 3003 filed Dec. 20, 2017—Letter from Dr. Thomas E. Sawyer (Shareholder) dated May 1, 2017 to PTAB Chief Judge David P. Ruschke in re IPR2016-01198 and IPR-2016-01201 re Review of Proceedings, 6 pages.
Exhibit 3004 filed Dec. 20, 2017—Letter from Dr. Thomas E. Sawyer (Shareholder) dated Jun. 21, 2017 to PTAB Chief Judge David P. Ruschke in re IPR2016-01198 and IPR-2016-01201 re Review of Proceedings, 3 pages.
Exhibit 3005 filed Dec. 20, 2017—Letter from Dr. Thomas E. Sawyer (Shareholder) dated Jul. 11, 2017 to PTAB Chief Judge David P. Ruschke in re IPR2016-01198 and IPR-2016-01201 re Review of Proceedings, 5 pages.
Exhibit 3006 filed Dec. 20, 2017—Letter from Dr. Thomas E. Sawyer (Shareholder) dated Jul. 27, 2017 to the Secretary of the Department of Commerce Hon. Wilbur Ross et al. in re IPR2016-01198 and IPR-2016-01201 re Review of Proceedings, 6 pages.

(56) References Cited

OTHER PUBLICATIONS

Exhibit 3007 filed Dec. 20, 2017—Letter from Dr. Thomas E. Sawyer (Shareholder) dated Aug. 31, 2017 to the Secretary of the Department of Commerce Hon. Wilbur Ross in re IPR2016-01198 and IPR-2016-01201 re Review of Proceedings, 8 pages.
Exhibit 3008 filed Dec. 20, 2017—Letter from Dr. Thomas E. Sawyer (Shareholder) dated Oct. 23, 2017 to the PTAB Chief Judge David P. Ruschke et al. in re IPR2016-01198 and IPR-2016-01201 re Review of Proceedings, 10 pages.
United States Patent and Trademark Office; Before the Patent Trial and Appeal Board; *Apple Inc., Petitioner,* v. *Voip-Pal.Com, Inc., Patent Owner*; Case No. IPR2016-01198, U.S. Pat. No. 9,179,005; Patent Owner's Opposition To Apple's Motion for Sanctions Pursuant To Board Order of Dec. 20, 2017; Filed: Jan. 12, 2018; 17 pages.
United States Patent and Trademark Office; Before the Patent Trial and Appeal Board; *Apple Inc., Petitioner,* v. *Voip-Pal.Com, Inc., Patent Owner*; Case No. IPR2016-01198, U.S. Pat. No. 9,179,005; Patent Owner's Updated Exhibit List; Filed: Jan. 12, 2018; 9 pages.
Voip-Pal Exhibit 2056, IPR2016-01198; United States Patent and Trademark Office; Before the Patent Trial and Appeal Board; *Apple Inc., Petitioner,* v. *Voip-Pal.Com, Inc., Patent Owner*; Case No. IPR2016-01198, U.S. Pat. No. 9,179,005; Declaration in Support of Patent Owner's Opposition To Motion for Sanctions; Dated: Jan. 12, 2018; 12 pages.
United States Patent and Trademark Office; Before the Patent Trial and Appeal Board; *Apple Inc., Petitioner,* v. *Voip-Pal.Com, Inc., Patent Owner*; Case No. IPR2016-01201, U.S. Pat. No. 8,542,815; Patent Owner's Opposition To Apple's Motion for Sanctions Pursuant To Board Order of Dec. 20, 2017; Filed: Jan. 12, 2018; 17 pages.
United States Patent and Trademark Office; Before the Patent Trial and Appeal Board; *Apple Inc., Petitioner,* v. *Voip-Pal.Com, Inc., Patent Owner*; Case No. IPR2016-01201, U.S. Pat. No. 8,542,815; Patent Owner's Updated Exhibit List; Filed: Jan. 12, 2018; 9 pages.
Voip-Pal Exhibit 2056, IPR2016-01198; United States Patent and Trademark Office; Before the Patent Trial and Appeal Board; *Apple Inc., Petitioner,* v. *Voip-Pal.Com,Inc., Patent Owner*; Case No. IPR2016-01201, U.S. Pat. No. 8,542,815; Declaration in Support of Patent Owner's Opposition To Motion for Sanctions; Dated: Jan. 12, 2018; 12 pages.
Voip-Pal Exhibit 2057; IPR2016-01198 and IPR2016-01201; Declaration of Adam R. Knecht, Esq. Regarding Notice of Various Letters From Dr. Thomas Sawyer To the Honorable Judge Richard F. Boulware II (ECF Nos. 28 AND 32); including Exhibit A (7 pages), Exhibit B (19 pages) and Exhibit C (12 pages); Executed on Dec. 18, 2017; 40 pages.
Voip-Pal Exhibit 2058; IPR2016-01198 and IPR2016-01201; O'Brien et al., "Revealed: Federal Judges Guilty of Owning Stock in Corporations They Ruled On," Occupy.com (2014, May 1) 11 pages.
Voip-Pal Exhibit 2059; IPR2016-01198 and IPR2016-01201; Letter dated Aug. 7, 2013 from Kathryn Siehndel, USPTO FOIA Officer, , Re: Freedom of Information Act (FOIA) Request No. F-13-00218 concerning U.S. Pat. No. 7,139,761; 77 pages.
Voip-Pal Exhibit 2060; IPR2016-01198 and IPR2016-01201; Questionnaire for Non-Judicial Nominees; Affidavit executed by Michelle K. Lee Oct. 28, 2014; 40 pages.
Voip-Pal Exhibit 2061; IPR2016-01198 and IPR2016-01201; Davis, R., "PTAB's 'Death Squad' Label Not Totally Off-Base, Chief Says," Law360, New York (Aug. 14, 2014) 4 pages.
Voip-Pal Exhibit 2062; IPR2016-01198 and IPR2016-01201; Graham et al., "The Brainy Bunch," *Intellectual Property: An ALM Supplement*, Fall 2015, 7 pages.
Voip-Pal Exhibit 2063; IPR2016-01198 and IPR2016-01201; Patent Trial and Appeal Board Statistics, USPTO, Jan. 31, 2017, 15 pages.
Voip-Pal Exhibit 2064; IPR2016-01198 and IPR2016-01201; Davis, R., "Fed. Circ. Reverses PTAB Nix Of Synopsys Circuit Patent," Law360, New York, Apr. 24, 2017, 5 pages.
Voip-Pal Exhibit 2065; IPR2016-01198 and IPR2016-01201; Scheller et al. "Federal Circuit to PTAB: No. Short Cuts Allowed," *The National Law Review*; Apr. 25, 2017, 5 pages.
Voip-Pal Exhibit 2066; IPR2016-01198 and IPR2016-01201; Couturier, K. "How Europe Is Going After Apple, Google and Other U.S. Tech Giants," *New York Times*, Apr. 13, 2015, 1 page.
Voip-Pal Exhibit 2067; IPR2016-01198 and IPR2016-01201; Manjoo, F., "Tech Giants Seem Invincible. That Worries Lawmakers." *New York Times*, Jan. 4, 2017, 5 pages.
Voip-Pal Exhibit 2068; IPR2016-01198 and IPR2016-01201; Quinn et al., "Michelle Lee's views on patent quality out of touch with reality facing patent applicants," IPWatchdog@,Feb. 2, 2017, 5 pages.
Voip-Pal Exhibit 2069; IPR2016-01198 and IPR2016-01201; Quinn, G., "Michelle Lee launches PTAB initiative to 'shape and improve' IPR proceedings," IPWatchdog@, Apr. 10, 2017, 3 pages.
Voip-Pal Exhibit 2070; IPR2016-01198 and IPR2016-01201; Kampis, J., "Google employees have enjoyed revolving door during Obama administration," watchdog.org, Aug. 8, 2016, 6 pages.
Voip-Pal Exhibit 2071; IPR2016-01198 and IPR2016-01201; Dayen, D., "The Android Administration," *The Intercept_*, Apr. 22, 2016, 16 pages.
Voip-Pal Exhibit 2072; IPR2016-01198 and IPR2016-01201; Editor Charlie, "@scleland: HowGoogle Is Anti-employment Antiproperty & Pro-regulation," *Artist Rights Watch, News for the Artist Rights Advocacy Community*, Nov. 18, 2016, 3 pages.
Voip-Pal Exhibit 2073; IPR2016-01198 and IPR2016-01201; Press Release: "Voip-Pal Issues a Correction to its Press Release of Sep. 18, 2017," Voip-Pal.Com Inc., Jan. 11, 2018, 1 page.
Voip-Pal Exhibit 2074; IPR2016-01198 and IPR2016-01201; "Former head of Google patent strategy appointed to run U.S. patent agency," *ai (/Profile/12836/AppleInsider)*, Dec. 12, 2013, 8 pages.
Voip-Pal Exhibit 2075; IPR2016-01198 and IPR2016-01201; Vermont, S. "IPR Statistics Revisited: Yep, It's A Patent Killing Field," PatentAttorney.com, Feb. 8, 2017, 9 pages.
Voip-Pal Exhibit 2076; IPR2016-01198 and IPR2016-01201; Sterne et al., "PTAB Death Squads: Are All Commercially Viable Patents Invalid?" IPWatchdog®, Mar. 24, 2014, 5 pages.
Voip-Pal Exhibit 2077; IPR2016-01198 and IPR2016-01201; Sheafe, B., "Dear Congress: A SmallRequest on Behalf of the Innovators You (Theoretically) Represent: Part 2," *IPWire*, Jan. 12, 2018, 5 pages.
Voip-Pal Exhibit 2078; IPR2016-01198 and IPR2016-01201; Brachmann, S., "Are conflicts ofinterest at the PTAB leading to preferential decisions for Apple?" IPWatchdog®, Apr. 28, 2017, 5 pages.
Voip-Pal Exhibit 2079; IPR2016-01198 and IPR2016-01201; Quinn et al., "Patent owners do not like IPRs despite what Bloomberg Law, AIPLA study says," IPWatchdog®, Feb. 6, 2017, 5 pages.
Voip-Pal Exhibit 2080; IPR2016-01198 and IPR2016-01201; "Does Google's Michelle Lee Work ForBoth Google and the U.S. Patent Office at the Same Time?" *The Corruption Times, Your Public New WIKI For Social Updates*, Apr. 6, 2016, 8 pages.
Voip-Pal Exhibit 2081; IPR2016-01198 and IPR2016-01201; Morinville, P., "The Senate Must Vet Vishal Amin," IPWatchdog®, Apr. 23, 2017, 4 pages.
Voip-Pal Exhibit 2082; IPR2016-01198 and IPR2016-01201; The New York Times "May 15, 1911,Supreme Court Orders Standard Oil to Be Broken Up," *By The Learning Network*, May 15, 2012, 3 pages.
Voip-Pal Exhibit 2083; IPR2016-01198 and IPR2016-01201; Simpson et al., "PTAB Kill Rates: How IPRs Are Affecting Patents," *Law360*, New York, Sep. 15, 2015, 6 pages.
Voip-Pal Exhibit 2084; IPR2016-01198 and IPR2016-01201; Vermont, S., "Ipr Statistics Revisited: Yep, It's A Patent Killing Field," PatentAttorney.com, Feb. 8, 2017, 9 pages.
Voip-Pal Exhibit 2085; IPR2016-01198 and IPR2016-01201; Robinson, E., "Why the Unified Patents Model Would Not Work in China," IPWatchdog@, Apr. 26, 2017, 4 pages.
Voip-Pal Exhibit 2086; IPR2016-01198 and IPR2016-01201; Brachmann et al., "US Inventor sets patents on fire as part of PTAB protest at USPTO," IPWatchdog®, Aug. 11, 2017, 4 pages.

(56) References Cited

OTHER PUBLICATIONS

Voip-Pal Exhibit 2087; IPR2016-01198 and IPR2016-01201; "Selection process for assigning judges to expanded PTAB panels," 717 Madison Place, Aug. 28, 2017, 3 pages.
Voip-Pal Exhibit 2088; IPR2016-01198 and IPR2016-01201; Eden, S., "How the U.S. Patent Office Got So Screwed Up," Popular Mechanics, Jun. 21, 2016, 21 pages.
Voip-Pal Exhibit 2089; IPR2016-01198 and IPR2016-01201; Quinn, G., "Supreme Court to decide if Inter Partes Review is Unconstitutional," IPWatchdog@, Jun. 12, 2017, 4 pages.
Voip-Pal Exhibit 2090; IPR2016-01198 and IPR2016-01201; Quinn, G., "Industry reaction toSCOTUS patent venue decision in *TC Heartland* v. *Kraft Food Group*," IPWatchdog@, May 22, 2017, 7 pages.
Voip-Pal Exhibit 2091; IPR2016-01198 and IPR2016-01201; Flibbert et al., "5 Distinctions Between IPRs and District Court Patent Litigation," *Finnegan*, Dec. 16, 2015, 6 pages.
Voip-Pal Exhibit 2092; IPR2016-01198 and IPR2016-01201; "2404. Hobbs Act—Under Color Of Official Right," *USAM*, Department of Justice, downloaded on Jan. 12, 2018, 5 pages.
Voip-Pal Exhibit 2093; IPR2016-01198 and IPR2016-01201; "Selection process for assigning judges to expanded PTAB panels," 717 Madison Place, Aug. 28, 2017, 3 pages.
Voip-Pal Exhibit 2094; IPR2016-01198 and IPR2016-01201; "2015 Summary Of Ethics Rules," *Economic Development Administration*, U.S. Department of Commerce, 16 pages.
Voip-Pal Exhibit 2095; IPR2016-01198 and IPR2016-01201; "Patent Trial and Appeal Board Statistics," United States Patent and Trademark Office, *USPTO*, Mar. 31, 2017, 15 pages.
Voip-Pal Exhibit 2096; IPR2016-01198 and IPR2016-01201; Madigan et al., "Turning Gold to Lead:How Patent Eligibility Doctrine is Undermining U.S. Leadership in Innovation," *George Mason Law & Economics Research Paper* No. 17-16, Mar. 30, 2017, 21 pages.
United States Patent and Trademark Office; Before the Patent Trial and Appeal Board; *Apple Inc., Petitioner*, v. *Voip-Pal.Com, Inc., Patent Owner*; Cases IPR2016-01198 and IPR2016-01201, U.S. Pat. No. 9,179,005 B2 and 8,542,815 B2; Order, Conduct of Proceeding, 37 C.F.R. § 42.5, for both proceedings; Paper No. 62, Entered: Jan. 19, 2018, 4 pages.
United States Patent and Trademark Office; Before the Patent Trial and Appealboard; *Apple Inc., Petitioner*, v. *Voip-Pal.Com, Inc., Patent Owner*; IPR2016-01198, U.S. Pat. No. 9,179,005; Notice of Appeal, Dated: Jan. 22, 2018, 5 pages.
Apple Exhibit 1022, IPR2016-01198, Telephonic Hearing Before the Administrative Patent Judges; Jan. 19, 2018; 14 pages.
United States Patent and Trademark Office; Before the Patent Trial and Appealboard; *Apple Inc., Petitioner*, v. *Voip-Pal.Com, Inc., Patent Owner*; IPR2016-01201, U.S. Pat. No. 8,542,815; Notice of Appeal, Dated: Jan. 22, 2018, 5 pages.
Apple Exhibit 1022, IPR2016-01201, Telephonic Hearing Before the Administrative Patent Judges; Jan. 19, 2018; 14 pages.
Case: 18-1456; Document: 1-1; Filed: Jan. 23, 2018, 1 page: United States Court of Appeals for the Federal Circuit; Notice of Docketing; 18-1456—*Apple Inc.* v. *Voip-Pal.com, Inc.*; Date of Docketing: Jan. 23, 2018, IPR2016-01198; 1 page.
Case: 18-1456; Document: 1-2; Filed: Jan. 23, 2018, 34 pages: United States Court of Appeals for the Federal Circuit; *Apple Inc., Petitioner*, v.*Voip-Pal.Com, Inc.*, Patent Owner; IPR2016-01198, U.S. Pat. No. 9,179,005; Notice of Appeal, (Dated: Jan. 22, 2018, 5 pages); with Paper 53; Entered: Nov. 20, 2017; Final Written Decision; 35 U.S.C. § 318(a) and 37 C.F.R. § 42.73; (29 pages).
Case: 18-1456; Document 6; Filed: Jan. 25, 2018; 14 pages: In the United States Court of Appeals for the Federal Circuit, *Apple Inc., Petitioner-Appellant*, v. *Voip-Pal.Com, Inc., Patent Owner-Appellee*. On Appeal from the United States Patent and Trademark Office, Patent Trial and Appeal Board, in Case No. IPR2016-01198; Motion of Appellant Apple Inc. To Stay Appeal or for a Limited Remand To Allow Conclusion of Administrative Proceedings.
Case: 18-1457; Document: 1-1; Filed: Jan. 23, 2018, 1 page: United States Court of Appeals for the Federal Circuit; Notice of Docketing; 18-1457—*Apple Inc.* v. *Voip-Pal.com, Inc.*; Date of Docketing: Jan. 23, 2018, IPR2016-01201; 1 page.
Case: 18-1457; Document: 1-2; Filed: Jan. 23, 2018, 34 pages: United States Court of Appeals for the Federal Circuit; *Apple Inc., Petitioner*, v. *Voip-Pal.Com, Inc., Patent Owner*; IPR2016-01201, U.S. Pat. No. 8,542,815; Notice of Appeal, (Dated: Jan. 22, 2018, 5 pages); with Paper 54; Entered: Nov. 20, 2017; Final Written Decision; 35 U.S.C. § 318(a) and 37 C.F.R. § 42.73; (29 pages).
Case: 18-1457; Document 6; Filed: Jan. 25, 2018; 14 pages: In the United States Court of Appeals for the Federal Circuit, *Apple Inc., Petitioner-Appellant*, v. *Voip-Pal.Com, Inc., Patent Owner-Appellee*. On Appeal from the United States Patent and Trademark Office, Patent Trial and Appeal Board, in Case No. IPR2016-01201; Motion of Appellant Apple Inc. To Stay Appeal or for a Limited Remand To Allow Conclusion of Administrative Proceedings.
United States Patent and Trademark Office; Before the Patent Trial and Appeal Board; *Apple Inc., Petitioner*, v. *Voip-Pal.Com, Inc., Patent Owner*; Case No. IPR2016-01198, Patent 9, 179,005; Petitioner's Reply in Support of Its Motion for Entry of Judgment in Favor of Petitioner as a Sanction for Improper Ex Parte Communications By Patent Owner, Or, Alternatively, for New and Constitutionally Correct Proceedings, Date: Jan. 26, 2018, 11 pages.
United States Patent and Trademark Office; Before the Patent Trial and Appealboard; *Apple Inc., Petitioner*, v. *Voip-Pal.Com, Inc., Patent Owner*; Case No. IPR2016-01198, U.S. Pat. No. 9,179,005; Petitioner's Updated Exhibit List, Date: Jan. 26, 2018, 4 pages.
Apple Exhibit 1023, IPR2016-01198, Voip-Pal Issues a Correction to its Press Release of Sep. 18, 2017; Jan. 12, 2018, 1 page.
United States Patent and Trademark Office; Before the Patent Trial and Appeal Board; *Apple Inc., Petitioner*, v. *Voip-Pal.Com, Inc., Patent Owner*; Case No. IPR2016-01201, U.S. Pat. No. 8,542,815; Petitioner's Reply in Support of Its Motion for Entry of Judgment in Favor of Petitioner as a Sanction for Improper Ex Parte Communications By Patent Owner, Or, Alternatively, for New and Constitutionally Correct Proceedings, Date: Jan. 26, 2018, 11 pages.
United States Patent and Trademark Office; Before the Patent Trial and Appealboard; *Apple Inc., Petitioner*, v. *Voip-Pal.Com, Inc., Patent Owner*; Case No. IPR2016-01201, U.S. Pat. No. 8,542,815; Petitioner's Updated Exhibit List, Date: Jan. 26, 2018, 4 pages.
Apple Exhibit 1023, IPR2016-01201, Voip-Pal Issues a Correction to its Press Release of Sep. 18, 2017; Jan. 12, 2018, 1 page.
Case: 18-1456; Document 7; Filed: Jan. 29, 2018; 2 pages: United States Court of Appeals for the Federal Circuit, Order; consolidating the appeals.
Case: 18-1457; Document 7; Filed: Jan. 29, 2018; 2 pages: United States Court of Appeals for the Federal Circuit, Order; consolidating the appeals.
Case 2:18-cv-00953-RFB-GWF, Document 1, Filed May 24, 2018; Voip-Pal.com, Inc. Complaint Forpatent Infringement [Jury Demand] against Defendant Apple, Inc., United States District Court, District of Nevada, 30 pages.
Case 2:18-cv-01076, Document 1, Filed Jun. 15, 18, Voip-Pal.com, Inc. Complaint for Patent Infringement [Jury Demand], United States District Court, District Of Nevada against Defendants Amazon.com, Inc. ("Amazon Inc."), Amazon Technologies, Inc. ("Amazon Technologies") and Amazon Lab126 ("Amazon Lab126" and together with Amazon Inc. and Amazon Technologies collectively referred to as the "Defendants"), 39 pages.
Case 2:18-cv-01129-RCJ-VCF; Document 6; Filed Aug. 9, 2018; 30 pages; United States Districtcourt District of Nevada, AT&T Corp's Motion To Dismiss Plaintiff's Second Amended Complaint.
Case 2:18-cv-01129-RCJ-VCF; Document 6-1; Filed Aug. 9, 2018; 3 pages: : United States District Court District of Nevada; Declaration of Lauren J. Dreyer in Support of AT&T Corp's Motion To Dismiss Plaintiff's Second Amended Complaint.
Case 2:18-cv-01129-RCJ-VCF Document 6-2 Filed Aug. 9, 2018; 8 pages: United States District Court District of Nevada; Appendix A—Asserted Claims of '005 Patent.
Case 2:18-cv-01129-RCJ-VCF Document 6-3 Filed Aug. 9, 2018; 6 pages, United States District Court District of Nevada; Appendix B—Asserted Claims of '815 Patent.

(56) References Cited

OTHER PUBLICATIONS

Case 2:18-cv-01129-RCJ-VCF Document 6-4 Filed Aug. 9, 2018; 70 pages: United Statesdistrict Court District of Nevada; Exhibit 1—War Department Field Manual for the Telephone Switchboard Operating Procedure.
Case 2:18-cv-01129-RCJ-VCF Document 6-5 Filed Aug. 9, 2018; 6 pages: United States Districtcourt District of Nevada; Exhibit 2—Transcript of "Telephone Technology—1940s—USA".
Case 2:18-cv-01129-RCJ-VCF Document 6-6 Filed Aug. 9, 2018; 79 pages: United States District Court District of Nevada; Exhibit 3—Patent Owner's Response (Paper 17), IPR 2016-01198.
Case 2:18-cv-01129-RCJ-VCF Document 6-7 Filed Aug. 9, 2018; 33 pages: United States District Court District of Nevada; Exhibit 4—Institution Decision (Paper 6), IPR2016-01198.
Case 2:18-cv-01129-RCJ-VCF Document 6-8 Filed Aug. 9, 2018; 6 pages: United States District Court District of Nevada; Exhibit 5, 34 pages: Institution Decision (Paper 6), IPR2016-01201.
Case 2:18-cv-01129-RCJ-VCF, Document 14, Filed Sep. 6, 2018; 39 pages: United States District Court District of Nevada, Plaintiff Voip-Pal's Opposition To At&T Corp's Motion To Dismiss Plaintiff's Second Amended Complaint.
Case 2:16-cv-00271-RCJ-VCF, Document 68, Filed Aug. 9, 2018; 30 pages: United States District Court District of Nevada; Verizon Wireless's Motion To Dismiss Plaintiff's Second Amended Complaint.
Case 2:16-cv-00271-RCJ-VCF, Document 68-1, Filed Aug. 9, 2018, 225 pages: United States District Court District of Nevada; Exhibit A—Declaration of Megan S. Woodworth in Support of Verizon Wireless's Motion to Dismiss Plaintiff's Second Amended Complaint.
Case 2:16-cv-00271-RCJ-VCF, Document 68-2, Filed Aug. 9, 2018, 8 pages: United States District Court District of Nevada; Appendix A: Asserted Claims of '005 Patent.
Case 2:16-cv-00271-RCJ-VCF, Document 68-3, Filed Aug. 9, 2018, 6 pages: United States District Court District of Nevada; Appendix B: Asserted Claims of '815 Patent.
Case 2:16-cv-00271-RCJ-VCF, Document 82, Filed Sep. 7, 2018; 39 pages: United States District Court District of Nevada; Plaintiff Voip-Pal's Opposition To Verizon's Motion To Dismiss Plaintiff's Second Amended Complaint (Corrected Brief).
Case No. 2:16-cv-00271-RCJ-VCF, Document 79, filed on Sep. 6, 2018, Motion for Leave to Amend/Correct [10] Amended Complaint, by *Plaintiff Voip-Pal.com, Inc., in Voip-Pal.com, Inc. v. Verizon Wireless Services, LLC et al.* (11 pages).
Case No. 2:16-cv-00271-RCJ-VCF, Document 79-1, filed on Sep. 6, 2018, Exhibit to Motion for Leave to Amend/Correct [10] Amended Complaint, by *Plaintiff Voip-Pal.com, Inc., in Voip-Pal.com, Inc. v. Verizon Wireless Services, LLC et al.*, namely, Third Amended Complaint for Patent Infringement (148 pages).
Case No. 2:18-cv-01129-RCJ-VCF, Document 12, filed on Sep. 6, 2018, Motion for Leave to Amend/Correct Amended Complaint,, by *Plaintiff Voip-Pal.com, Inc., in Voip-Pal.com, Inc. v. AT&T Corp.* (11 pages).
Case No. 2:18-cv-01129-RCJ-VCF, Document 12-1, filed on Sep. 6, 2018, Exhibit to Motion to Amend/Correct [3] Amended Complaint,, by *Plaintiff Voip-Pal.com, Inc., in Voip-Pal.com, Inc. v. AT&T Corp.*, namely, Third Amended Complaint for Patent Infringement (147 pages).
Case No. 2:16-cv-00271-RCJ-VCF, Document 13, filed Sep. 6, 2018, Motion to Strike [6] Motion to Dismiss, by *Plaintiff Voip-Pal.com, Inc., in Voip-Pal.com, Inc. v. AT&T Corp.* (15 pages).
Case No. 2:16-cv-00271-RCJ-VCF, Document 80, filed Sep. 6, 2018, Motion to Strike [68] Motion to Dismiss, by *Plaintiff Voip-Pal.com, Inc., in Voip-Pal.com, Inc. v. Verizon Wireless Services, LLC et al.* (15 pages).
Mark Spencer, et al., The Asterisk Handbook, Mar. 30, 2003, 71 pages, Version 2, Digium, Inc., United States.
Andrew Cray, Ip PBXs: Open Questions, Data Communications, The Global Magazine for Network Architects, pp. 1, 114, 69-84, Mar. 1999, United States.

Jim Van Meggelen, et al., Asterisk: The Future of Telephony, Aug. 31, 2005, 376 pages, O'Reilly Media, Inc., United States.
David Gomillion, et al., Building Telephony Systems with Asterisk, Sep. 2005, 174 pages, Packt Publishing, United Kingdom.
Paul Mahler., Voip Telephony with Asterisk, 2004, 211 pages, Signate, United States.
Avaya Inc., Understanding VoIP, Leveraging Technology for a Competitive Edge, White Paper, Oct. 2005, 31 pages, Avaya Inc., United States.
Avaya Inc., Feature Description and Implementation for Avaya Communication Manager, Issue 3, Jun. 2005, 1444 pages, Avaya Inc., United States.
Avaya Inc., Administration Guide for Avaya Communication Manager, Issue 1, Jun. 2005, 1656 pages, Avaya Inc., United States.
Avaya Inc., Configuring Avaya Communication Manager with a Multi Location Dial Plan - Issue 1.0, Avaya Solution & Interoperability Test Lab, Mar. 18, 2004, 18 pages, Avaya Inc., United States.
Avaya Inc., Application Notes for H.323 Voice over IP Trunking between Avaya Communication Manager and VoIP Americas Nativevoip VOIP Service—Issue 1.0, Avaya Solution & Interoperability Test Lab, 2005, 13 pages, Avaya Inc., United States.
Avaya Inc., Configuring H.323 Signaling and IP Trunks between Avaya Communication Manager and Cisco CallManager 4.0 - Issue 1.0, Avaya Solution & Interoperability Test Lab, 2005, 19 pages, Avaya Inc., United States.
John Alexander, et al., A Cisco AVVID Solution, Cisco CallManager Fundamentals, 2002, 722 pages, Cisco Press, United States.
John Alexander, et al., Cisco CallManager Fundamentals, Second Edition, 2006, 975 pages, Cisco Systems, Inc., United States.
Salvatore Collora et al., A Cisco AVVID Solution, Cisco CallManager Best Practices, 2004, 620 pages, Cisco Systems, Inc., United States.
Cisco Systems, Inc., Cisco IP Telephony Network Design Guide, Cisco CallManager Release 3.0(5), 2000, 262 pages, Cisco Systems, Inc., United States.
David Bateman, Configuring CallManager and Unity: A Step-by-Step Guide, 2005, 560 pages, Cisco Press, United States.
Cisco Systems, Inc., System Description for the Cisco Communications Network, Version 2.1, Jan. 1999, 42 pages, Cisco Systems, Inc., United States.
Web-Page, http://www.vonage.com/no_flash/features.php?feature=3 way_ calling, as accessed Nov. 6, 2004, 1 page, Vonage Holdings Corp, United States.
Web-Page, http://www.vonage.com/no_flash/features.php?feature=7_dig it_ dialing, as accessed Nov. 6, 2004, 1 page, Vonage Holdings Corp, United States.
Web-Page, http://www.vonage.com/no_flash/features.php?feature=311, as accessed Nov. 6, 2004, 2 pages, Vonage Holdings Corp, United States.
Web-Page, http:// www.vonage.com/no_flash/features.php?feature=subscriber_to_subscriber, as accessed Apr. 6, 2005, 1 page, Vonage Holdings Corp, United States.
Baset et al., An Analysis of the Skype Peer-to-Peer Internet Telephony Protocol, Sep. 15, 2004, 12 pages, Department of Computer Science, Columbia University, United States.
Hao Wang, Skype VoIP service- architecture and comparison, INFOTECH Seminar Advanced Communication Services (ACS), 2005, 10 pages, Institute of Communication Networks and Computer Engineering, University of Stuttgart, Germany.
Dennis Bergström, An analysis of Skype VoIP application for use in a corporate environment., http://www.geocities.com/bergstromdennis/, Oct. 28, 2004, 30 pages, Version 1.3, United States.
Web-Page, Skype Out, http://www.skype.com/products/skypeout/, as accessed Jan. 27, 2005, 2 pages, Skype Technologies S.A., Luxembourg.
Web-Page, Skype for Windows, http://www.skype.com/products/skype/windows/, as accessed Jan. 19, 2005, 1 page, Skype Technologies S.A., Luxembourg.
Web-Page, http://www.skype.com/help/guides/remove.html, as accessed Jan. 25, 2005, 1 page, Skype Technologies S.A., Luxembourg.
Web-Page, How to Use Skype, http://www.skype.com/help/guides/usingskype.html, as accessed Jan. 27, 2005, 5 pages, Skype Technologies S.A., Luxembourg.

(56) References Cited

OTHER PUBLICATIONS

Web-Page, How to Use SkypeOut, http://www.skype.com/help/guides/skypeout.html, as accessed Jan. 27, 2005, 2 pages, Skype Technologies S.A., Luxembourg.
Web-Page, http://www.skype.com/, as accessed Jan. 30, 2005, 3 pages, Skype Technologies S.A., Luxembourg.
Web-Page, Skype for Windows 1.4, http://www.skype.com/products/skype/windows/, as accessed Oct. 26, 2005, 1 page, Skype Technologies S.A., Luxembourg.
Web-Page, http://www.skype.com/help/guides/call.html, as accessed Oct. 26, 2005, 1 page, Skype Technologies S.A., Luxembourg.
Web-Page, How to Use Skype, http://www.skype.com/help/guides/usingskype.html, as accessed Oct. 27, 2005, 5 pages, Skype Technologies S.A., Luxembourg.
Web-Page, How to Use SkypeOut, http://www.skype.com/help/guides/skypeout.html, as accessed Oct. 26, 2005, 2 pages, Skype Technologies S.A., Luxembourg.
Web-Page, http://www.skype.com/products/, as accessed Oct. 30, 2005, 3 pages, Skype Technologies S.A., Luxembourg.
Canadian Office Action dated Jan. 15, 2020 for Canadian Patent Application No. CA 3,032,707.
Canadian Office Action dated Jun. 15, 2020 for Canadian Patent Application No. CA 3,045,681.
Canadian Office Action dated Jun. 22, 2020 for Canadian Patent Application No. CA 3,045,683.
Canadian Office Action dated Jun. 15, 2020 for Canadian Patent Application No. CA 3,045,694.
European Examination Report dated May 26, 2020 for European Patent Application No. 18 174 930.0.
Third Amended Complaint for Patent Infringement, *VoIP-Pal.com, Inc.* v. *AT&T Corp.*, United States District Court Northern District of California, Case No. 5:18-cv-06177, filed Nov. 15, 2018, 26 pages.
Third Amended Complaint for Patent Infringement, *VoIP-Pal.com, Inc.* v. *Cellco Partnership d/b/a Verizon Wireless et al.*, United States District Court Northern District of California, Case No. 5:18-cv-06054, filed Nov. 15, 2018, 25 pages.
Joint Case Management Statement and [Proposed] Order, U.S. District Court Northern District of California, in *VoIP-Pal.com, Inc.* v. *Twitter, Inc.*, Case No. 18-cv-04523; *VoIP-Pal.com, Inc.* v. *Cellco Partnership d/b/a Verizon Wireless*, Case No. 18-cv-06054, *VoIP-Pal.com, Inc.* v. *AT&T Corp.*, Case No. 3:18-cv-06177, *VoIP-Pal.com, Inc.* v. *Apple Inc.*, Case No. 3:18-cv-06216 and Case No. 3:18-cv-06217, *VoIP-Pal.com, Inc.* v. *Amazon.com, Inc et al.*, Case No. 3:18-cv-07020, Jan. 9, 2019, 29 pages.
Defendants' Consolidated Notice Of Motion And Motion To Dismiss Plaintiff's Complaint; Memorandum Of Points And Authorities In Support, U.S. District Court Northern District of California, in *VoIP-Pal.com, Inc.* v. *Twitter, Inc et al.*, Case Nos. 18-cv-04523, 18-cv-06054, 3:18-cv-06177, 3:18-cv-06217, re: U.S. Pat. Nos. 8,542,815 and 9,179,005, Jan. 10, 2019, 34 pages.
VoIP-Pal's Opposition To Defendants' Consolidated Motion To Dismiss Plaintiff's Complaint: Memorandum Of Points And Authorities In Support, U.S. District Court Northern District of California, in *VoIP-Pal.com, Inc.* v. *Twitter, Inc et al.*, Case Nos. 18-cv-04523, 18-cv-06054, 18-cv-06177, 18-cv-06217, Feb. 7, 2019, 33 pages.
Declaration of William Henry Mangione-Smith in Support of VoIP-Pal's Opposition to Defendants' Consolidated Motion to Dismiss Plaintiff's Complaint: Memorandum of Pints and Authorities in Support. U.S. District Court Northern District of California, in *VoIP-Pal.com, Inc.* v. *Twitter, Inc et al.*, Case Nos. 18-cv-04523, 18-cv-06054, 18-cv-06177, 18-cv-06217, Feb. 7, 2019, 37 pages.
VoIP-Pal's Opposition To Defendants' Consolidated Motion To Dismiss Plaintiff's Complaint: Memorandum Of Points And Authorities In Support (Corrected), U.S. District Court Northern District of California, in *VoIP-Pal.com, Inc.* v. *Twitter, Inc et al.*, Case Nos. 18-cv-04523, 18-cv-06054, 18-cv-06177, 18-cv-06217, Feb. 12, 2019, 33 pages.
Defendants' Consolidated Reply in Support of Defendants' Consolidated Motion To Dismiss Plaintiff's Complaint; Memorandum Of Points And Authorities In Support, U.S. District Court Northern District of California, in *VoIP-Pal.com, Inc.* v. *Twitter, Inc et al.*, Case Nos. 18-cv-04523, 18-cv-06054, 18-cv-06177, 18-cv-06217, Feb. 28, 2019, 24 pages.
Order Granting Consolidated Motions to Dismiss, United States District Court Northern District of California, in *VoIP-Pal.com, Inc.* v. *Twitter, Inc et al.*, Case Nos. 18-cv-04523, 18-cv-06054, 18-cv-06177, 18-cv-06217, re: U.S. Pat. Nos. 8,542,815 and 9,179,005, Document 96, Judge Lucy H. Koh, Mar. 25, 2019, 45 pages.
Corrected Opening Brief For Plaintiff-Appellant, On Appeal from the United States District Court for the Northern District of California in Nos. 5:18-cv-04523-LHK (Twitter, Inc.), 5:18-cv-06054-LHK (CellcoPartnership d/b/a Verizon Wireless), Case No. 18-cv-06054 (Verizon), 5:18-cv-06177-LHK (AT&T) and 5:18-cv-06217-LHK (Apple), U.S. Court of Appeals for the Federal Circuit ("CAFC"), Jul. 9, 2019, 241 pages (including Addendum).
Joint Responsive Brief For Defendants-Appellees, CAFC, On Appeal from the United States District Court for the Northern District of California, Case Nos. 5:18-cv-04523-LHK, 5:18-cv-06054-LHK, 5:18-cv-06177-LHK, and 5:18-cv-06217-LHK, Document 46, Aug. 5, 2019, 78 pages.
Reply Brief for Plaintiff-Appellant, U.S. Court of Appeals for the Federal Circuit, On Appeal from theUnited States District Court for the Northern District of California in Nos. Case Nos. 5:18-cv-04523-LHK, 5:18-cv-06054-LHK, 5:18-cv-06177-LHK and 5:18-cv-06217-LHK, Sep. 9, 2019, 40 pages.
Judgment (Rule 36), Per Curiam (Newman, Lourie, and O'Malley, Circuit Judges), U.S. Court of Appeals for the Federal Circuit, in Appeal from the United States District Court for the Northern Districtof California in Case Nos. 5:18-cv-04523-LHK (Twitter, Inc., 2019-1808), 5:18-cv-06054-LHK (Cellco Partnership, DBA Verizon Wireless Services LLC, 2019-1812), 5:18-cv-06177-LHK (AT&T Corp., 2019- 1813), 5:18-cv-06217-LHK (Apple, 2019-1814), Document 88, Mar. 16, 2020 (4 pages).
Appellant's Combined Petition for Panel Rehearing and Rehearing En Banc, United States Court of Appeals for the Federal Circuit, Appeal from the United States District Court for the Northern District of California in Case Nos. 5:18-cv-04523-LHK, 5:18-cv-06054-LHK, 5:18-cv-06177-LHK and 5:18-cv-06217-LHK, Document 89, Apr. 15, 2020, 34 pages.
Order Denying Petition, On Petition For Panel Rehearing And Rehearing En Banc, Document 99, U.S. Court of Appeals for the Federal Circuit, Peter R. Marksteiner, Clerk of Court, May 18, 2020 (3 pages).
Case Management Order, Judge Lucy H. Koh, United States District Court Northern District of California, *VoIP-Pal.com, Inc.* v. *Amazon.com Inc, et al.*, Case No. 5:18-CV-7020-LHK, *VoIP-Pal.com, Inc.* v. *Apple, Inc.*, Case No. 18-CV-06216-LHK, Document 40, Jan. 16, 2019, 3 pages.
Apple's and Amazon's Consolidated Notice of Motion and Motion to Dismiss Plaintiff's Complaint; Memorandum Of Points And Authorities In Support, Case Nos. 18-cv-06216-LHK, 18-cv-07020-LHK, re: U.S. Patent Nos. 9,826,002, 9,948,549, 9,813,330, and 9,537,762, United States District Court Northern District of California, Document 57, Feb. 15, 2019, 32 pages.
First Amended Complaint, *VoIP-Pal.com, Inc.* v. *Amazon.com, Inc et al.*, Case No. 5:18-cv-07020-LHK,United States District Court Northern District of California, re: U.S. Pat. Nos. 9,826,002, 9,948,549, 9,813,330, and 9,537,762, Mar. 8, 2019, 52 pages.
First Amended Complaint, VoIP-Pal.com, Inc. v. Apple, Inc., Case No. 5:18-cv-06216-LHK, United States District Court Northern District of California, re: U.S. Patent Nos. 9,826,002, 9,948,549, 9,813,330, and 9,537,762, Mar. 8, 2019, 44 pages.
VoIP-Pal's Opposition to Apple's and Amazon's Consolidated Motion to Dismiss Plaintiff's Complaint: Memorandum of Points and Authorities in Support, Case No. 5:18-cv-06216-LHK, United States District Court Northern District of California, Document 68, Mar. 15, 2019, 33 pages.
Declaration of William Henry Mangione-Smith in Support of VoIP-Pal's Opposition to Defendants' Consolidated Motion to Dismiss Plaintiff's Complaint, Case Nos. 18-cv-06216-LHK, 18-cv-07020-LHK, United States District Court Northern District of California, Document 49-7, Mar. 15, 2019, 35 pages.

(56) References Cited

OTHER PUBLICATIONS

Reply of Defendants in Support of Their Consolidated Motion to Dismiss Plaintiff's Complaints, Case Nos. 5:18-cv-06216-LHK, 5:18-cv-07020-LHK, United States District Court Northern District of California, Document 53, Apr. 5, 2019, 21 pages.

Patent L.R. 4-2 Identification Of Preliminary Proposed Constructions And Extrinsic Evidence Of Apple Inc., Amazon.com, Inc., and Amazon Technologies, Inc., Case Nos. 5:18-cv-06216-LHK, 5:18-cv-07020-LHK, United States District Court Northern District of California, Apr. 22, 2019, 42 pages.

Consolidated Notice Of Motion And Motion of Apple and Amazon To Dismiss Plaintiff's Amended Complaint; Memorandum Of Points And Authorities In Support, Case Nos. 18-cv-06216-LHK, 18-cv-07020-LHK, U.S. District Court Northern District of California, Document 67, Jun. 5, 2019, 31 pages.

Corrected) VoIP-Pal's Opposition to Apple's and Amazon's Consolidated Motion to Dismiss Plaintiff's Complaint: Memorandum of Points And Authorities In Support, Case Nos. 18-cv-06216-LHK, 18-cv-07020-LHK, U.S. District Court Northern District of California, Jun. 19, 2019, 33 pages.

Reply of Defendants in Support of Their Consolidated Motion to Dismiss Plaintiff's Amended Complaints, Case Nos. 18-cv-06216-LHK, 18-cv-07020-LHK, United States District Court Northern District of California, Document 70, Jun. 26, 2019, 20 pages.

VoIP-Pal's Opening Claim Construction Brief, Case Nos. 5:18-cv-06216-LHK and 5:18-cv-07020-LHK, United States District Court Northern District of California, Jul. 15, 2019, 24 pages.

Defendants' Responsive Claim Construction Brief, Case Nos. 5:18-cv-06216-LHK, 5:18-cv-07020-LHK, United States District Court Northern District of California, Document 94, Aug. 2, 2019, 30 pages.

VoIP-Pal's Reply Claim Construction Brief, Case Nos. 5:18-cv-06216-LHK and 5:18-cv-07020-LHK, United States District Court Northern District of California, Aug. 9, 2019, 19 pages.

Order Granting Consolidated Motions to Dismiss With Prejudice, U.S. District Court Northern District of California, in *VoIP-Pal.com, Inc. v. Apple, Inc et al.*, Case Nos. 18-cv-06216-LHK, 18-cv-07020-LHK, Document 84, Judge Lucy H. Koh, Nov. 1, 2019, 68 pages.

Appellant's Opening Brief and Addendum, Docket Nos. 20-1241, 20-1244, U.S. Court of Appeals for the Federal Circuit ("CAFC"), Appeal from the U.S. District Court for the Northern District of California in Case Nos. 5:18-cv-06216-LHK, 5:18-cv-07020-LHK, Document 16, Feb. 24, 2020, 231 pages.

Joint Response Brief for Appellees, U.S. Court of Appeals for the Federal Circuit ("CAFC"), Case Nos. 2020-1241, 2020-1244, Appeal from the U.S. District Court for the Northern District of California in Case Nos. 5:18-cv-06216-LHK and 5:18-cv-07020-LHK, Document 21, May 6, 2020, 76 pages.

Appellant's Reply Brief, U.S. Court of Appeals for the Federal Circuit ("CAFC"), Case Nos. 2020-1241, 2020-1244, Appeal from the United States District Court for the Northern District of California in Case Nos. 5:18-cv-06216-LHK and 5:18-cv-07020-LHK, Document 26, Jun. 10, 2020, 43 pages.

Original Complaint for Patent Infringement, *VoIP-Pal.com, Inc. v. Facebook, Inc. and WhatsApp, Inc.*, Case No. 6:20-cv-00267, U.S. District Court for the Western District of Texas, Apr. 2, 2020, 29 pages.

Exhibit 2, in support of Original Complaint for Patent Infringement, Case No. 6:20-cv-00267, U.S. District Court for the Western District of Texas, Apr. 2, 2020, 11 pages.

Original Complaint for Patent Infringement, *VoIP-Pal.com, Inc. v. Google, LLC*, Case No. 6:20-cv-00269, U.S. District Court for the Western District of Texas, Apr. 3, 2020, 28 pages.

Exhibit 2, in support of Original Complaint for Patent Infringement, Case No. 6:20-cv-00269, U.S. District Court for the Western District of Texas, Apr. 3, 2020, 19 pages.

Original Complaint for Patent Infringement, *VoIP-Pal.com, Inc. v. Amazon.com, Inc et al.*, Case No. 6:20-cv-00272, U.S. District Court for the Western District of Texas, Apr. 6, 2020, 28 pages.

Exhibit 2, in support of Original Complaint for Patent Infringement, Case No. 6:20-cv-00272, U.S. District Court for the Western District of Texas, Apr. 6, 2020, 10 pages.

Original Complaint for Patent Infringement, *VoIP-Pal.com, Inc. v. Apple, Inc.*, Case No. 6:20-cv-00275, U.S. District Court for the Western District of Texas, Apr. 7, 2020, 28 pages.

Exhibit 2, in support of Original Complaint for Patent Infringement, Case No. 6:20-cv-00275, U.S. District Court for the Western District of Texas, Apr. 7, 2020, 15 pages.

Original Complaint for Patent Infringement, *VoIP-Pal.com, Inc. v. AT&T, Inc. et al.*, Case No. 6:20-cv-00325, U.S. District Court for the Western District of Texas, Apr. 24, 2020, 29 pages.

Exhibit 2, in support of Original Complaint for Patent Infringement, Case No. 6:20-cv-00325, U.S. District Court for the Western District of Texas, Apr. 24, 2020, 9 pages.

Original Complaint for Patent Infringement, *VoIP-Pal.com, Inc. v. Verizon Communications, Inc et al.*, Case No. 6:20-cv-00327, U.S. District Court for the Western District of Texas, Apr. 24, 2020, 29 pages.

Exhibit 2, in support of Original Complaint for Patent Infringement, Case No. 6:20-cv-00327, U.S. District Court for the Western District of Texas, Apr. 24, 2020, 11 pages.

Order, Granting-in-Part Petitioner's Motion for Sanctions, *Apple Inc. v. VoIP-Pal.com, Inc..*, Case Nos. IPR2016-01198 and IPR2016-012011 re: U.S. Pat. No. 9,179,005 B2 and 8,542,815 B2. Before the USPTO Patent Trial and Appeal Board ("PTAB"), Per Administrative Patent Judges Scott R. Boalick, Jacqueline Wright Bonilla, and Michael P. Tierney, Paper No. 70, Dec. 21, 2018, 18 pages.

Petitioner's Request for Rehearing, *Apple Inc. v. VoIP-Pal.com, Inc.*, Case No. IPR2016-01198 (PTAB), re: U.S. Pat. No. 9,179,005, Paper 71, Jan. 8, 2019, 21 pages.

Petitioner's Request for Rehearing, *Apple Inc. v. VoIP-Pal.com, Inc.*, Case No. IPR2016-01201 (PTAB), re: U.S. Pat. No. 8,542,815, Paper 71, Jan. 8, 2019, 21 pages.

Patent Owner's Opposition to Apple's Request for Rehearing Pursuant to Board Order of Dec. 21, 2018 (Corrected), PTAB Case No. IPR2016-01198, U.S. Pat. No. 9,179,005, Paper 73, Jan. 22, 2019, 26 pages.

Patent Owner's Opposition to Apple's Request for Rehearing Pursuant to Board Order of Dec. 21,|2018 (Corrected), PTAB Case No. IPR2016-01201, U.S. Pat. No. 8,542,815, Paper 73, Jan. 22, 2019, 26 pages.

Petitioner Reply In support of Its Request for Rehearing, PTAB Case No. IPR2016-01198, U.S. Pat. No. 9,179,005, Paper 74, Jan. 29, 2019, 13 pages.

Petitioner Reply In support of Its Request for Rehearing, PTAB Case No. IPR2016-01201, U.S. Pat. No. 8,542,815, Paper 74, Jan. 29, 2019, 13 pages.

Decision Denying Petitioner's Request for Rehearing, *Apple Inc. v. VoIP-Pal.com, Inc.*, Case Nos. IPR2016-01198 and IPR2016-012011 re: U.S. Patents 9,179,005 B2 and 8,542,815 B2. Before the USPTO Patent Trial and Appeal Board ("PTAB"), Per Administrative Patent Judges Scott R. Boalick, Jacqueline Wright Bonilla, and Michael P. Tierney, Paper No. 75, May 24, 2019, 12 pages.

Principal Brief for Apple Inc. as Appellant, Docket Nos. 18-1456, 18-1457, U.S. Court of Appeals for theFederal Circuit ("CAFC"), On Appeal from the USPTO, Patent Trial and Appeal Board, in Case Nos. IPR2016-01198, IPR2016-01201, Document 28, Sep. 23, 2019, 69 pages.

Opening Brief for Appellee, Docket Nos. 18-1456, 18-1457, U.S. Court of Appeals for the Federal Circuit ("CAFC"), On Appeal from the USPTO, Patent Trial and Appeal Board, in Case Nos. IPR2016-01198, IPR2016-01201, Nov. 4, 2019, 69 pages.

Reply Brief for Apple Inc. as Appellant, Docket Nos. 18-1456, 18-1457, U.S. Court of Appeals for the Federal Circuit ("CAFC"), On Appeal from the USPTO, Patent Trial and Appeal Board, in Case Nos. IPR2016-01198, IPR2016-01201, Document 53, Feb. 24, 2020, 41 pages.

Petition for Inter Partes Review of U.S. Pat. No. 9,537,762, *Apple Inc. v. VoIP-Pal.com, Inc.*, IPR2019-01003, May 13, 2019, 71 pages.

(56) References Cited

OTHER PUBLICATIONS

Declaration of Dr. Tal Lavian, in support of Apple's Petition in IPR2019-01003 re: U.S. Pat. No. 9,537,762, *Apple, Inc.* v. *VoIP-Pal.com, Inc.*, EX1005 (Exhibit 1005), May 13, 2019, 215 pages.
Petition for Inter Partes Review of U.S. Pat. No. 9,813,330, *Apple, Inc.* v. *VoIP-Pal.com, Inc.*, IPR2019-01006, May 13, 2019, 69 pages.
Declaration of Dr. Tal Lavian, in support of Apple's Petition in IPR2019-01006 re: U.S. Pat. No. 9,813,330, *Apple, Inc.* v. *VoIP-Pal.com, Inc.*, EX1005 (Exhibit 1005), May 13, 2019, 215 pages.
Petition for Inter Partes Review of U.S. Pat. No. 9,826,002, *Apple, Inc.* v. *VoIP-Pal.com, Inc.*, IPR2019-01008, May 13, 2019, 67 pages.
Declaration of Dr. Tal Lavian, in support of Apple's Petition in IPR2019-01008 re: U.S. Pat. No. 9,826,002, *Apple, Inc.* v. *VoIP-Pal.com, Inc.*, EX1005 (Exhibit 1005), May 13, 2019, 215 pages.
Petition for Inter Partes Review of U.S. Pat. No. 9,948,549, *Apple, Inc.* v. *VoIP-Pal.com, Inc.*, IPR2019-01009, May 13, 2019, 70 pages.
Declaration of Dr. Tal Lavian, in support of Apple's Petition in IPR2019-01009 re: U.S. Pat. No. 9,948,549, *Apple, Inc.* v. *VoIP-Pal.com, Inc.*, EX1005 (Exhibit 1005), May 13, 2019, 215 pages.
*Apple, Inc.* v. *VoIP-Pal.com, Inc.*, IPR2019-01003, Paper 7 (PTAB, Nov. 12, 2019) (Decision Denying Institution of Inter Partes Review of U.S. Pat. No. 9,537,762), 21 pages.
*Apple, Inc.* v. *VoIP-Pal.com, Inc.*, IPR2019-01006, Paper 7 (PTAB, Nov. 12, 2019) (Decision Denying Institution of Inter Partes Review of U.S. Pat. No. 9,813,330), 22 pages.
*Apple, Inc.* v. *VoIP-Pal.com, Inc.*, IPR2019-01008, Paper 7 (PTAB, Nov. 12, 2019) (Decision Denying Institution of Inter Partes Review of U.S. Pat. No. 9,826,002), 22 pages.
*Apple, Inc.* v. *VoIP-Pal.com, Inc.*, IPR2019-01009, Paper 7 (PTAB, Nov. 12, 2019) (Decision Denying Institution of Inter Partes Review of U.S. Pat. No. 9,948,549), 21 pages.
Declaration of Dr. Vijay Madisetti, in WDTX Case No. 6:20-cv-00267-ADA, *VoIP-Pal.com* v. *Meta Platforms Inc. and Whatsapp LLC*, Mar. 10, 2022, 17 pages.
Joint Claim Construction and Prehearing Statement in NDCA Case No. 5:18-cv-06216-LHK, *VoIP- Pal.com, Inc.* v *Apple Inc et al.*, May 17, 2019, 246 pages.
J. Postel, RFC 768, "User Datagram Protocol", ISI, Aug. 1980, 3 pages, https://tools.ietf.org/pdf/rfc768.pdf.
J. Postel et al., RFC 793, "Transmission Control Protocol: DARPA Internet Program Protocol Specification," Sep. 1981, 89 pages, https://tools.ietf.org/pdf/rfc768.pdf.
J. Postel, RFC 821, "Simple Mail Transfer Protocol", ISI, Aug. 1982, 70 pages, https://tools.ietf.org/pdf/rfc821.pdf.
J. Mogul, J. Postel, RFC 950, "Internet Standard Subnetting Procedure," Aug. 1985, 18 pages, https://tools.ietf.org/pdf/rfc950.pdf.
H. Schulzrinne et al., RFC 1889, "Rtp: A Transport Protocol for Real-Time Applications," Jan. 1996, 75 pages, https://tools.ietf.org/pdf/rfc1889.pdf.
P. Falstrom, Cisco Systems Inc., RFC 2916, "E.164 number and DNS," Sep. 2000, 10 pages, https://tools.ietf.org/pdf/rfc2916.pdf.
R. Stewart et al., RFC 2960, "Stream Control Transmission Protocol," Oct. 2000, 134 pages, https://tools.ietf.org/pdf/rfc2960.pdf.
G. Sidebottom et al., RFC 3332, "Signaling System 7 (SS7) Message Transfer Part 3 (MTP3)—User Adaptation Layer (M3UA)," Sep. 2002, 120 pages, https://tools.ietf.org/pdf/rfc3332.pdf.
G. Camarillo et al., RFC 3398, "Integrated Services Digital Network (ISDN) User Part (ISUP) to Session Initiation Protocol (SIP) Mapping," Dec. 2002, 68 pages, https://tools.ietf.org/pdf/rfc3398.pdf.
F. Andreasen et al., Cisco Systems, RFC 3435, "Media Gateway Control Protocol (MGCP)—Version 1.0," Jan. 2003, 210 pages, https://tools.ietf.org/pdf/rfc3435.pdf.
M. Foster et al., NeuStar, Inc., RFC 3482, "No. Portability in the Global Switched Telephone Network (GSTN): An Overview," Feb. 2003, 30 pages, https://tools.ietf.org/pdf/rfc3482.pdf.

ITU-T Recommendation H.225.0, "Call signalling protocols and media stream packetization for packet-based multimedia communication systems," 1996, https://www.itu.int/rec/T-REC-H.225.0.
ITU-T Recommendation H.245, "Control protocol for multimedia communication," 1996, https://www.itu.int/rec/T-REC-H.245/en.
ITU-T Recommendation H.248.1, "Gateway control protocol," 2002, https://www.itu.int/rec/T-REC-H.248.1.
ITU-T Recommendation H.323, "Packet-based multimedia communications systems," 1996, https://www.itu.int/rec/T-REC-H.323/.
ITU-T Recommendation X.500, "Information technology - Open Systems Interconnection - The Directory: Overview of concepts, models and services," 1988, https://www.itu.int/rec/T-REC-X.500.
Bellcore, "Bell Communications Research Specification of Signalling System No. 7" (Bell Communications Research Specification of SS7), GR-246-CORE, Issue 3, 2644 pages, Dec. 1998.
Performance Technologies, Inc., "Tutorial on Signaling System 7 (SS7)," SS7 Tutorial by Performance Technologies (www.pt.com), 23 p. 2003.
Huitema et al., "An Architecture for Residential Internet Telephony Service," IEEE Network, May/Jun. 1999, 7 pages.
Lucent Technologies, "Definity System's Little Instruction Book for Basic Administration," Apr. 2000, 124 pages.
Cisco Systems, "Enhanced Gatekeeper Solutions Using GKTMP/API", White Paper, 2000, 12 pages.
Anerousis et al., "TOPS: An Architecture for Telephony over Packet Networks," IEEE Journal on Selected Areas in Communications, vol. 17, No. 1, Jan. 1999 (18 pages).
Anonymous, "What Is ENUM?", Network World, IDG Communications, May 11, 2004, as downloaded Sep. 3, 2020 from: https://www.networkworld.com/article/2332977/lan-wan-what-is-enum.html (8 pages).
Cisco Systems, "Cisco Gatekeeper External Interface Reference, Version 4.2," Cisco IOS Release 12.2(15)T, Mar. 2003 (146 pages).
Don Brown, "Unified Communications Using Communite," White Paper, Interactive Intelligence, May 1, 2002 (24 pages).
Vonexus, "Microsoft-based IP PBX Communications Solution: Enterprise Interaction Center," Vonexus (a wholly-owned subsidiary of Interactive Intelligence Inc., Jul. 2004 (4 pages).
Donald E. Brown, "The Interaction Center Platform," White Paper, Interactive Intelligence, Feb. 18, 2003 (35 pages).
Interactive Intelligence, Inc., "Interaction Director Technical Overview," Interaction Center 1.3, 2.1, and 2.2, Interactive Intelligence, 2003 (35 pages).
Interactive Intelligence, Inc., "Interaction SIP Proxy," Datasheet, Interactive Intelligence, Feb. 2004 (2 pages).
Bob Roaten, "IP Telephony and Eic: A Technical Overview," White Paper, Interactive Intelligence, Jul. 22, 1998 (9 pages).
David Fuller, "IP Telephony and the Interaction Center Platform," White Paper, Interactive Intelligence, Sep. 25, 2003 (29 pages).
"Exhibit A, Claim Constructions To Which The Parties Have Agreed," *VoIP-Pal.com, Inc.* v. *Apple Inc.*; *VoIP-Pal.com, Inc.* v. *Amazon.com, Inc.*, United States District Court for the Northern District of California (Case Nos. 18-cv-6216-LHK and -7020-LHK), May 17, 2019 (240 pages).
"Voip-Pal's Opening Claim Construction Brief", *VoIP-Pal.com, Inc.* v. *Apple Inc.*; Case No. 5:18-cv-06216-LHK, *VoIP-Pal.com, Inc.* v. *Amazon.Com and Amazon Technologies, Inc.*, Case No. 5:18-cv-07020-LHK, Jul. 15, 2019 (24 pages).
"Voip-Pal's Reply Claim Construction Brief", *VoIP-Pal.com, Inc.* v. *Apple Inc.*; Case No. 5:18-cv-06216-LHK, Aug. 9, 2019 (19 pages).
"Voip-Pal's Preliminary Claim Constructions and Identification of Supporting Evidence (Patent L.R. 4-2)", *Twitter Inc.* v. *VoIP-Pal.com, Inc.*, *Apple Inc.* v. *VoIP-Pal.com, Inc.*; *AT&T Corp., AT&T Services, Inc., and AT&T Mobility LLC* v. *VoIP-Pal.com, Inc.*, Case No. 5:20-cv-02397-LHK, Jun. 30, 2021 (18 pages).
"Plaintiffs' Opening Claim Construction Brief Oral Argument Requested Jury Trial Demanded", *Apple Inc.* v. *VoIP-Pal.com, Inc.*; Case No. 5:20-cv-02460-LHK, *AT&T Corp., AT&T Services, Inc., and AT&T Mobility LLC* v. *VoIP-Pal.com, Inc.*, Case No. 5:20-cv-02995-LHK, Sep. 14, 2021 (31 pages).
"Jury Trial Demanded, Declaration of Dr. Vijay Madisetti", *VoIP-Pal.com, Inc.* v. *Meta Platforms, Inc. and Whatsapp LLC*, Mar. 10, 2022 (17 pages).

(56) References Cited

OTHER PUBLICATIONS

"Plaintiff's Responsive Claim Construction Brief", *VoIP-Pal.com, Inc. v. Meta Platforms, Inc. and Whatsapp LLC*, Civil Action No. 6:20-cv-267-ADA, *VoIP-Pal.com, Inc. v. Google LLC*, Civil Action No. 6:20-cv-269-ADA, *VoIP-Pal.com, Inc. v. Amazon.Com, Inc., Amazon.Com Services LLC, and Amazon Web Services, Inc.*, Civil Action No. 6:20-cv-272-ADA, Apr. 8, 2022 (24 pages).

"Joint Claim Construction Statement", *VoIP-Pal.com, Inc. v. Meta Platforms, Inc. and Whatsapp LLC*, Civil Action No. 6:20-cv-267-ADA, *VoIP-Pal.com, Inc. v. Google LLC*, Civil Action No. 6:20-cv-269-ADA, *VoIP-Pal.com, Inc. v. Amazon.Com, Inc., Amazon.Com Services LLC, and Amazon Web Services, Inc.*, Civil Action No. 6:20-cv-272-ADA, May 6, 2022 (pp. 7).

"Plaintiff's Surreply Claim Construction Brief", *VoIP-Pal.com, Inc. v. Meta Platforms, Inc. and Whatsapp LLC*, Civil Action No. 6:20-cv-267-ADA, *VoIP-Pal.com, Inc. v. Google LLC*, Civil Action No. 6:20-cv-269-ADA, *VoIP-Pal.com, Inc. v. Amazon.Com, Inc., Amazon.Com Services LLC, and Amazon Web Services, Inc.*, Civil Action No. 6:20-cv-272-ADA, May 6, 2022 (pp. 7).

"Claim Construction Order", *VoIP-Pal.com, Inc. v. Amazon.Com, Inc., et al.*, Case No. 6:21-CV-00668-ADA, *VoIP-Pal.com, Inc., v. Verizon Communications, Inc., et al.*, Case No. 6:21-CV-00672-ADA, *VoIP-Pal.com, Inc., v. T-Mobile USA, Inc.*, Case No. 6:21-CV-00674-ADA, Jun. 3, 2022 (pp. 3).

International Telecommunication Unit Telecommunication Standardization Sector ("ITU-T"), "H.323: Packet-based multimedia communications systems," Nov. 2000, Series H. (258 pages).

US Notice of Intent to Issue a Reexam Certificate dated Nov. 9, 2023, 9 pages for U.S. Pat. No. 10,218,606.

First Amended Complaint, *VoIP-Pal.com, Inc. v. AT&T Corp et al.*, United States District Court For The District of Columbia, Case No. 1:21-cv-03051-RDM, Dec. 17, 2024, 258 pages.

First Amended Complaint, Richard Inza, Michael Inza, *VoIP-Pal.com, Inc. v. AT&T Corp et al.*, United States District Court For The District of Columbia, Case No. 1:24-cv-03054-RDM, Jan. 27, 2025, 262 pages.

Plaintiff's Motion for Leave to Amend Plaintiff's First Amended Complaint, *VoIP-Pal.com, Inc. v. AT&T Corp et al.*, United States District Court For The District of Columbia, Case No. 1:21-cv-03051-RDM, Apr. 22, 2025, 6 pages.

Exhibit 4, Proposed Second Amended Complaint, *VoIP-Pal.com, Inc. v. AT&T Corp et al.*, United States District Court For The District of Columbia, Case No. 1:21-cv-03051-RDM, Apr. 22, 2025, 202 pages.

Appendix 1 (Background of Antitrust and Telecommunications Breaches), Proposed Second AmendedComplaint, *VoIP-Pal.com, Inc. v. AT&T Corp et al.*, United States District Court For The District of Columbia, Case No. 1:21-cv-03051-RDM, Apr. 22, 2025, 17 pages.

Appendix 2 (VoIP-Pal Technology, History and Patents), Proposed Second Amended Complaint, *VoIP-Pal.com, Inc. v. AT&T Corp et al.*, United States District Court For The District of Columbia, Case No. 1:21-cv-03051-RDM, Apr. 22, 2025, 34 pages.

Appendix 3 (Evidence Filed In Inter Partes Reviews (IPRs)); Proposed Second Amended Complaint, *VoIP-Pal.com, Inc. v. AT&T Corp et al.*, United States District Court For The District of Columbia, Case No. 1:21-cv-03051-RDM, Apr. 22, 2025, 343 pages.

Exhibit 4, Proposed Second Amended Complaint, Richard Inza, Michael Inza, *VoIP-Pal.com, Inc. v. AT&T Corp et al.*, United States District Court For The District of Columbia, Case No. 1:24-cv-03054-RDM, Apr. 22, 2025, 221 pages.

\* cited by examiner

SIP Invite Message

60 — Caller 2001 1050 8667
62 — Callee 2001 1050 2222
64 — Digest Parameters XXXXXX
65 — Call ID FF10@ 192.168.0.20
67 — IP Address 192.168.0.20
69 — Caller UDP Port 1

Dialing Profile for a User — 253

| | | |
|---|---|---|
| 258 | Username | Assigned on Subscription |
| 260 | Domain | Domain Associated with User |
| 262 | NDD | 1 |
| 264 | IDD | 011 |
| 266 | Country Code | 1 |
| 267 | Local Area Codes | 604;778 |
| 268 | Caller Minimum Local Length | 10 |
| 270 | Caller Maximum Local Length | 10 |
| 273 | Reseller | Retailer |
| 275 | Maximum # of concurrent calls | Assigned on Subscription |
| 277 | Current # of concurrent calls | Assigned on Subscription |

FIG. 9

Dialing Profile for Caller (Vancouver Subscriber) — 276

| | | |
|---|---|---|
| 258 | Username | 2001 1050 8667 (61 / 63 70 74, 284) |
| 260 | Domain | sp.yvr.digifonica.com ← 282 (286, 288, 290) |
| 262 | NDD | 1 |
| 264 | IDD | 011 |
| 266 | Country Code | 1 |
| 267 | Local Area Codes | 604;778 (Vancouver) |
| 268 | Caller Minimum Local Length | 10 |
| 270 | Caller Maximum Local Length | 10 |
| 273 | Reseller | Klondike |
| 275 | Maximum # of concurrent calls | 5 |
| 277 | Current # of concurrent calls | 0 |

FIG. 10

Callee Profile for Calgary Subscriber

|  |  |
|---:|:---|
| Username | 2001 1050 2222 |
| Domain | sp.yvr.digifonica.com |
| NDD | 1 |
| IDD | 011 |
| Country Code | 1 |
| Local Area Codes | 403 (Calgary) |
| Caller Minimum Local Length | 7 |
| Caller Maximum Local Length | 10 |
| Reseller | Deerfoot |
| Maximum # of concurrent calls | 5 |
| Current # of concurrent calls | 0 |

FIG. 11

Callee Profile for London Subscriber

|  |  |
|---:|:---|
| Username | 4401 1062 4444 |
| Domain | sp.lhr.digifonica.com |
| NDD | 0 |
| IDD | 00 |
| Country Code | 44 |
| Local Area Codes | 20 (London) |
| Caller Minimum Local Length | 10 |
| Caller Maximum Local Length | 11 |
| Reseller | Marble Arch |
| Maximum # of concurrent calls | 5 |
| Current # of concurrent calls | 0 |

FIG. 12

```
                                                          ┌─ 278
DID Bank Table Record Format
    281 ── Username     System subscriber
    272 ── User Domain  Host name of supernode
    274 ── DID          E164#
```

FIG. 13

```
                                         61        ┌─ 300
                                          \
DID Bank Table Record for Calgary Subscriber
    281 ── Username     2001 1050 2222
    272 ── User Domain  Sp.yvr.digifonica.com
    274 ── DID          1 604 867 5309
                        │  │   │   │
                       283 285 287 289
```

FIG. 14

Routing Message Format — 352

- 354 — Supplier Prefix (optional)   Code identifying supplier traffic
- 356 — Delimiter (optional)   Symbol separating fields
- 358 — Callee   PSTN compatible number or Digifonica number
- 360 — Route   Domain name or IP address
- 362 — Time to Live (TTL)   In seconds
- 364 — Other   TBD

FIG. 15

Example of Routing Message – Different Node — 366

440110624444@sp.lhr.digifonica.com;ttl=9999

Prefix to Supernode Table Record Format — 370

- 372 — Prefix   First n digits of callee identifier
- 374 — Supernode Address   IP address or fully qualified domain name

FIG. 17

Prefix to Supernode Table Record for Calgary Subscriber

Prefix   20
Supernode Address   sp.yvr.digifonica.com

FIG. 18

Master List Record Format

| | | |
|---|---|---|
| 500 — | ml_id | Alphanumeric |
| 502 — | Dialing code | Number Sequence |
| 504 — | Country code | The country code is the national prefix to be used when dialing TO a particular country FROM another country. |
| 506 — | Nat Sign #(Area Code) | Number Sequence |
| 508 — | Min Length | Numeric |
| 510 — | Max Length | Numeric |
| 512 — | NDD | The NDD prefix is the access code used to make a call WITHIN that country from one city to another (when calling another city in the same vicinity, this may not be necessary). |
| 514 — | IDD | The IDD prefix is the international prefix needed to dial a call FROM the country listed TO another country. |
| 516 — | Buffer rate | Safe change rate above the highest rate charged by suppliers |

FIG. 19

Example: Master List Record with Populated Fields

| | |
|---|---|
| ml_id | 1019 |
| Dialing code | 1604 |
| Country code | 1 |
| Nat Sign #(Area Code) | 604 |
| Min Length | 7 |
| Max Length | 7 |
| NDD | 1 |
| IDD | 011 |
| Buffer rate | $0.009/min |

FIG. 20

Suppliers List Record Format

| | | |
|---|---|---|
| 540 ~ | Sup_id | Name code |
| 542 ~ | ML_id | Numeric code |
| 544 ~ | Prefix (optional) | String identifying supplier's traffic # |
| 546 ~ | Specific Route | IP address |
| 548 ~ | NDD/IDD rewrite | |
| 550 ~ | Rate | Cost per second to Digifonica to use this route |
| 551 ~ | Timeout | Maximum time to wait for a response when requesting this gateway |

FIG. 21

Telus Supplier Record

| | |
|---|---|
| Sup_id | 2010 (Telus) |
| ML_id | 1019 |
| Prefix (optional) | 4973# |
| Specific Route | 72.64.39.58 |
| NDD/IDD rewrite | 011 |
| Rate | $0.02/min |
| Timeout | 20 |

FIG. 22

Shaw Supplier Record

| | |
|---|---|
| Sup_id | 2011 (Shaw) |
| ML_id | 1019 |
| Prefix (optional) | 4974# |
| Specific Route | 73.65.40.59 |
| NDD/IDD rewrite | 011 |
| Rate | $0.025/min |
| Timeout | 30 |

FIG. 23

Sprint Supplier Record

| | |
|---|---|
| Sup_id | 2012 (Sprint) |
| ML_id | 1019 |
| Prefix (optional) | 4975# |
| Specific Route | 74.66.41.60 |
| NDD/IDD rewrite | 011 |
| Rate | $0.03/min |
| Timeout | 40 |

FIG. 24

Routing Message Buffer for Gateway Call

4973#0116048675309@72.64.39.58;ttl=3600;to=20 —— 570
4974#0116048675309@73.65.40.59;ttl=3600;to=30 —— 572
4975#0116048675309@74.66.41.60;ttl=3600;to=40 —— 574

FIG. 25

Call Block Table Record Format

| | | |
|---|---|---|
| 604 — | Username | Digifonica # |
| 606 — | Block Pattern | PSTN compatible or Digifonica # |

FIG. 26

Call Block Table Record for Calgary Callee

| | | |
|---|---|---|
| 604 — | Username of Callee | 2001 1050 2222 |
| 606 — | Block Pattern | 2001 1050 8664 |

FIG. 27

Call Forwarding Table Record Format for Callee

| | | |
|---|---|---|
| 614 — | Username of Callee | Digifonica # |
| 616 — | Destination Number | Digifonica # |
| 618 — | Sequence Number | Integer indicating order to try this |

FIG. 28

Call Forwarding Table Record for Calgary Callee

| | | |
|---|---|---|
| 614 — | Username of Callee | 2001 1050 2222 |
| 616 — | Destination Number | 2001 1055 2223 |
| 618 — | Sequence Number | 1 |

FIG. 29

Voicemail Table Record Format

| | | |
|---|---|---|
| 624 — | Username of Callee | Digifonica # |
| 626 — | Vm Server | domain name |
| 628 — | Seconds to Voicemail | time to wait before engaging voicemail |
| 630 — | Enabled | yes/no |

FIG. 30

Voicemail Table Record for Calgary Callee

| | |
|---|---|
| Username of Callee | 2001 1050 2222 |
| Vm Server | vm.yvr.digifonica.com |
| Seconds to Voicemail | 20 |
| Enabled | 1 |

FIG. 31

Routing Message Buffer – Same Node

650 — 200110502222@sp.yvr.digifonica.com;ttl=3600
652 — 200110552223@sp.yvr.digifonica.com;ttl=3600
654 — vm.yvr.digifonica.com;20;ttl=60
656 — sp.yvr.digifonica.com

FIG. 32

```
Subscriber Bundle Table Record                              /706
    708 —— Username    Subscriber username
    710 —— Services    Codes identifying service features
                       (e.g. Free local calling; call blocking, voicemail)
```

FIG. 34

```
Subscriber Bundle Record for Vancouver Caller
    708 —— Username    2001 1050 8667
    710 —— Services    10; 14; 16
```

FIG. 35

```
Bundle Override Table Record                                /714
    716 —— ML_Id          Master list ID code
    718 —— Override type  Fixed; percent; cents
    720 —— Override value real number representing value of override type
    722 —— Inc1           first level of charging (minimum # of seconds) charge
    724 —— Inc2           second level of charging
```

FIG. 36

```
Bundle Override Record for Located ML_ID                    /726
    716 —— ML_Id          1019
    718 —— Override type  percent
    720 —— Override value 10.0
    722 —— Inc1           30 seconds
    724 —— Inc2           6 seconds
```

FIG. 37

Subscriber Account Table Record /736

738 — Username    Subscriber username
   740 — Funds balance   real number representing $ value of credit
742 — Free time balance   integer representing # of free seconds

FIG. 38

Subscriber Account Record for Vancouver Caller /744

738 — Username    2001 1050 8667
   740 — Funds balance   $10.00
742 — Free time balance   100

FIG. 39

System Operator Special Rates Table Record /784

| | | |
|---|---|---|
| 786 — | Reseller | retailer id |
| 788 — | ML_Id | master list id |
| 790 — | Markup Table | fixed; percent; cents |
| 792 — | Markup Value | real number representing value of markup type |
| 794 — | Inc1 | first level of charging (minimum # of seconds) charge |
| 796 — | Inc2 | second level of charging |

FIG. 42

System Operator Special Rates Table Record for Klondike /798

| | | |
|---|---|---|
| 786 — | Reseller | Klondike |
| 788 — | ML_Id | 1019 |
| 790 — | Markup Table | cents |
| 792 — | Markup Value | $0.001 |
| 794 — | Inc1 | 30 |
| 796 — | Inc2 | 6 |

FIG. 43

System Operator Markup Table Record  /804
- 806 — Reseller    reseller id code
- 808 — Markup Table    fixed; percent; cents
- 810 — Markup Value    real number representing value of markup type
  - 812 — Inc1    first level of charging (minimum # of seconds) charge
  - 814 — Inc2    second level of charging

FIG. 44

System Operator Markup Table Record for the Reseller Klondike
- 806 — Reseller    Klondike
- 808 — Markup Table    cents
- 810 — Markup Value    $0.01
  - 812 — Inc1    30
  - 814 — Inc2    6

FIG. 45

System Operator Markup Table Record
- 806 — Reseller    all
- 808 — Markup Table    percent
- 810 — Markup Value    1.0
  - 812 — Inc1    30
  - 814 — Inc2    6

FIG. 46

```
Reseller Special Destinations Table Record                    ╱‾832
        834 ──    Reseller    reseller id code
        836 ──     ML_id      Master List ID code
    838 ── Markup Table       fixed; percent; cents
    840 ── Markup Value       real number representing value of markup type
        842 ──      Inc1      first level of charging (minimum # of seconds) charge
        844 ──      Inc2      second level of charging
```

FIG. 47

```
                                                              ╱‾846
Reseller Special Destinations Table Record for the Reseller Klondike
        834 ──    Reseller    Klondike
        836 ──     ML_id      1019
    838 ── Markup Table       percent
    840 ── Markup Value       5%
        842 ──      Inc1      30
        844 ──      Inc2      6
```

FIG. 48

```
                                                              ╱‾848
Reseller Global Markup Table Record
        850 ──    Reseller    reseller id code
    852 ── Markup Table       fixed; percent; cents
    854 ── Markup Value       real number representing value of markup type
        856 ──      Inc1      first level of charging (minimum # of seconds) charge
        858 ──      Inc2      second level of charging
```

FIG. 49

```
                                                              ╱‾860
Reseller Global Markup Table Record for the Reseller Klondike
        850 ──    Reseller    Klondike
    852 ── Markup Table       percent
    854 ── Markup Value       10%
        856 ──      Inc1      30
        858 ──      Inc2      6
```

FIG. 50

SIP Bye Message /‾900

| | | |
|---|---|---|
| 902~ | Caller | Username |
| 904~ | Callee | PSTN compatible # or Username |
| 906~ | Call ID | unique call identifier (hexadecimal string@IP)) |

FIG. 51

SIP Bye Message /‾908

| | | |
|---|---|---|
| 902~ | Caller | 2001 1050 8667 |
| 904~ | Callee | 2001 1050 2222 |
| 906~ | Call ID | FA10@192.168.0.20 |

FIG. 52

RC Call Stop Message — 1000

| | | |
|---|---|---|
| 1002 | Caller | Username |
| 1004 | Callee | PSTN compatible # or Username |
| 1006 | Call ID | unique call identifier (hexadecimal string@IP) |
| 1008 | Acct Start Time | start time of call |
| 1010 | Acct Stop Time | time the call ended |
| 1012 | Acct Session Time | start time-stop time (in seconds) |
| 1014 | Route | IP address for the communications link that was established |

FIG. 54

RC Call Stop Message for Calgary Callee — 1020

| | | |
|---|---|---|
| 1002 | Caller | 2001 1050 8667 |
| 1004 | Callee | 2001 1050 2222 |
| 1006 | Call ID | FA10@192.168.0.20 |
| 1008 | Acct Start Time | 2006-12-30 12:12:12 |
| 1010 | Acct Stop Time | 2006-12-30 12:12:14 |
| 1012 | Acct Session Time | 2 |
| 1014 | Route | 72.64.39.58 |

FIG. 55

Reseller Accounts Table Record ⟵ 982

984 ⟵ Reseller ID    reseller id code
  986 ⟵ Reseller balance    accumulated balance of charges

FIG. 57

Reseller Accounts Table Record for Klondike ⟵ 988

984 ⟵ Reseller ID    Klondike
  986 ⟵ Reseller balance    $100.02

FIG. 58

System Operator Accounts Table Record ⟵ 994

996 ⟵ System Operator balance    accumulated balance of charges

FIG. 59

System Operator Accounts Record for this System Operator

996 ⟵ System Operator balance    $1000.02

FIG. 60

DETERMINING A TIME TO PERMIT A COMMUNICATIONS SESSION TO BE CONDUCTED

CROSS REFERENCE TO RELATED APPLICATIONS

This application is a continuation of U.S. patent application Ser. No. 14/853,705, filed Sep. 14, 2015, which is a continuation of U.S. patent application Ser. No. 14/029,671, filed Sep. 17, 2013, which is a continuation of U.S. patent application Ser. No. 12/513,147, filed Mar. 1, 2010, which is a national phase entry of International Application No. PCT/CA2007/001956, filed Nov. 1, 2007, which claims the benefit of U.S. Provisional Patent Application No. 60/856,212, filed on Nov. 2, 2006, all of which are incorporated herein by reference.

BACKGROUND OF THE INVENTION

Field of Invention

This invention relates to voice over IP communications and methods and apparatus for routing and billing.

Description of Related Art

Internet protocol (IP) telephones are typically personal computer (PC) based telephones connected within an IP network, such as the public Internet or a private network of a large organization. These IP telephones have installed "voice-over-IP" (VoIP) software enabling them to make and receive voice calls and send and receive information in data and video formats.

IP telephony switches installed within the IP network enable voice calls to be made within or between IP networks, and between an IP network and a switched circuit network (SCN), such as the public switched telephone network (PSTN). If the IP switch supports the Signaling System 7 (SS7) protocol, the IP telephone can also access PSTN databases.

The PSTN network typically includes complex network nodes that contain all information about a local calling service area including user authentication and call routing. The PSTN network typically aggregates all information and traffic into a single location or node, processes it locally and then passes it on to other network nodes, as necessary, by maintaining route tables at the node. PSTN nodes are redundant by design and thus provide reliable service, but if a node should fail due to an earthquake or other natural disaster, significant, if not complete service outages can occur, with no other nodes being able to take up the load.

Existing VoIP systems do not allow for high availability and resiliency in delivering Voice Over IP based Session Initiation Protocol (SIP) Protocol service over a geographically dispersed area such as a city, region or continent. Most resiliency originates from the provision of IP based telephone services to one location or a small number of locations such as a single office or network of branch offices.

SUMMARY OF THE INVENTION

In accordance with one aspect of the invention, there is provided a process for operating a call routing controller to facilitate communication between callers and callees in a system comprising a plurality of nodes with which callers and callees are associated. The process involves, in response to initiation of a call by a calling subscriber, receiving a caller identifier and a callee identifier. The process also involves using call classification criteria associated with the caller identifier to classify the call as a public network call or a private network call. The process further involves producing a routing message identifying an address, on the private network, associated with the callee when the call is classified as a private network call. The process also involves producing a routing message identifying a gateway to the public network when the call is classified as a public network call.

The process may involve receiving a request to establish a call, from a call controller in communication with a caller identified by the callee identifier.

Using the call classification criteria may involve searching a database to locate a record identifying calling attributes associated with a caller identified by the caller identifier.

Locating a record may involve locating a caller dialing profile comprising a username associated with the caller, a domain associated with the caller, and at least one calling attribute.

Using the call classification criteria may involve comparing calling attributes associated with the caller dialing profile with aspects of the callee identifier.

Comparing may involve determining whether the callee identifier includes a portion that matches an IDD associated with the caller dialing profile.

Comparing may involve determining whether the callee identifier includes a portion that matches an NDD associated with the caller dialing profile.

Comparing may involve determining whether the callee identifier includes a portion that matches an area code associated with the caller dialing profile.

Comparing may involve determining whether the callee identifier has a length within a range specified in the caller dialing profile.

The process may involve formatting the callee identifier into a pre-defined digit format to produce a re-formatted callee identifier.

Formatting may involve removing an international dialing digit from the callee identifier, when the callee identifier begins with a digit matching an international dialing digit specified by the caller dialing profile associated with the caller.

Formatting may involve removing a national dialing digit from the callee identifier and prepending a caller country code to the callee identifier when the callee identifier begins with a national dialing digit.

Formatting may involve prepending a caller country code to the callee identifier when the callee identifier begins with digits identifying an area code specified by the caller dialing profile.

Formatting may involve prepending a caller country code and an area code to the callee identifier when the callee identifier has a length that matches a caller dialing number format specified by the caller dialing profile and only one area code is specified as being associated with the caller in the caller dialing profile.

The process may involve classifying the call as a private network call when the re-formatted callee identifier identifies a subscriber to the private network. The process may involve determining whether the callee identifier complies with a pre-defined username format and if so, classifying the call as a private network call.

The process may involve causing a database of records to be searched to locate a direct in dial (DID) bank table record associating a public telephone number with the reformatted callee identifier and if the DID bank table record is found, classifying the call as a private network call and if a DID bank table record is not found, classifying the call as a public network call.

Producing the routing message identifying a node on the private network may involve setting a callee identifier in response to a username associated with the DID bank table record.

Producing the routing message may involve determining whether a node associated with the reformatted callee identifier is the same as a node associated the caller identifier.

Determining whether a node associated with the reformatted callee identifier is the same as a node associated the caller identifier may involve determining whether a prefix of the re-formatted callee identifier matches a corresponding prefix of a username associated with the caller dialing profile.

When the node associated with the caller is not the same as the node associated with the callee, the process involves producing a routing message including the caller identifier, the reformatted callee identifier and an identification of a private network node associated with the callee and communicating the routing message to a call controller.

When the node associated with the caller is the same as the node associated with the callee, the process involves determining whether to perform at least one of the following: forward the call to another party, block the call and direct the caller to a voicemail server associated with the callee.

Producing the routing message may involve producing a routing message having an identification of at least one of the callee identifier, an identification of a party to whom the call should be forwarded and an identification of a voicemail server associated with the callee.

The process may involve communicating the routing message to a call controller.

Producing a routing message identifying a gateway to the public network may involve searching a database of route records associating route identifiers with dialing codes to find a route record having a dialing code having a number pattern matching at least a portion of the reformatted callee identifier.

The process may involve searching a database of supplier records associating supplier identifiers with the route identifiers to locate at least one supplier record associated with the route identifier associated with the route record having a dialing code having a number pattern matching at least a portion of the reformatted callee identifier.

The process may involve loading a routing message buffer with the reformatted callee identifier and an identification of specific routes associated respective ones of the supplier records associated with the route record and loading the routing message buffer with a time value and a timeout value.

The process may involve communicating a routing message involving the contents of the routing message buffer to a call controller.

The process may involve causing the dialing profile to include a maximum concurrent call value and a concurrent call count value and causing the concurrent call count value to be incremented when the user associated with the dialing profile initiates a call and causing the concurrent call count value to be decremented when a call with the user associated with the dialing profile is ended.

In accordance with another aspect of the invention, there is provided a call routing apparatus for facilitating communications between callers and callees in a system comprising a plurality of nodes with which callers and callees are associated. The apparatus includes receiving provisions for receiving a caller identifier and a callee identifier, in response to initiation of a call by a calling subscriber. The apparatus also includes classifying provisions for classifying the call as a private network cal or a public network call according to call classification criteria associated with the caller identifier. The apparatus further includes provisions for producing a routing message identifying an address, on the private network, associated with the callee when the call is classified as a private network call. The apparatus also includes provisions for producing a routing message identifying a gateway to the public network when the call is classified as a public network call.

The receiving provisions may be operably configured to receive a request to establish a call, from a call controller in communication with a caller identified by the callee identifier.

The apparatus may further include searching provisions for searching a database including records associating calling attributes with subscribers to the private network to locate a record identifying calling attributes associated with a caller identified by the caller identifier.

The records may include dialing profiles each including a username associated with the subscriber, an identification of a domain associated with the subscriber, and an identification of at least one calling attribute associated with the sub scriber.

The call classification provisions may be operably configured to compare calling attributes associated with the caller dialing profile with aspects of the callee identifier.

The calling attributes may include an international dialing digit and call classification provisions may be operably configured to determine whether the callee identifier includes a portion that matches an IDD associated with the caller dialing profile.

The calling attributes may include an national dialing digit and the call classification provisions may be operably configured to determine whether the callee identifier includes a portion that matches an NDD associated with the caller dialing profile.

The calling attributes may include an area code and the call classification provisions may be operably configured to determine whether the callee identifier includes a portion that matches an area code associated with the caller dialing profile.

The calling attribute may include a number length range and the call classification provisions may be operably configured to determine whether the callee identifier has a length within a number length range specified in the caller dialing profile.

The apparatus may further include formatting provisions for formatting the callee identifier into a pre-defined digit format to produce a re-formatted callee identifier.

The formatting provisions may be operably configured to remove an international dialing digit from the callee identifier, when the callee identifier begins with a digit matching an international dialing digit specified by the caller dialing profile associated with the caller.

The formatting provisions may be operably configured to remove a national dialing digit from the callee identifier and prepend a caller country code to the callee identifier when the callee identifier begins with a national dialing digit.

The formatting provisions may be operably configured to prepend a caller country code to the callee identifier when the callee identifier begins with digits identifying an area code specified by the caller dialing profile.

The formatting provisions may be operably configured to prepend a caller country code and area code to the callee identifier when the callee identifier has a length that matches a caller dialing number format specified by the caller dialing profile and only one area code is specified as being associated with the caller in the caller dialing profile.

The classifying provisions may be operably configured to classify the call as a private network call when the reformatted callee identifier identifies a subscriber to the private network.

The classifying provisions may be operably configured to classify the call as a private network call when the callee identifier complies with a pre-defined username format.

The apparatus may further include searching provisions for searching a database of records to locate a direct in dial (DID) bank table record associating a public telephone number with the reformatted callee identifier and the classifying provisions may be operably configured to classify the call as a private network call when the DID bank table record is found and to classify the call as a public network call when a DID bank table record is not found.

The private network routing message producing provisions may be operably configured to produce a routing message having a callee identifier set according to a username associated with the DID bank table record.

The private network routing message producing provisions may be operably configured to determine whether a node associated with the reformatted callee identifier is the same as a node associated the caller identifier.

The private network routing provisions may include provisions for determining whether a prefix of the re-formatted callee identifier matches a corresponding prefix of a username associated with the caller dialing profile.

The private network routing message producing provisions may be operably configured to produce a routing message including the caller identifier, the reformatted callee identifier and an identification of a private network node associated with the callee and to communicate the routing message to a call controller.

The private network routing message producing provisions may be operably configured to perform at least one of the following forward the call to another party, block the call and direct the caller to a voicemail server associated with the callee, when the node associated with the caller is the same as the node associated with the callee.

The provisions for producing the private network routing message may be operably configured to produce a routing message having an identification of at least one of the callee identifier, an identification of a party to whom the call should be forwarded and an identification of a voicemail server associated with the callee.

The apparatus further includes provisions for communicating the routing message to a call controller.

The provisions for producing a public network routing message identifying a gateway to the public network may include provisions for searching a database of route records associating route identifiers with dialing codes to find a route record having a dialing code having a number pattern matching at least a portion of the reformatted callee identifier.

The apparatus further includes provisions for searching a database of supplier records associating supplier identifiers with the route identifiers to locate at least one supplier record associated with the route identifier associated with the route record having a dialing code having a number pattern matching at least a portion of the reformatted callee identifier.

The apparatus further includes a routing message buffer and provisions for loading the routing message buffer with the reformatted callee identifier and an identification of specific routes associated respective ones of the supplier records associated with the route record and loading the routing message buffer with a time value and a timeout value.

The apparatus further includes provisions for communicating a routing message including the contents of the routing message buffer to a call controller.

The apparatus further includes means for causing said dialing profile to include a maximum concurrent call value and a concurrent call count value and for causing said concurrent call count value to be incremented when the user associated with said dialing profile initiates a call and for causing said concurrent call count value to be decremented when a call with said user associated with said dialing profile is ended.

In accordance with another aspect of the invention, there is provided a data structure for access by an apparatus for producing a routing message for use by a call routing controller in a communications system. The data structure includes dialing profile records comprising fields for associating with respective subscribers to the system, a subscriber user name, direct-in-dial records comprising fields for associating with respective subscriber usernames, a user domain and a direct-in-dial number, prefix to node records comprising fields for associating with at least a portion of the respective subscriber usernames, a node address of a node in the system, whereby a subscriber name can be used to find a user domain, at least a portion of the a subscriber name can be used to find a node with which the subscriber identified by the subscriber name is associated, and a user domain and subscriber name can be located in response to a direct-in-dial number.

In accordance with another aspect of the invention, there is provided a data structure for access by an apparatus for producing a routing message for use by a call routing controller in a communications system. The data structure includes master list records comprising fields for associating a dialing code with respective master list identifiers and supplier list records linked to master list records by the master list identifiers, said supplier list records comprising fields for associating with a communications services supplier, a supplier id, a master list id, a route identifier and a billing rate code, whereby communications services suppliers are associated with dialing codes, such that dialing codes can be used to locate suppliers capable of providing a communications link associated with a given dialing code.

In accordance with another aspect of the invention, there is provided a method for determining a time to permit a communication session to be conducted. The method involves calculating a cost per unit time, calculating a first time value as a sum of a free time attributed to a participant in the communication session and the quotient of a funds balance held by the participant to the cost per unit time value and producing a second time value in response to the first time value and a billing pattern associated with the participant, the billing pattern including first and second billing intervals and the second time value being the time to permit a communication session to be conducted.

Calculating the first time value may involve retrieving a record associated with the participant and obtaining from the record at least one of the free time and the funds balance.

Producing the second time value may involve producing a remainder value representing a portion of the second billing interval remaining after dividing the second billing interval into a difference between the first time value and the first billing interval.

Producing the second time value may involve setting a difference between the first time value and the remainder as the second time value.

The method may further involve setting the second time value to zero when the remainder is greater than zero and the first time value is less than the free time associated with the participant.

Calculating the cost per unit time may involve locating a record in a database, the record comprising a markup type indicator, a markup value and a billing pattern and setting a reseller rate equal to the sum of the markup value and the buffer rate.

Locating the record in a database may involve locating at least one of a record associated with a reseller and a route associated with the reseller, a record associated with the reseller and a default reseller markup record.

Calculating the cost per unit time value further may involve locating at least one of an override record specifying a route cost per unit time amount associated with a route associated with the communication session, a reseller record associated with a reseller of the communications session, the reseller record specifying a reseller cost per unit time associated with the reseller for the communication session, a default operator markup record specifying a default cost per unit time.

The method may further involve setting as the cost per unit time the sum of the reseller rate and at least one of the route cost per unit time, the reseller cost per unit time and the default cost per unit time.

The method may further involve receiving a communication session time representing a duration of the communication session and incrementing a reseller balance by the product of the reseller rate and the communication session time.

The method may further involve receiving a communication session time representing a duration of the communication session and incrementing a system operator balance by a product of the buffer rate and the communication session time.

In accordance with another aspect of the invention, there is provided an apparatus for determining a time to permit a communication session to be conducted. The apparatus includes a processor circuit, a computer readable medium coupled to the processor circuit and encoded with instructions for directing the processor circuit to calculate a cost per unit time for the communication session, calculate a first time value as a sum of a free time attributed to a participant in the communication session and the quotient of a funds balance held by the participant to the cost per unit time value and produce a second time value in response to the first time value and a billing pattern associated with the participant, the billing pattern including first and second billing intervals and the second time value being the time to permit a communication session to be conducted.

The instructions may include instructions for directing the processor circuit to retrieve a record associated with the participant and obtain from the record at least one of the free time and the funds balance.

The instructions may include instructions for directing the processor circuit to produce the second time value by producing a remainder value representing a portion of the second billing interval remaining after dividing the second billing interval into a difference between the first time value and the first billing interval.

The instructions may include instructions for directing the processor circuit to produce the second time value comprises setting a difference between the first time value and the remainder as the second time value.

The instructions may include instructions for directing the processor circuit to set the second time value to zero when the remainder is greater than zero and the first time value is less than the free time associated with the participant.

The instructions for directing the processor circuit to calculate the cost per unit time may include instructions for directing the processor circuit to locate a record in a database, the record comprising a markup type indicator, a markup value and a billing pattern and set a reseller rate equal to the sum of the markup value and the buffer rate.

The instructions for directing the processor circuit to locate the record in a database may include instructions for directing the processor circuit to locate at least one of a record associated with a reseller and a route associated with the reseller, a record associated with the reseller, and a default reseller markup record. The instructions for directing the processor circuit to calculate the cost per unit time value may further include instructions for directing the processor circuit to locate at least one of an override record specifying a route cost per unit time amount associated with a route associated with the communication session, a reseller record associated with a reseller of the communications session, the reseller record specifying a reseller cost per unit time associated with the reseller for the communication session, a default operator markup record specifying a default cost per unit time.

The instructions may include instructions for directing the processor circuit to set as the cost per unit time the sum of the reseller rate and at least one of the route cost per unit time, the reseller cost per unit time and the default cost per unit time.

The instructions may include instructions for directing the processor circuit to receive a communication session time representing a duration of the communication session and increment a reseller balance by the product of the reseller rate and the communication session time.

The instructions may include instructions for directing the processor circuit to receive a communication session time representing a duration of the communication session and increment a system operator balance by a product of the buffer rate and the communication session time.

In accordance with another aspect of the invention, there is provided a process for attributing charges for communications services. The process involves determining a first chargeable time in response to a communication session time and a pre-defined billing pattern, determining a user cost value in response to the first chargeable time and a free time value associated with a user of the communications services, changing an account balance associated with the user in response to a user cost per unit time. The process may further involve changing an account balance associated with a reseller of the communications services in response to a reseller cost per unit time and the communication session time and changing an account balance associated with an operator of the communications services in response to an operator cost per unit time and the communication session time.

Determining the first chargeable time may involve locating at least one of an override record specifying a route cost per unit time and billing pattern associated with a route associated with the communication session, a reseller record associated with a reseller of the communications session, the reseller record specifying a reseller cost per unit time and billing pattern associated with the reseller for the communication session and a default record specifying a default cost per unit time and billing pattern and setting as the pre-defined billing pattern the billing pattern of the record located. The billing pattern of the record located may involve a first billing interval and a second billing interval.

Determining the first chargeable time may involve setting the first chargeable time equal to the first billing interval when the communication session time is less than or equal to the first billing interval.

Determining the first chargeable time may involve producing a remainder value representing a portion of the second billing interval remaining after dividing the second billing interval into a difference between communication session time and the first interval when the communication session time is greater than the communication session time and setting the first chargeable time to a difference between the communication session time and the remainder when the remainder is greater than zero and setting the first chargeable time to the communication session time when the remainder is not greater than zero.

The process may further involve determining a second chargeable time in response to the first chargeable time and the free time value associated with the user of the communications services when the first chargeable time is greater than or equal to the free time value associated with the user of the communications services.

Determining the second chargeable time may involve setting the second chargeable time to a difference between the first chargeable time.

The process may further involve resetting the free time value associated with the user to zero when the first chargeable time is greater than or equal to the free time value associated with the user of the communications services.

Changing an account balance associated with the user may involve calculating a user cost value in response to the second chargeable time and the user cost per unit time.

The process may further involve changing a user free cost balance in response to the user cost value.

The process may further involve setting the user cost to zero when the first chargeable time is less than the free time value associated with the user.

The process may further involve changing a user free time balance in response to the first chargeable time.

In accordance with another aspect of the invention, there is provided an apparatus for attributing charges for communications services. The apparatus includes a processor circuit, a computer readable medium in communication with the processor circuit and encoded with instructions for directing the processor circuit to determine a first chargeable time in response to a communication session time and a pre-defined billing pattern, determine a user cost value in response to the first chargeable time and a free time value associated with a user of the communications services, change an account balance associated with the user in response to a user cost per unit time.

The instructions may further include instructions for changing an account balance associated with a reseller of the communications services in response to a reseller cost per unit time and the communication session time and changing an account balance associated with an operator of the communications services in response to an operator cost per unit time and the communication session time.

The instructions for directing the processor circuit to determine the first chargeable time may further include instructions for causing the processor circuit to communicate with a database to locate at least one of an override record specifying a route cost per unit time and billing pattern associated with a route associated with the communication session, a reseller record associated with a reseller of the communications session, the reseller record specifying a reseller cost per unit time and billing pattern associated with the reseller for the communication session and a default record specifying a default cost per unit time and billing pattern and instructions for setting as the pre-defined billing pattern the billing pattern of the record located. The billing pattern of the record located may include a first billing interval and a second billing interval.

The instructions for causing the processor circuit to determine the first chargeable time may include instructions for directing the processor circuit to set the first chargeable time equal to the first billing interval when the communication session time is less than or equal to the first billing interval.

The instructions for causing the processor circuit to determine the first chargeable time may include instructions for producing a remainder value representing a portion of the second billing interval remaining after dividing the second billing interval into a difference between communication session time and the first interval when the communication session time is greater than the communication session time and instructions for causing the processor circuit to set the first chargeable time to a difference between the communication session time and the remainder when the remainder is greater than zero and instructions for causing the processor circuit to set the first chargeable time to the communication session time when the remainder is not greater than zero.

The instructions may further include instructions for causing the processor circuit to determine a second chargeable time in response to the first chargeable time and the free time value associated with the user of the communications services when the first chargeable time is greater than or equal to the free time value associated with the user of the communications services.

The instructions for causing the processor circuit to determine the second chargeable time may include instructions for causing the processor circuit to set the second chargeable time to a difference between the first chargeable time.

The instructions may further include instructions for causing the processor circuit to reset the free time value associated with the user to zero when the first chargeable time is greater than or equal to the free time value associated with the user of the communications services.

The instructions for causing the processor circuit to change an account balance associated with the user may include instructions for causing the processor circuit to calculate a user cost value in response to the second chargeable time and the user cost per unit time.

The instructions may further include instructions for causing the processor circuit to change a user free cost balance in response to the user cost value.

The instructions may further include instructions for causing the processor circuit to set the user cost to zero when the first chargeable time is less than the free time value associated with the user.

The instructions may further include instructions for causing the processor circuit to change a user free time balance in response to the first chargeable time.

In accordance with another aspect of the invention, there is provided a computer readable medium encoded with codes for directing a processor circuit to execute one or more of the methods described above and/or variants thereof.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention,

FIG. 9 is a tabular representation of a dialing profile stored in a database accessible by the RC shown in FIG. 1;

FIG. 10 is a tabular representation of a dialing profile for a caller using the caller telephone shown in FIG. 1;

FIG. 11 is a tabular representation of a callee profile for a callee located in Calgary;

FIG. 12 is a tabular representation of a callee profile for a callee located in London;

FIG. 13 is a tabular representation of a Direct-in-Dial (DID) bank table record stored in the database shown in FIG. 1;

FIG. 14 is a tabular representation of an exemplary DID bank table record for the Calgary callee referenced in FIG. 11;

FIG. 15 is a tabular representation of a routing message transmitted from the RC to the call controller shown in FIG. 1;

FIG. 16 is a schematic representation of a routing message buffer holding a routing message for routing a call to the Calgary callee referenced in FIG. 11;

FIG. 17 is a tabular representation of a prefix to supernode table record stored in the database shown in FIG. 1;

FIG. 18 is a tabular representation of a prefix to supernode table record that would be used for the Calgary callee referenced in FIG. 11;

FIG. 19 is a tabular representation of a master list record stored in a master list table in the database shown in FIG. 1;

FIG. 20 is a tabular representation of a populated master list record;

FIG. 21 is a tabular representation of a suppliers list record stored in the database shown in FIG. 1;

FIG. 22 is a tabular representation of a specific supplier list record for a first supplier;

FIG. 23 is a tabular representation of a specific supplier list record for a second supplier;

FIG. 24 is a tabular representation of a specific supplier list record for a third supplier;

FIG. 25 is a schematic representation of a routing message, held in a routing message buffer, identifying to the controller a plurality of possible suppliers that may carry the call;

FIG. 26 is a tabular representation of a call block table record;

FIG. 27 is a tabular representation of a call block table record for the Calgary callee;

FIG. 28 is a tabular representation of a call forwarding table record;

FIG. 29 is a tabular representation of a call forwarding table record specific for the Calgary callee;

FIG. 30 is a tabular representation of a voicemail table record specifying voicemail parameters to enable the caller to leave a voicemail message for the callee;

FIG. 31 is a tabular representation of a voicemail table record specific to the Calgary callee;

FIG. 32 is a schematic representation of an exemplary routing message, held in a routing message buffer, indicating call forwarding numbers and a voicemail server identifier;

FIG. 34 is a tabular representation of a subscriber bundle table record;

FIG. 35 is a tabular representation of a subscriber bundle record for the Vancouver caller;

FIG. 36 is a tabular representation of a bundle override table record;

FIG. 37 is a tabular representation of bundle override record for a located master list ID;

FIG. 38 is a tabular representation of a subscriber account table record;

FIG. 39 is a tabular representation of a subscriber account record for the Vancouver caller;

FIG. 42 is a tabular representation of a system operator special rates table record;

FIG. 43 is a tabular representation of a system operator special rates table record for a reseller named Klondike;

FIG. 44 is a tabular representation of a system operator mark-up table record;

FIG. 45 is a tabular representation of a system operator mark-up table record for the reseller Klondike;

FIG. 46 is a tabular representation of a default system operator mark-up table record;

FIG. 47 is a tabular representation of a reseller special destinations table record;

FIG. 48 is a tabular representation of a reseller special destinations table record for the reseller Klondike;

FIG. 49 is a tabular representation of a reseller global mark-up table record;

FIG. 50 is a tabular representation of a reseller global mark-up table record for the reseller Klondike;

FIG. 51 is a tabular representation of a SIP bye message transmitted from either of the telephones shown in FIG. 1 to the call controller;

FIG. 52 is a tabular representation of a SIP bye message sent to the controller from the Calgary callee;

FIG. 54 is a tabular representation of an exemplary RC call stop message;

FIG. 55 is a tabular representation of an RC call stop message for the Calgary callee;

FIG. 57 is a tabular representation of a reseller accounts table record;

FIG. 58 is a tabular representation of a reseller accounts table record for the reseller Klondike;

FIG. 59 is a tabular representation of a system operator accounts table record; and FIG. 60 is a tabular representation of a system operator accounts record for the system operator described herein.

DETAILED DESCRIPTION

Figure 1:
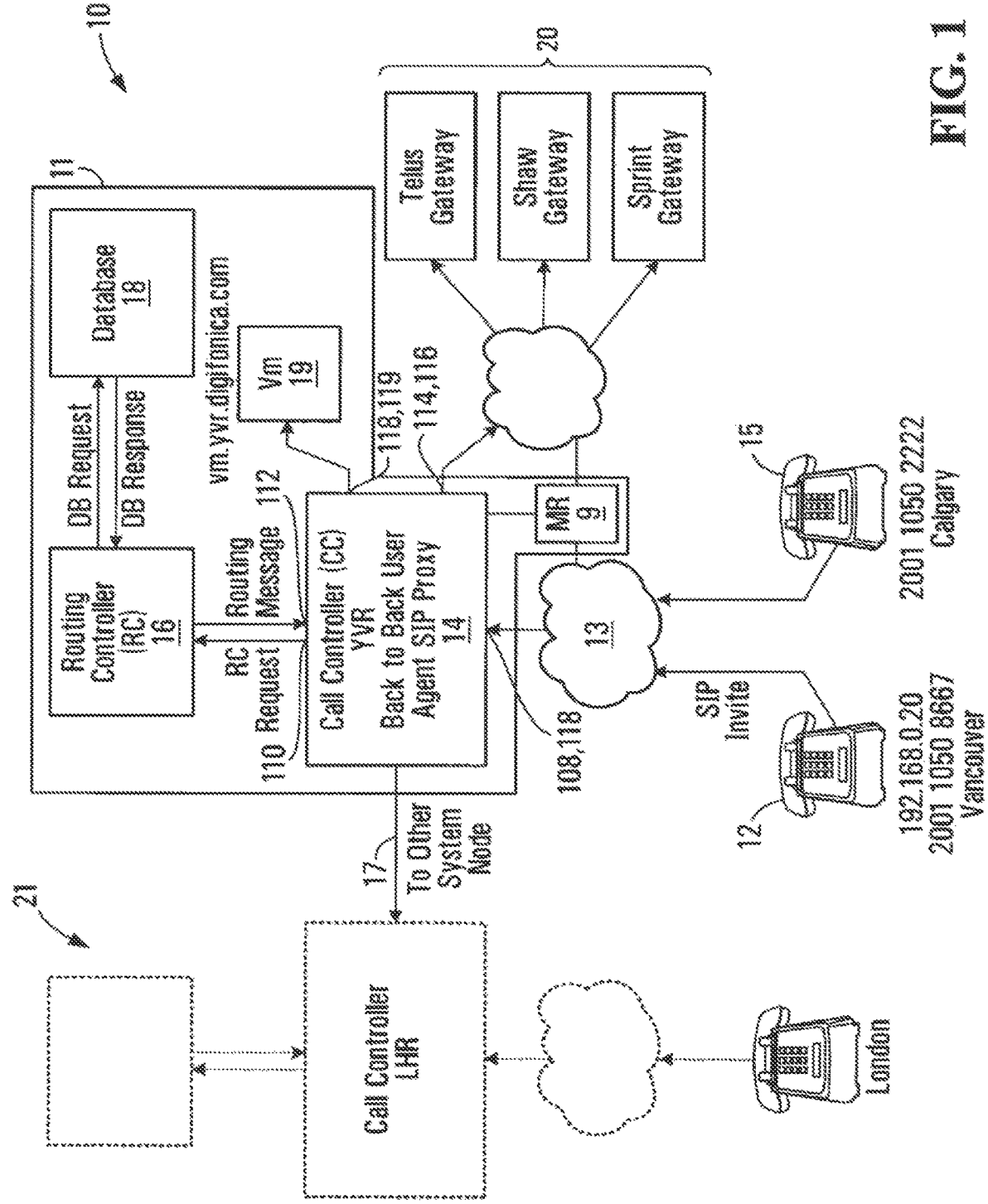
FIG. 1 is a block diagram of a system according to a first embodiment of the invention.

Referring to FIG. 1, a system for making voice over IP telephone/videophone calls is shown generally at 10. The system includes a first super node shown generally at 11 and a second super node shown generally at 21. The first super node 11 is located in geographical area, such as Vancouver, B.C., Canada for example and the second super node 21 is located in London, England, for example. Different super nodes may be located in different geographical regions throughout the world to provide telephone/videophone service to subscribers in respective regions. These super nodes may be in communication with each other by high speed/high data throughput links including optical fiber, satellite and/or cable links, forming a backbone to the system. These super nodes may alternatively or, in addition, be in communication with each other through conventional internet services.

In the embodiment shown, the Vancouver supernode 11 provides telephone/videophone service to western Canadian customers from Vancouver Island to Ontario. Another node (not shown) may be located in Eastern Canada to provide services to subscribers in that area.

Other nodes of the type shown may also be employed within the geographical area serviced by a supernode, to provide for call load sharing, for example within a region of the geographical area serviced by the supernode. However, in general, all nodes are similar and have the properties described below in connection with the Vancouver supernode 11.

In this embodiment, the Vancouver supernode includes a call controller (C) 14, a routing controller (RC) 16, a database 18 and a voicemail server 19 and a media relay 9. Each of these may be implemented as separate modules on a common computer system or by separate computers, for example. The voicemail server 19 need not be included in the node and can be provided by an outside service provider.

Subscribers such as a subscriber in Vancouver and a subscriber in Calgary communicate with the Vancouver supernode using their own internet service providers which route internet traffic from these subscribers over the internet shown generally at 13 in FIG. 1. To these subscribers the Vancouver supernode is accessible at a pre-determined internet protocol (IP) address or a fully qualified domain name that can be accessed in the usual way through a subscriber's internet service provider. The subscriber in Vancouver uses a telephone 12 that is capable of communicating with the Vancouver supernode 11 using Session Initiation Protocol (SIP) messages and the Calgary subscriber uses a similar telephone 15, in Calgary AB.

It should be noted that throughout the description of the embodiments of this invention, the IP/UDP addresses of all elements such as the caller and callee telephones, call controller, media relay, and any others, will be assumed to be valid IP/UDP addresses directly accessible via the Internet or a private IP network, for example, depending on the specific implementation of the system. As such, it will be assumed, for example, that the caller and callee telephones will have IP/UDP addresses directly accessible by the call controllers and the media relays on their respective supernodes, and those addresses will not be obscured by Network Address Translation (NAT) or similar mechanisms. In other words, the IP/UDP information contained in SIP messages (for example the SIP Invite message or the RC Request message which will be described below) will match the IP/UDP addresses of the IP packets carrying these SIP messages.

It will be appreciated that in many situations, the IP addresses assigned to various elements of the system may be in a private IP address space, and thus not directly accessible from other elements. Furthermore, it will also be appreciated that NAT is commonly used to share a "public" IP address between multiple devices, for example between home PCs and IP telephones sharing a single Internet connection. For example, a home PC may be assigned an IP address such as 192.168.0.101 and a Voice over IP telephone may be assigned an IP address of 192.168.0.103. These addresses are located in so called "non-routable" (IP) address space and cannot be accessed directly from the Internet. In order for these devices to communicate with other computers located on the Internet, these IP addresses have to be converted into a "public" IP address, for example 24.10.10.123 assigned by the Internet Service Provider to the subscriber, by a device performing NAT, typically a home router. In addition to translating the IP addresses, NAT typically also translates UDP port numbers, for example an audio path originating at a VoIP telephone and using a UDP port 12378 at its private IP address, may have be translated to a UDP port 23465 associated with the public IP address of the NAT device. In other words, when a packet originating from the above VoIP telephone arrives at an Internet-based supernode, the source IP/UDP address contained in the IP packet header will be 24.10.10.1:23465, whereas the source IP/UDP address information contained in the SIP message inside this IP packet will be 192.168.0.103:12378. The mismatch in the IP/UDP addresses may cause a problem for SIP-based VoW systems because, for example, a supernode will attempt to send messages to a private address of a telephone but the messages will never get there.

Referring to FIG. 1, in an attempt to make a call by the Vancouver telephone/videophone 12 to the Calgary telephone/videophone 15, the Vancouver telephone/videophone sends a SIP invite message to the Vancouver supernode 11 and in response, the call controller 14 sends an RC request message to the RC 16 which makes various enquiries of the database 18 to produce a routing message which is sent back to the call controller 14. The call controller 14 then communicates with the media relay 9 to cause a communications link including an audio path and a videophone (if a video-path call) to be established through the media relay to the same node, a different node or to a communications supplier gateway as shown generally at 20 to carry audio, and where applicable, video traffic to the call recipient or callee.

Generally, the RC 16 executes a process to facilitate communication between callers and callees. The process involves, in response to initiation of a call by a calling subscriber, receiving a callee identifier from the calling subscriber, using call classification criteria associated with the calling subscriber to classify the call as a public network call or a private network call and producing a routing message identifying an address on the private network, associated with the callee when the call is classified as a private network call and producing a routing message identifying a gateway to the public network when the call is classified as a public network call.

Subscriber Telephone

Figure 2:
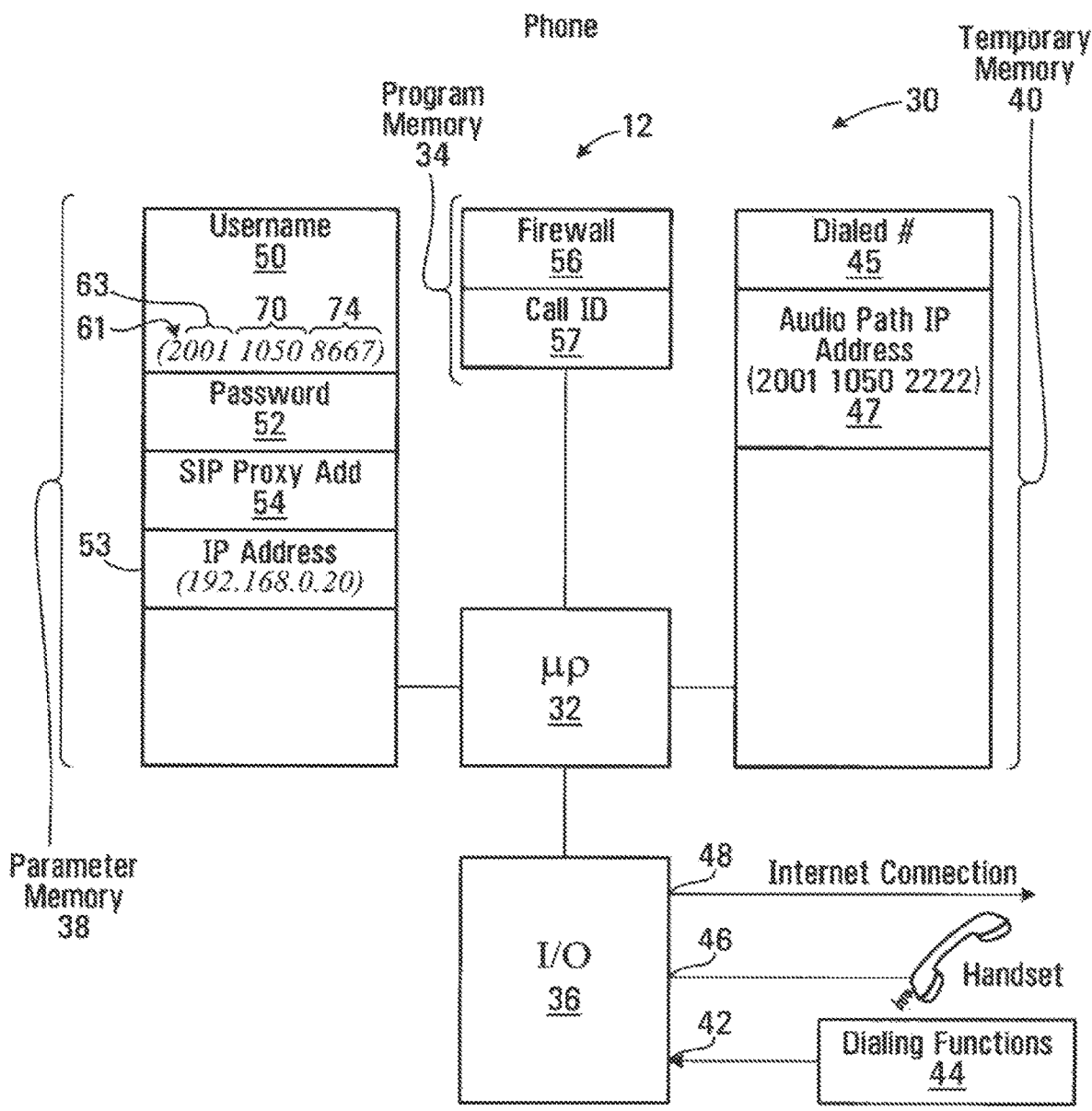
FIG. 2 is a block diagram of a caller telephone according to the first embodiment of the invention.

In greater detail, referring to FIG. 2, in this embodiment, the telephone/videophone 12 includes a processor circuit shown generally at 30 comprising a microprocessor 32, program memory 34, an input/output (I/O) port 36, parameter memory 38 and temporary memory 40. The program memory 34, I/O port 36, parameter memory 38 and temporary memory 40 are all in communication with the microprocessor 32. The I/O port 36 has a dial input 42 for receiving a dialled telephone/videophone number from a keypad, for example, or from a voice recognition unit or from pre-stored telephone/videophone numbers stored in the parameter memory 38, for example. For simplicity, in FIG. 2 a box labelled dialing functions 44 represents any device capable of informing the microprocessor 32 of a callee identifier, e.g., a callee telephone/videophone number.

The processor 32 stores the callee identifier in a dialled number buffer 45. In this case, assume the dialled number is 2001 1050 2222 and that it is a number associated with the Calgary subscriber. The I/O port 36 also has a handset interface 46 for receiving and producing signals from and to a handset that the user may place to his ear. This interface 46 may include a BLUETOOTH™ wireless interface, a wired interface or speaker phone, for example. The handset acts as a termination point for an audio path (not shown) which will be appreciated later. The I/O port 36 also has an internet connection 48 which is preferably a high speed internet connection and is operable to connect the telephone/videophone to an internet service provider. The internet connection 48 also acts as a part of the voice path, as will be appreciated later. It will be appreciated that where the subscriber device is a videophone, a separate video path is established in the same way an audio path is established. For simplicity, the following description refers to a telephone call, but it is to be understood that a videophone call is handled similarly, with the call controller causing the media relay to facilitate both an audio path and a video path instead of only an audio path.

The parameter memory 38 has a username field 50, a password field 52 an IP address field 53 and a SIP proxy address field 54, for example. The user name field 50 is operable to hold a user name, which in this case is 2001 1050 8667. The user name is assigned upon subscription or registration into the system and, in this embodiment, includes a twelve digit number having a continent code 61, a country code 63, a dealer code 70 and a unique number code 74. The continent code 61 is comprised of the first or left-most digit of the user name in this embodiment. The country code 63 is comprised of the next three digits. The dealer code 70 is comprised of the next four digits and the unique number code 74 is comprised of the last four digits. The password field 52 holds a password of up to 512 characters, in this example. The IP address field 53 stores an IP address of the telephone, which for this explanation is 192.168.0.20. The SIP proxy address field 54 holds an IP protocol compatible proxy address which may be provided to the telephone through the internet connection 48 as part of a registration procedure.

The program memory 34 stores blocks of codes for directing the processor 32 to carry out the functions of the telephone, one of which includes a firewall block 56 which provides firewall functions to the telephone, to prevent access by unauthorized persons to the microprocessor 32 and memories 34, 38 and 40 through the internet connection 48. The program memory 34 also stores codes 57 for establishing a call ID. The call ID codes 57 direct the processor 32 to produce a call identifier having a format comprising a hexadecimal string at an IP address, the IP address being the IP address of the telephone. Thus, an exemplary call identifier might be FF10@192.168.0.20.

Figures 3, 4:
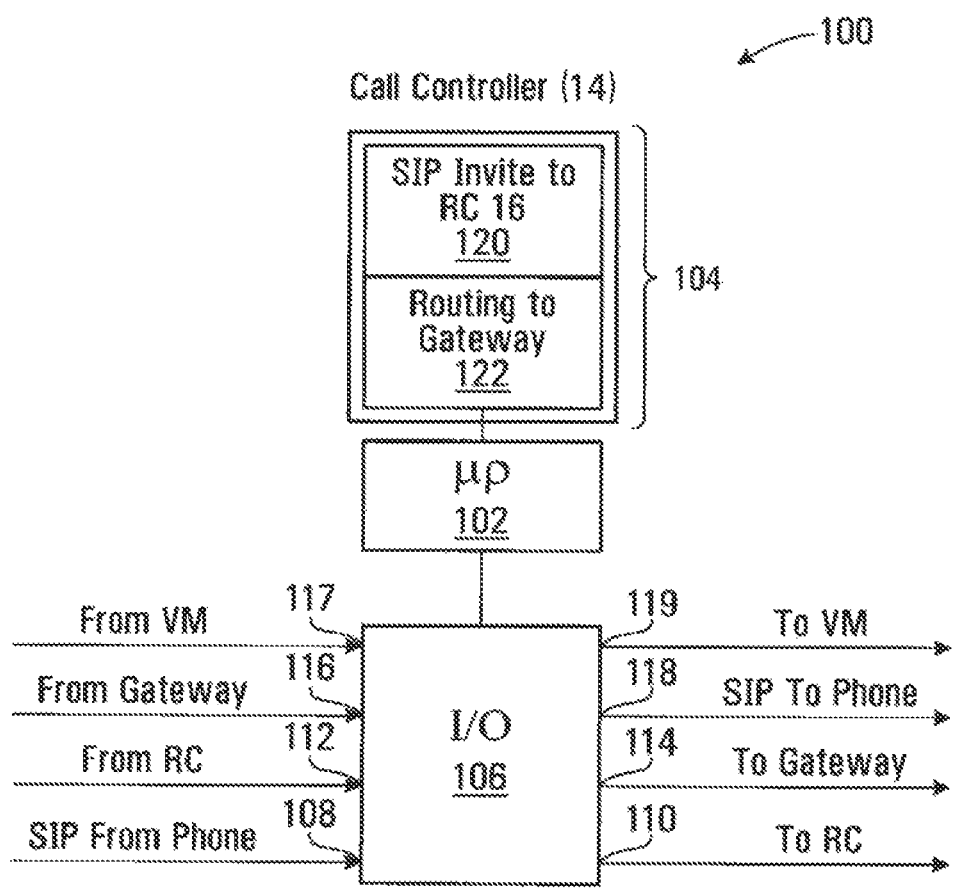
FIG. 3 is a schematic representation of a SIP invite message transmitted between the caller telephone and a controller shown in FIG. 1.
FIG. 4 is a block diagram of a call controller shown in FIG. 1.

Generally, in response to picking up the handset interface 46 and activating a dialing function 44, the microprocessor 32 produces and sends a SIP invite message as shown in FIG. 3, to the routing controller 16 shown in FIG. 1. This SIP invite message is essentially to initiate a call by a calling subscriber.

Referring to FIG. 3, the SIP invite message includes a caller ID field 60, a callee identifier field 62, a digest parameters field 64, a call ID field 65 an IP address field 67 and a caller UDP port field 69. In this embodiment, the caller ID field 60 includes the user name 2001 1050 8667 that is the Vancouver user name stored in the user name field 50 of the parameter memory 38 in the telephone 12 shown in FIG. 2. In addition, referring back to FIG. 3, the callee identifier field 62 includes a callee identifier which in this embodiment is the user name 2001 1050 2222 that is the dialled number of the Calgary subscriber stored in the dialled number buffer 45 shown in FIG. 2. The digest parameters field 64 includes digest parameters and the call ID field 65 includes a code comprising a generated prefix code (FF10) and a suffix which is the Internet Protocol (IP) address of the telephone 12 stored in the IP address field 53 of the telephone. The IP address field 67 holds the IP address assigned to the telephone, in this embodiment 192.168.0.20, and the caller UDP port field 69 includes a UDP port identifier identifying a UDP port at which the audio path will be terminated at the caller's telephone.

Call Controller

Referring to FIG. 4, a call controller circuit of the call controller 14 (FIG. 1) is shown in greater detail at 100. The call controller circuit 100 includes a microprocessor 102, program memory 104 and an I/O port 106. The circuit 100 may include a plurality of microprocessors, a plurality of program memories and a plurality of I/O ports to be able to handle a large volume of calls. However, for simplicity, the call controller circuit 100 will be described as having only one microprocessor 102, program memory 104 and I/O port 106, it being understood that there may be more.

Generally, the I/O port 106 includes an input 108 for receiving messages such as the SIP invite message shown in FIG. 3, from the telephone shown in FIG. 2. The I/O port 106 also has an RC request message output 110 for transmitting an RC request message to the RC 16 of FIG. 1, an RC message input 112 for receiving routing messages from the RC 16, a gateway output 114 for transmitting messages to one of the gateways 20 shown in FIG. 1 to advise the gateway to establish an audio path, for example, and a gateway input 116 for receiving messages from the gateway. The I/O port 106 further includes a SIP output 118 for transmitting messages to the telephone 12 to advise the telephone of the IP addresses of the gateways which will establish the audio path. The I/O port 106 further includes a voicemail server input and output 117, 119 respectively for communicating with the voicemail server 19 shown in FIG. 1.

While certain inputs and outputs have been shown as separate, it will be appreciated that some may be a single IP address and IP port. For example, the messages sent to the RC 16 and received from the RC 16 may be transmitted and received on the same single IP port.

The program memory 104 includes blocks of code for directing the microprocessor 102 to carry out various functions of the call controller 14. For example, these blocks of code include a first block 120 for causing the call controller circuit 100 to execute a SIP invite to RC request process to produce an RC request message in response to a received SIP invite message. In addition, there is a routing message to gateway message block 122 which causes the call controller circuit 100 to produce a gateway query message in response to a received routing message from the RC 16.

Figure 5:
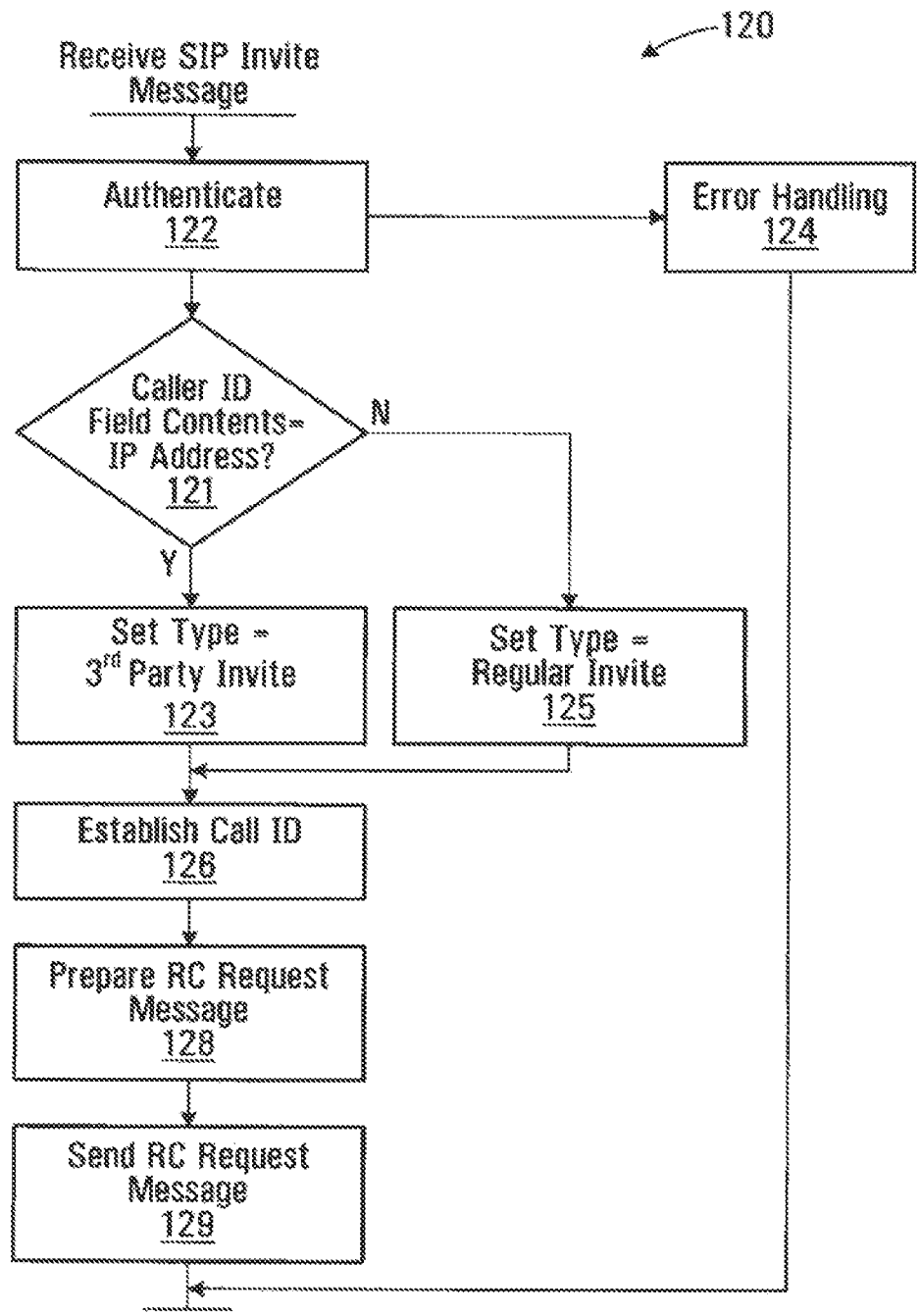
FIG. 5 is a flowchart of a process executed by the call controller shown in FIG. 1.

Referring to FIG. 5, the SIP invite to RC request process is shown in more detail at 120. On receipt of a SIP invite message of the type shown in FIG. 3, block 122 of FIG. 5 directs the call controller circuit 100 of FIG. 4 to authenticate the user. This may be done, for example, by prompting the user for a password, by sending a message back to the telephone 12 which is interpreted at the telephone as a request for a password entry or the password may automatically be sent to the call controller 14 from the telephone, in response to the message. The call controller 14 may then make enquiries of databases to which it has access, to determine whether or not the user's password matches a password stored in the database. Various functions may be used to pass encryption keys or hash codes back and forth to ensure that the transmittal of passwords is secure.

Should the authentication process fail, the call controller circuit 100 is directed to an error handling routine 124 which causes messages to be displayed at the telephone 12 to indicate there was an authentication problem. If the authentication procedure is passed, block 121 directs the call controller circuit 100 to determine whether or not the contents of the caller ID field 60 of the SIP invite message received from the telephone is an IP address. If it is an IP address, then block 123 directs the call controller circuit 100 to set the contents of a type field variable maintained by the microprocessor 102 to a code representing that the call type is a third party invite. If at block 121 the caller ID field contents do not identify an IP address, then block 125 directs the microprocessor to set the contents of the type field to a code indicating that the call is being made by a system subscriber. Then, block 126 directs the call controller circuit to read the call identifier 65 provided in the SIP invite message from the telephone 12, and at block 128 the processor is directed to produce an RC request message that includes that call ID. Block 129 then directs the call controller circuit 100 to send the RC request to the RC 16.

Figures 6, 7:
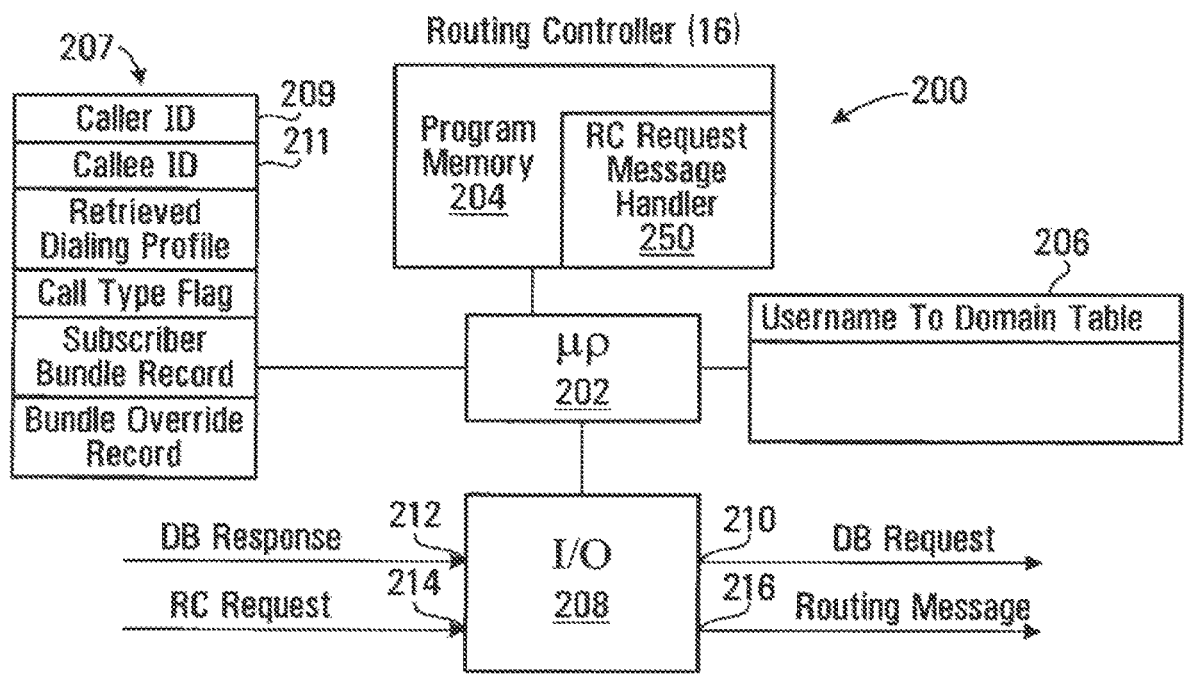
FIG. 6 is a schematic representation of a routing, billing and rating (RC) request message produced by the call controller shown in FIG. 1.
FIG. 7 is a block diagram of a processor circuit of a routing, billing, rating element of the system shown in FIG. 1.

Referring to FIG. 6, an RC request message is shown generally at 150 and includes a caller field 152, a callee field 154, a digest field 156, a call ID field 158 and a type field 160. The caller, callee, digest call ID fields 152, 154, 156 and 158 contain copies of the caller, callee, digest parameters and call ID fields 60, 62, 64 and 65 of the SIP invite message shown in FIG. 3. The type field 160 contains the type code established at blocks 123 or 125 of FIG. 5 to indicate whether the call is from a third party or system subscriber, respectively. The caller identifier field may include a PSTN number or a system subscriber username as shown, for example.

Routing Controller (RC)

Referring to FIG. 7, the RC 16 is shown in greater detail and includes an RC processor circuit shown generally at 200. The RC processor circuit 200 includes a processor 202, program memory 204, a table memory 206, buffer memory 207, and an I/O port 208, all in communication with the processor 202. (As earlier indicated, there may be a plurality of processor circuits (202), memories (204), etc.) The buffer memory 207 includes a caller id buffer 209 and a callee id buffer 211.

The I/O port 208 includes a database request port 210 through which a request to the database (18 shown in FIG. 1) can be made and includes a database response port 212 for receiving a reply from the database 18. The I/O port 208 further includes an RC request message input 214 for receiving the RC request message from the call controller (14 shown in FIG. 1) and includes a routing message output 216 for sending a routing message back to the call controller 14. The I/O port 208 thus acts to receive caller identifier and a callee identifier contained in the RC request message from the call controller, the RC request message being received in response to initiation of a call by a calling subscriber.

The program memory 204 includes blocks of codes for directing the processor 202 to carry out various functions of the RC (16). One of these blocks includes an RC request message handler 250 which directs the RC to produce a routing message in response to a received RC request message. The RC request message handler process is shown in greater detail at 250 in FIGS. 8A through 8D.

RC Request Message Handler

Figure 8A:
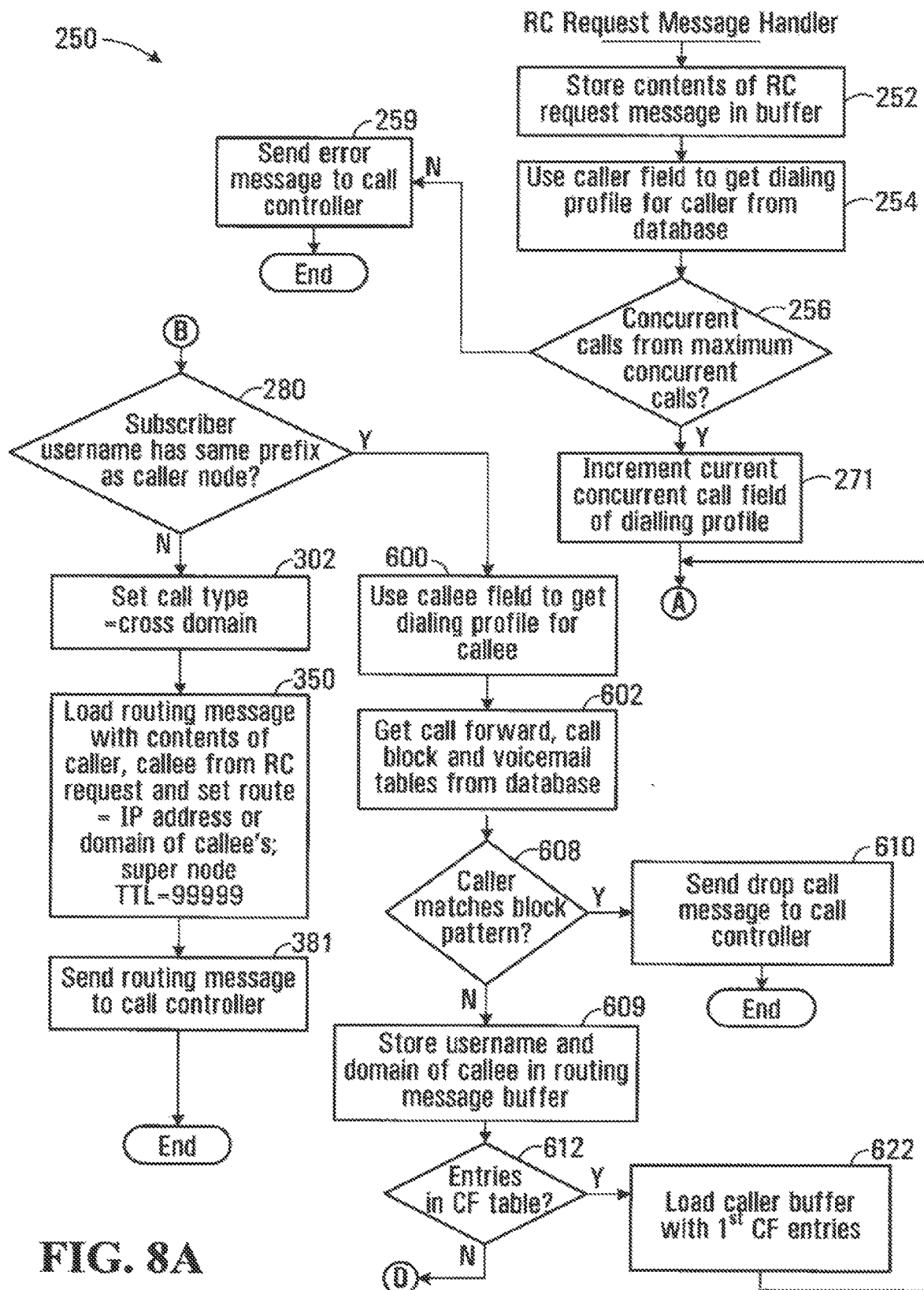
FIGS. 8A-8D is a flowchart of a RC request message handler executed by the RC processor circuit shown in FIG. 7.

Referring to FIG. 8A, the RC request message handler begins with a first block 252 that directs the RC processor circuit (200) to store the contents of the RC request message (150) in buffers in the buffer memory 207 of FIG. 7, one of which includes the caller ID buffer 209 of FIG. 7 for separately storing the contents of the callee field 154 of the RC request message. Block 254 then directs the RC processor circuit to use the contents of the caller field 152 in the RC request message shown in FIG. 6, to locate and retrieve from the database 18 a record associating calling attributes with the calling subscriber. The located record may be referred to as a dialing profile for the caller. The retrieved dialing profile may then be stored in the buffer memory 207, for example.

Referring to FIG. 9, an exemplary data structure for a dialing profile is shown generally at 253 and includes a user name field 258, a domain field 260, and calling attributes comprising a national dialing digits (NDD) field 262, an international dialing digits (IDD) field 264, a country code field 266, a local area codes field 267, a caller minimum local length field 268, a caller maximum local length field 270, a reseller field 273, a maximum number of concurrent calls field 275 and a current number of concurrent calls field 277. Effectively the dialing profile is a record identifying calling attributes of the caller identified by the caller identifier. More generally, dialing profiles represent calling attributes of respective subscribers.

An exemplary caller profile for the Vancouver subscriber is shown generally at 276 in FIG. 10 and indicates that the user name field 258 includes the user name (2001 1050 8667) that has been assigned to the subscriber and is stored in the user name field 50 in the telephone as shown in FIG. 2.

Referring back to FIG. 10, the domain field 260 includes a domain name as shown at 282, including a node type identifier 284, a location code identifier 286, a system provider identifier 288 and a domain portion 290. The domain field 260 effectively identifies a domain or node associated with the user identified by the contents of the user name field 258. In this embodiment, the node type identifier 284 includes the code "sp" identifying a supernode and the location identifier 286 identifies the supernode as being in Vancouver (YVR). The system provider identifier 288 identifies the company supplying the service and the domain portion 290 identifies the "com" domain.

The national dialled digit field 262 in this embodiment includes the digit "1" and, in general, includes a number specified by the International Telecommunications Union (ITU) Telecommunications Standardization Sector (ITU-T) E.164 Recommendation which assigns national dialing digits to countries.

The international dialing digit field 264 includes a code also assigned according to the ITU-T according to the country or location of the user.

The country code field 266 also includes the digit "1" and, in general, includes a number assigned according to the ITU-T to represent the country in which the user is located.

The local area codes field 267 includes a list of area codes that have been assigned by the ITU-T to the geographical area in which the subscriber is located. The caller minimum and maximum local number length fields 268 and 270 hold numbers representing minimum and maximum local number lengths permitted in the area code(s) specified by the contents of the local area codes field 267. The reseller field 273 is optional and holds a code identifying a retailer of the services, in this embodiment "Klondike". The maximum number of concurrent calls field 275 holds a code identifying the maximum number of concurrent calls that the user is entitled to cause to concurrently exist. This permits more than one call to occur concurrently while all calls for the user are billed to the same account. The current number of concurrent calls field 277 is initially 0 and is incremented each time a concurrent call associated with the user is initiated and is decremented when a concurrent call is terminated.

The area codes associated with the user are the area codes associated with the location code identifier 286 of the contents of the domain field 260.

A dialing profile of the type shown in FIG. 9 is produced whenever a user registers with the system or agrees to become a subscriber to the system. Thus, for example, a user wishing to subscribe to the system may contact an office maintained by a system operator and personnel in the office may ask the user certain questions about his location and service preferences, whereupon tables can be used to provide office personnel with appropriate information to be entered into the user name 258, domain 260, NDD 262, IDD 264, country code 266, local area codes 267, caller minimum and maximum local length fields 268 and 270 reseller field 273 and concurrent call fields 275 and 277 to establish a dialing profile for the user.

Referring to FIGS. 11 and 12, callee dialing profiles for users in Calgary and London, respectively for example, are shown.

In addition to creating dialing profiles when a user registers with the system, a direct-in-dial (DID) record of the type shown at 278 in FIG. 13 is added to a direct-in-dial bank table in the database (18 in FIG. 1) to associate the username and a host name of the supernode with which the user is associated, with an E.164 number associated with the user on the PSTN network.

An exemplary DID table record entry for the Calgary callee is shown generally at 300 in FIG. 14. The user name field 281 and user domain field 272 are analogous to the user name and user domain fields 258 and 260 of the caller dialing profile shown in FIG. 10. The contents of the DID field 274 include a E.164 public telephone number including a country code 283, an area code 285, an exchange code 287 and a number 289. If the user has multiple telephone numbers, then multiple records of the type shown at 300 would be included in the DID bank table, each having the same user name and user domain, but different DID field 274 contents reflecting the different telephone numbers associated with that user.

In addition to creating dialing profiles as shown in FIG. 9 and DID records as shown in FIG. 13 when a user registers with the system, call blocking records of the type shown in FIG. 26, call forwarding records of the type shown in FIG. 28 and voicemail records of the type shown in FIG. 30 may be added to the database 18 when a new subscriber is added to the system.

Referring back to FIG. 8A, after retrieving a dialing profile for the caller, such as shown at 276 in FIG. 10, the RC processor circuit 200 is directed to block 256 which directs the processor circuit (200) to determine whether the contents of the concurrent call field 277 are less then the contents of the maximum concurrent call field 275 of the dialing profile for the caller and, if so, block 271 directs the processor circuit to increment the contents of the concurrent call field 277. If the contents of concurrent call field 277 are equal to or greater than the contents of the maximum concurrent call field 275, block 259 directs the processor circuit 200 to send an error message back to the call controller (14) to cause the call controller to notify the caller that the maximum number of concurrent calls has been reached and no further calls can exist concurrently, including the presently requested call.

Assuming block 256 allows the call to proceed, the RC processor circuit 200 is directed to perform certain checks on the callee identifier provided by the contents of the callee field 154 in FIG. 6, of the RC request message 150. These checks are shown in greater detail in FIG. 8B.

Figure 8B:
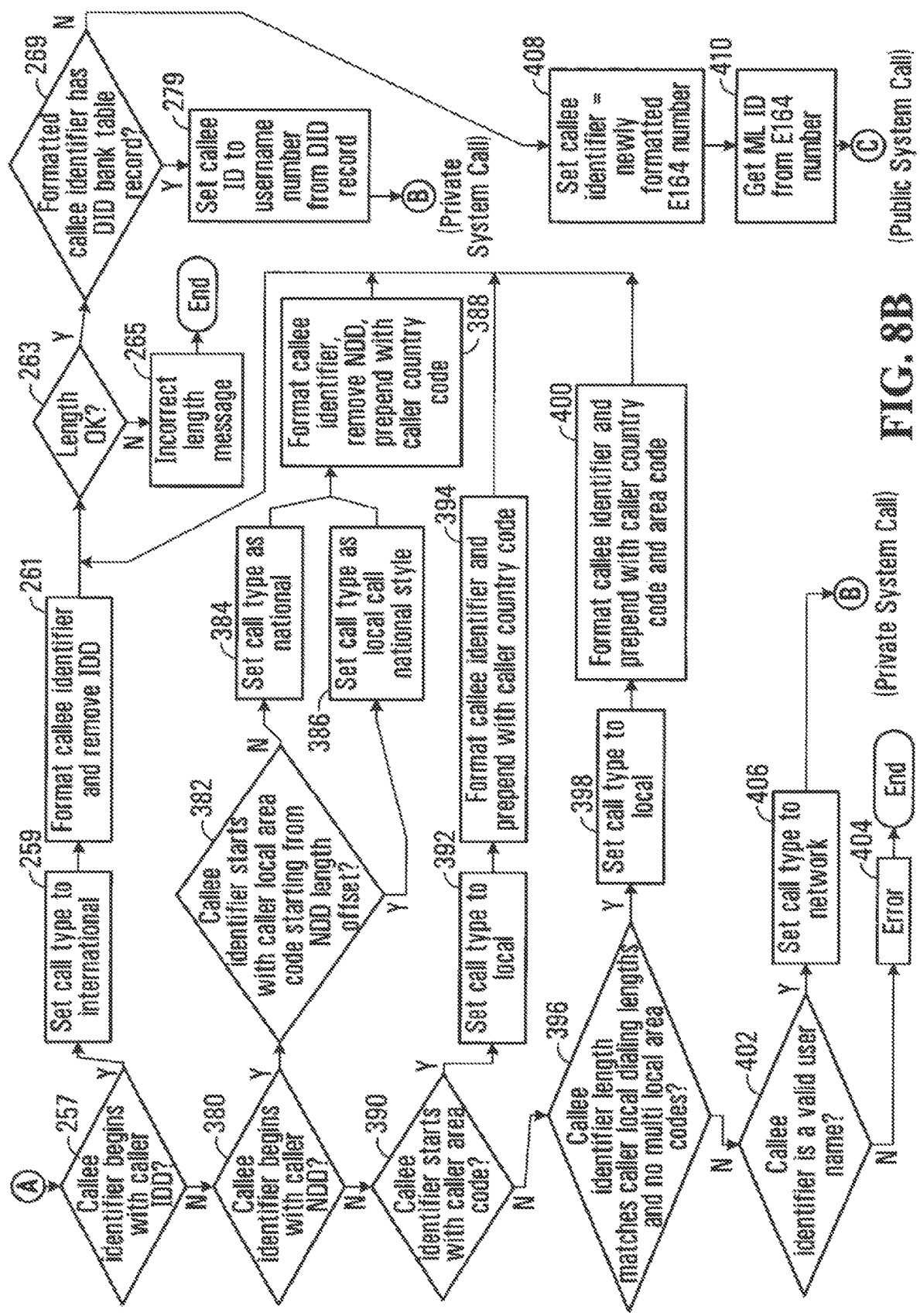

Referring to FIG. 8B, the processor (202 in FIG. 7) is directed to a first block 257 that causes it to determine whether a digit pattern of the callee identifier (154) provided in the RC request message (150) includes a pattern that matches the contents of the international dialing digits (IDD) field 264 in the caller profile shown in FIG. 10. If so, then block 259 directs the processor (202) to set a call type code identifier variable maintained by the processor to indicate that the call is an international call and block 261 directs the processor to produce a reformatted callee identifier by reformatting the callee identifier into a predefined digit format. In this embodiment, this is done by removing the pattern of digits matching the IDD field contents 264 of the caller dialing profile to effectively shorten the callee identifier. Then, block 263 directs the processor 202 to determine whether or not the callee identifier has a length which meets criteria establishing it as a number compliant with the E.164 Standard set by the ITU. If the length does not meet this criteria, block 265 directs the processor 202 to send back to the call controller (14) a message indicating the length is not correct. The process is then ended. At the call controller 14, routines (not shown) stored in the program memory 104 may direct the processor (102 of FIG. 4) to respond to the incorrect length message by transmitting a message back to the telephone (12 shown in FIG. 1) to indicate that an invalid number has been dialled.

Still referring to FIG. 8B, if the length of the amended callee identifier meets the criteria set forth at block 263, block 269 directs the processor (202 of FIG. 7) to make a database request to determine whether or not the amended callee identifier is found in a record in the direct-in-dial bank (DID) table. Referring back to FIG. 8B, at block 269, if the processor 202 receives a response from the database indicating that the reformatted callee identifier produced at block 261 is found in a record in the DID bank table, then the callee is a subscriber to the system and the call is classified as a private network call by directing the processor to block 279 which directs the processor to copy the contents of the corresponding user name field (281 in FIG. 14) from the callee DID bank table record (300 in FIG. 14) into the callee ID buffer (211 in FIG. 7). Thus, the processor 202 locates a subscriber user name associated with the reformatted callee identifier. The processor 202 is then directed to point B in FIG. 8A.

Subscriber to Subscriber Calls Between Different Nodes

Referring to FIG. 8A, block 280 directs the processor (202 of FIG. 7) to execute a process to determine whether or not the node associated with the reformatted callee identifier is the same node that is associated with the caller identifier. To do this, the processor 202 determines whether or not a prefix (e.g., continent code 61) of the callee name held in the callee ID buffer (211 in FIG. 7), is the same as the corresponding prefix of the caller name held in the username field 258 of the caller dialing profile shown in FIG. 10. If the corresponding prefixes are not the same, block 302 in FIG. 8A directs the processor (202 in FIG. 7) to set a call type flag in the buffer memory (207 in FIG. 7) to indicate the call is a cross-domain call. Then, block 350 of FIG. 8A directs the processor (202 of FIG. 7) to produce a routing message identifying an address on the private network with which the callee identified by the contents of the callee ID buffer is associated and to set a time to live for the call at a maximum value of 99999, for example.

Thus the routing message includes a caller identifier, a call identifier set according to a username associated with the located DID bank table record and includes an identifier of a node on the private network with which the callee is associated.

The node in the system with which the callee is associated is determined by using the callee identifier to address a supernode table having records of the type as shown at 370 in FIG. 17. Each record 370 has a prefix field 372 and a supernode address field 374. The prefix field 372 includes the first n digits of the callee identifier. In this embodiment n=2. The supernode address field 374 holds a code representing the IP address or a fully qualified domain name of the node associated with the code stored in the callee identifier prefix field 372. Referring to FIG. 18, for example, if the prefix is 20, the supernode address associated with that prefix is sp.yvr.digifonica.com.

Referring to FIG. 15, a generic routing message is shown generally at 352 and includes an optional supplier prefix field 354, and optional delimiter field 356, a callee user name field 358, at least one route field 360, a time to live field 362 and other fields 364. The optional supplier prefix field 354 holds a code for identifying supplier traffic. The optional delimiter field 356 holds a symbol that delimits the supplier prefix code from the callee user name field 358. In this embodiment, the symbol is a number sign (#). The route field 360 holds a domain name or IP address of a gateway or node that is to carry the call, and the time to live field 362 holds a value representing the number of seconds the call is permitted to be active, based on subscriber available minutes and other billing parameters.

Referring to FIG. 8A and FIG. 16, an example of a routing message produced by the processor at block 350 for a caller associated with a different node than the caller is shown generally at 366 and includes only a callee field 359, a route field 361 and a time to live field 362.

Referring to FIG. 8A, having produced a routing message as shown in FIG. 16, block 381 directs the processor (202 of FIG. 7) to send the routing message shown in FIG. 16 to the call controller 14 shown in FIG. 1.

Referring back to FIG. 8B, if at block 257, the callee identifier stored in the callee id buffer (211 in FIG. 7) does not begin with an international dialing digit, block 380 directs the processor (202) to determine whether or not the callee identifier begins with the same national dial digit code as assigned to the caller. To do this, the processor (202) is directed to refer to the retrieved caller dialing profile as shown in FIG. 10. In FIG. 10, the national dialing digit code 262 is the number 1. Thus, if the callee identifier begins with the number 1, then the processor (202) is directed to block 382 in FIG. 8B.

Block 382 directs the processor (202 of FIG. 7) to examine the callee identifier to determine whether or not the digits following the NDD digit identify an area code that is the same as any of the area codes identified in the local area codes field 267 of the caller dialing profile 276 shown in FIG. 10. If not, block 384 of FIG. 8B directs the processor 202 to set the call type flag to indicate that the call is a national call. If the digits following the NDD digit identify an area code that is the same as a local area code associated with the caller as indicated by the caller dialing profile, block 386 directs the processor 202 to set the call type flag to indicate a local call, national style. After executing blocks 384 or 386, block 388 directs the processor 202 to format the callee identifier into a pre-defined digit format to produce a re-formatted callee identifier by removing the national dialled digit and prepending a caller country code identified by the country code field 266 of the caller dialing profile shown in FIG. 10. The processor (202) is then directed to block 263 of FIG. 8B to perform other processing as already described above.

If at block 380, the callee identifier does not begin with a national dialled digit, block 390 directs the processor (202) to determine whether the callee identifier begins with digits that identify the same area code as the caller. Again, the reference for this is the retrieved caller dialing profile shown in FIG. 10. The processor (202) determines whether or not the first few digits of the callee identifier identify an area code corresponding to the local area code field 267 of the retrieved caller dialing profile. If so, then block 392 directs the processor 202 to set the call type flag to indicate that the call is a local call and block 394 directs the processor (202) to format the callee identifier into a pre-defined digit format to produce a reformatted callee identifier by prepending the caller country code to the callee identifier, the caller country code being determined from the country code field 266 of the retrieved caller dialing profile shown in FIG. 10. The processor (202) is then directed to block 263 for further processing as described above.

Referring back to FIG. 8B, at block 390, the callee identifier does not start with the same area code as the caller, block 396 directs the processor (202 of FIG. 7) to determine whether the number of digits in the callee identifier, i.e. the length of the callee identifier, is within the range of digits indicated by the caller minimum local number length field 268 and the caller maximum local number length field 270 of the retrieved caller dialing profile shown in FIG. 10. If so, then block 398 directs the processor (202) to set the call type flag to indicate a local call and block 400 directs the processor (202) to format the callee identifier into a pre-defined digit format to produce a reformatted callee identifier by prepending to the callee identifier the caller country code (as indicated by the country code field 266 of the retrieved caller dialing profile shown in FIG. 10) followed by the caller area code (as indicated by the local area code field 267 of the caller profile shown in FIG. 10). The processor (202) is then directed to block 263 of FIG. 8B for further processing as described above.

Referring back to FIG. 8B, if at block 396, the callee identifier has a length that does not fall within the range specified by the caller minimum local number length field (268 in FIG. 10) and the caller maximum local number length field (270 in FIG. 10), block 402 directs the processor 202 of FIG. 7 to determine whether or not the callee identifier identifies a valid user name. To do this, the processor 202 searches through the database (18 of FIG. 10 of dialing profiles to find a dialing profile having user name field contents (258 in FIG. 10) that match the callee identifier. If no match is found, block 404 directs the processor (202) to send an error message back to the call controller (14). If at block 402, a dialing profile having a user name field 258 that matches the callee identifier is found, block 406 directs the processor 202 to set the call type flag to indicate that the call is a private network call and then the processor is directed to block 280 of FIG. 8A. Thus, the call is classified as a private network call when the callee identifier identifies a subscriber to the private network.

From FIG. 8B, it will be appreciated that there are certain groups of blocks of codes that direct the processor 202 in FIG. 7 to determine whether the callee identifier has certain features such as an international dialing digit, a national dialing digit, an area code and a length that meet certain criteria, and cause the processor 202 to reformat the callee identifier stored in the callee id buffer 211, as necessary into a predetermined target format including only a country code, area code, and a normal telephone number, for example, to cause the callee identifier to be compatible with the E.164 number plan standard in this embodiment. This enables block 269 in FIG. 8B to have a consistent format of callee identifiers for use in searching through the DID bank table records of the type shown in FIG. 13 to determine how to route calls for subscriber to subscriber calls on the same system. Effectively, therefore blocks 257, 380, 390, 396 and 402 establish call classification criteria for classifying the call as a public network call or a private network call. Block 269 classifies the call, depending on whether or not the formatted callee identifier has a DID bank table record and this depends on how the call classification criteria are met and block 402 directs the processor 202 of FIG. 7 to classify the call as a private network call when the callee identifier complies with a pre-defined format, i.e. is a valid user name and identifies a subscriber to the private network, after the callee identifier has been subjected to the classification criteria of blocks 257, 380, 390 and 396.

Subscriber to Non-Subscriber Calls

Not all calls will be subscriber to subscriber calls and this will be detected by the processor 202 of FIG. 7 when it executes block 269 in FIG. 8B, and does not find a DID bank table record that is associated with the callee, in the DID bank table. When this occurs, the call is classified as a public network call by directing the processor 202 to block 408 of FIG. 8B which causes it to set the contents of the callee id buffer 211 of FIG. 7 equal to the newly formatted callee identifier, i.e., a number compatible with the E.164 standard. Then, block 410 of FIG. 8B directs the processor (202) to search a database of route or master list records associating route identifiers with dialing codes shown in FIG. 19 to locate a router having a dialing code having a number pattern matching at least a portion of the reformatted callee identifier.

Referring to FIG. 19, a data structure for a master list or route list record is shown. Each master list record includes a master list ID field 500, a dialing code field 502, a country code field 504, a national sign number field 506, a minimum length field 508, a maximum length field 510, a national dialed digit field 512, an international dialed digit field 514 and a buffer rate field 516.

The master list ID field 500 holds a unique code such as 1019, for example, identifying the record. The dialing code field 502 holds a predetermined number pattern that the processor 202 of FIG. 7 uses at block 410 in FIG. 8B to find the master list record having a dialing code matching the first few digits of the amended callee identifier stored in the callee id buffer 211. The country code field 504 holds a number representing the country code associated with the record and the national sign number field 506 holds a number representing the area code associated with the record. (It will be observed that the dialing code is a combination of the contents of the country code field 504 and the national sign number field 506.) The minimum length field 508 holds a number representing the minimum length of digits associated with the record and the maximum length field 51 holds a number representing the maximum number of digits in a number with which the record may be compared. The national dialed digit (NDD) field 512 holds a number representing an access code used to make a call within the country specified by the country code, and the international dialed digit (IDD) field 514 holds a number representing the international prefix needed to dial a call from the country indicated by the country code.

Thus, for example, a master list record may have a format as shown in FIG. 20 with exemplary field contents as shown.

Referring back to FIG. 8B, using the country code and area code portions of the reformatted callee identifier stored in the callee id buffer 211, block 410 directs the processor 202 of FIG. 7 to find a master list record such as the one shown in FIG. 20 having a dialing code that matches the country code (1) and area code (604) of the callee identifier. Thus, in this example, the processor (202) would find a master list record having an ID field containing the number 1019. This number may be referred to as a route ID. Thus, a route ID number is found in the master list record associated with a predetermined number pattern in the reformatted callee identifier.

Figure 8C:
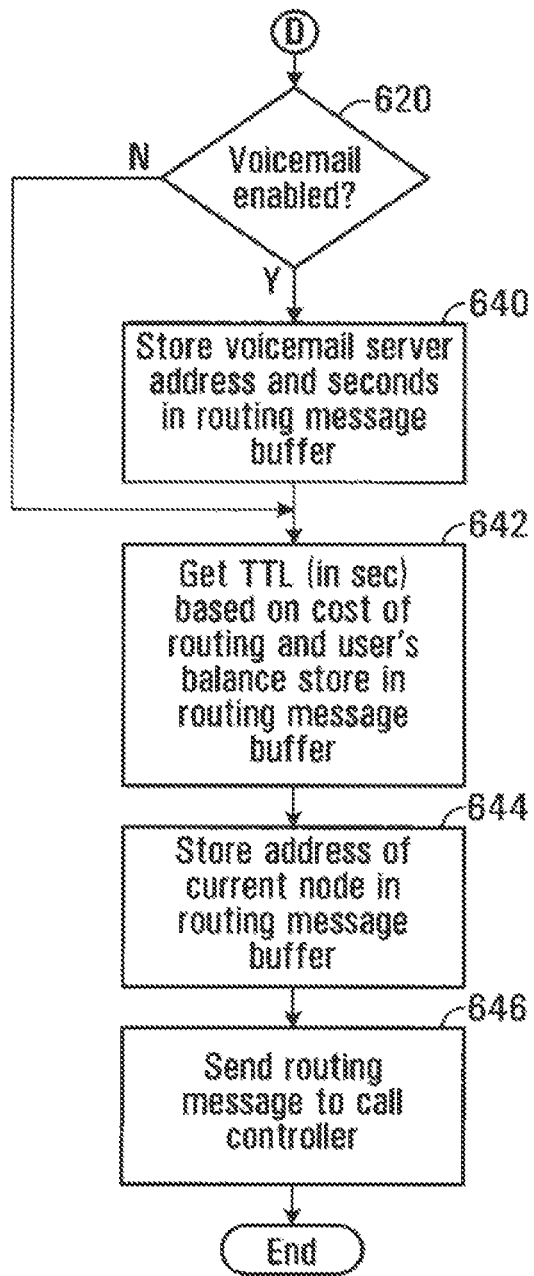
Figure 8D:
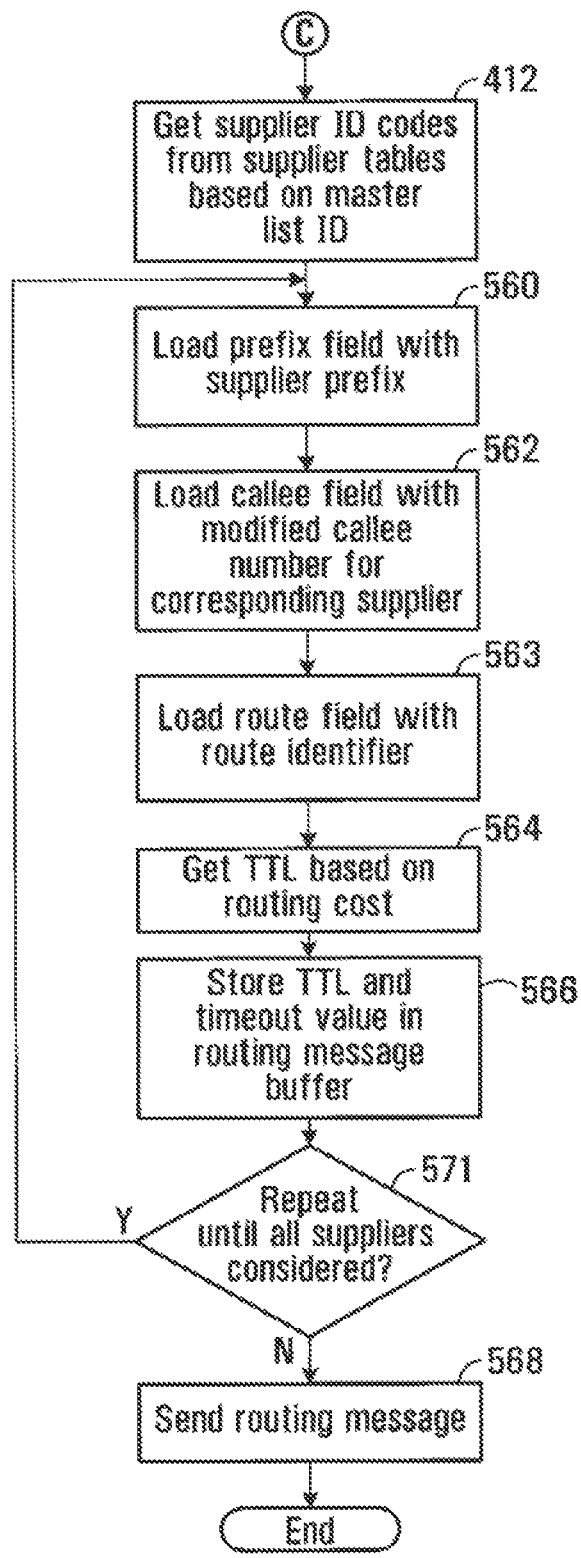

After executing block 410 in FIG. 8B, the process continues as shown in FIG. 8D. Referring to FIG. 8D, block 412 directs the processor 202 of FIG. 7 to use the route ID number to search a database of supplier records associating supplier identifiers with route identifiers to locate at least one supplier record associated with the route identifier to identify at least one supplier operable to supply a communications link for the route.

Referring to FIG. 21, a data structure for a supplier list record is shown. Supplier list records include a supplier ID field 540, a master list ID field 542, an optional prefix field 544, a specific route identifier field 546, a NDD/IDD rewrite field 548, a rate field 550, and a timeout field 551. The supplier ID field 540 holds a code identifying the name of the supplier and the master list ID field 542 holds a code for associating the supplier record with a master list record. The prefix field 544 holds a string used to identify the supplier traffic and the specific route identifier field 546 holds an IP address of a gateway operated by the supplier indicated by the supplier ID field 540. The NDD/IDD rewrite field 548 holds a code representing a rewritten value of the NDD/IDD associated with this route for this supplier, and the rate field 550 holds a code indicating the cost per second to the system operator to use the route provided by the gateway specified by the contents of the route identifier field 546. The timeout field 551 holds a code indicating a time that the call controller should wait for a response from the associated gateway before giving up and trying the next gateway. This time value may be in seconds, for example. Exemplary supplier records are shown in FIGS. 22, 23 and 24 for the exemplary suppliers shown at 20 in FIG. 1, namely Telus, Shaw and Sprint.

Referring back to FIG. 8D, at block 412 the processor 202 finds all supplier records that identify the master list ID found at block 410 of FIG. 8B.

Referring back to FIG. 8D, block 560 directs the processor 202 of FIG. 7 to begin to produce a routing message of the type shown in FIG. 15. To do this, the processor 202 loads a routing message buffer as shown in FIG. 25 with a supplier prefix of the least costly supplier where the least costly supplier is determined from the rate fields 550 of FIG. 21 of the records associated with respective suppliers.

Referring to FIGS. 22-24, in the embodiment shown, the supplier "Telus" has the lowest number in the rate field 550 and therefore the prefix 4973 associated with that supplier is loaded into the routing message buffer shown in FIG. 25 first. Block 562 in FIG. 8D directs the processor to delimit the prefix 4973 by the number sign (#) and to next load the reformatted callee identifier into the routing message buffer shown in FIG. 25. At block 563 of FIG. 8D, the contents of the route identifier field 546 of FIG. 21 of the record associated with the supplier "Telus" are added by the processor 202 of FIG. 7 to the routing message buffer shown in FIG. 25 after an @ sign delimiter, and then block 564 in FIG. 8D directs the processor to get a time to live value, which in one embodiment may be 3600 seconds, for example. Block 566 then directs the processor 202 to load this time to live value and the timeout value (551) in FIG. 21 in the routing message buffer of FIG. 25. Accordingly, a first part of the routing message for the Telus gateway is shown generally at 570 in FIG. 25.

Referring back to FIG. 8D, block 571 directs the processor 202 back to block 560 and causes it to repeat blocks 560, 562, 563, 564 and 566 for each successive supplier until the routing message buffer is loaded with information pertaining to each supplier identified by the processor at block 412. Thus, a second portion of the routing message as shown at 572 in FIG. 25 relates to the second supplier identified by the record shown in FIG. 23. Referring back to FIG. 25, a third portion of the routing message as shown at 574 and is associated with a third supplier as indicated by the supplier record shown in FIG. 24.

Consequently, referring to FIG. 25, the routing message buffer holds a routing message identifying a plurality of different suppliers able to provide gateways to the public telephone network (i.e. specific routes) to establish at least part of a communication link through which the caller may contact the callee. In this embodiment, each of the suppliers is identified, in succession, according to rate. Other criteria for determining the order in which suppliers are listed in the routing message may include preferred supplier priorities which may be established based on service agreements, for example.

Referring back to FIG. 8D, block 568 directs the processor 202 of FIG. 7 to send the routing message shown in FIG. 25 to the call controller 14 in FIG. 1.

Subscriber to Subscriber Calls within the Same Node

Referring back to FIG. 8A, if at block 280, the callee identifier received in the RC request message has a prefix that identifies the same node as that associated with the caller, block 600 directs the processor 202 to use the callee identifier in the callee id buffer 211 to locate and retrieve a dialing profile for the callee. The dialing profile may be of the type shown in FIG. 11 or 12, for example. Block 602 of FIG. 8A then directs the processor 202 of FIG. 7 to get call block, call forward and voicemail records from the database 18 of FIG. 1 based on the user name identified in the callee dialing profile retrieved by the processor at block 600. Call block, call forward and voicemail records may be as shown in FIGS. 26, 27, 28 and 30 for example.

Referring to FIG. 26, the call block records include a user name field 604 and a block pattern field 606. The user name field holds a user name corresponding to the user name in the user name field (258 in FIG. 10) of the callee profile and the block pattern field 606 holds one or more E.164-compatible numbers or user names identifying PSTN numbers or system subscribers from whom the subscriber identified in the user name field 604 does not wish to receive calls.

Referring to FIG. 8A and FIG. 27, block 608 directs the processor 202 of FIG. 7 to determine whether or not the caller identifier received in the RC request message matches a block pattern stored in the block pattern field 606 of the call block record associated with the callee identified by the contents of the user name field 604 in FIG. 26. If the caller identifier matches a block pattern, block 610 directs the processor to send a drop call or non-completion message to the call controller (14) and the process is ended. If the caller identifier does not match a block pattern associated with the callee, block 609 directs the processor to store the username and domain of the callee, as determined from the callee dialing profile, and a time to live value in the routing message buffer as shown at 650 in FIG. 32. Referring back to FIG. 8A, block 612 then directs the processor 202 to determine whether or not call forwarding is required.

Referring to FIG. 28, the call forwarding records include a user name field 614, a destination number field 616, and a sequence number field 618. The user name field 614 stores a code representing a user with which the record is associated. The destination number field 616 holds a user name representing a number to which the current call should be forwarded, and the sequence number field 618 holds an integer number indicating the order in which the user name associated with the corresponding destination number field 616 should be attempted for call forwarding. The call forwarding table may have a plurality of records for a given user. The processor 202 of FIG. 7 uses the contents of the sequence number field 618 to place the records for a given user in order. As will be appreciated below, this enables the call forwarding numbers to be tried in an ordered sequence.

Referring to FIG. 8A and FIG. 29, if at block 612, the call forwarding record for the callee identified by the callee identifier contains no contents in the destination number field 616 and accordingly no contents in the sequence number field 618, there are no call forwarding entries for this callee, and the processor 202 is directed to block 620 in FIG. 8C. If there are entries in the call forwarding table 27, block 622 in FIG. 8A directs the processor 202 to search the dialing profile table to find a dialing profile record as shown in FIG. 9, for the user identified by the destination number field 616 of the call forward record shown in FIG. 28. The processor 202 of FIG. 7 is further directed to store the username and domain for that user and a time to live value in the routing message buffer as shown at 652 in FIG. 32, to produce a routing message as illustrated. This process is repeated for each call forwarding record associated with the callee identified by the callee id buffer 211 in FIG. 7 to add to the routing message buffer all call forwarding usernames and domains associated with the callee.

Referring back to FIG. 8A, if at block 612 there are no call forwarding records, then at block 620 in FIG. 8C the processor 202 is directed to determine whether or not the user identified by the callee identifier has paid for voicemail service. This is done by checking to see whether or not a flag is set in a voicemail record of the type shown in FIG. 30 in a voicemail table stored in the database 18 shown in FIG. 1.

Referring to FIG. 30, voicemail records in this embodiment may include a user name field 624, a voicemail server field 626, a seconds to voicemail field 628 and an enable field 630. The user name field 624 stores the user name of the callee. The voicemail server field 626 holds a code identifying a domain name of a voicemail server associated with the user identified by the user name field 624. The seconds to voicemail field 628 holds a code identifying the time to wait before engaging voicemail, and the enable field 630 holds a code representing whether or not voicemail is enabled for the user. Referring back to FIG. 8C, at block 620 if the processor 202 of FIG. 7 finds a voicemail record as shown in FIG. 30 having user name field 624 contents matching the callee identifier, the processor is directed to examine the contents of the enabled field 630 to determine whether or not voicemail is enabled. If voicemail is enabled, then block 640 in FIG. 8C directs the processor 202 to FIG. 7 to store the contents of the voicemail server field 626 and the contents of the seconds to voicemail field 628 in the routing message buffer, as shown at 654 in FIG. 32. Block 642 then directs the processor 202 to get time to live values for each path specified by the routing message according to the cost of routing and the user's balance. These time to live values are then appended to corresponding paths already stored in the routing message buffer.

Referring back to FIG. 8C, block 644 then directs the processor 202 of FIG. 7 to store the IP address of the current node in the routing message buffer as shown at 656 in FIG. 32. Block 646 then directs the processor 202 to send the routing message shown in FIG. 32 to the call controller 14 in FIG. 1. Thus in the embodiment described the routing controller will produce a routing message that will cause at least one of the following: forward the call to another party, block the call and direct the caller to a voicemail server.

Referring back to FIG. 1, the routing message whether of the type shown in FIG. 16, 25 or 32, is received at the call controller 14 and the call controller interprets the receipt of the routing message as a request to establish a call.

Referring to FIG. 4, the program memory 104 of the call controller 14 includes a routing to gateway routine depicted generally at 122.

Where a routing message of the type shown in FIG. 32 is received by the call controller 14, the routing to gateway routine 122 shown in FIG. 4 may direct the processor 102 cause a message to be sent back through the internet 13 shown in FIG. 1 to the callee telephone 15, knowing the IP address of the callee telephone 15 from the user name.

Alternatively, if the routing message is of the type shown in FIG. 16, which identifies a domain associated with another node in the system, the call controller may send a SIP invite message along the high speed backbone 17 connected to the other node. The other node functions as explained above, in response to receipt of a SIP invite message.

If the routing message is of the type shown in FIG. 25 where there are a plurality of gateway suppliers available, the call controller sends a SIP invite message to the first supplier, in this case Telus, using a dedicated line or an internet connection to determine whether or not Telus is able to handle the call. If the Telus gateway returns a message indicating it is not able to handle the call, the call controller 14 then proceeds to send a SIP invite message to the next supplier, in this case Shaw. The process is repeated until one of the suppliers responds indicating that it is available to carry the call. Once a supplier responds indicating that it is able to carry the call, the supplier sends back to the call controller 14 an IP address for a gateway provided by the supplier through which the call or audio path of the call will be carried. This IP address is sent in a message from the call controller 14 to the media relay 9 which responds with a message indicating an IP address to which the caller telephone should send its audio/video, traffic and an IP address to which the gateway should send its audio/video for the call. The call controller conveys the IP address at which the media relay expects to receive audio/video from the caller telephone, to the caller telephone 12 in a message. The caller telephone replies to the call controller with an IP address at which it would like to receive audio/video and the call controller conveys that IP address to the media relay. The call may then be conducted between the caller and callee through the media relay and gateway.

Referring back to FIG. 1, if the call controller 14 receives a routing message of the type shown in FIG. 32, and which has at least one call forwarding number and/or a voicemail number, the call controller attempts to establish a call to the callee telephone 15 by seeking from the callee telephone a message indicating an IP address to which the media relay should send audio/video. If no such message is received from the callee telephone, no call is established. If no call is established within a pre-determined time, the call controller 14 attempts to establish a call with the next user identified in the call routing message in the same manner. This process is repeated until all call forwarding possibilities have been exhausted, in which case the call controller communicates with the voicemail server 19 identified in the routing message to obtain an IP address to which the media relay should send audio/video and the remainder of the process mentioned above for establishing IP addresses at the media relay 9 and the caller telephone is carried out to establish audio/video paths to allowing the caller to leave a voicemail message with the voicemail server.

When an audio/video path through the media relay is established, a call timer maintained by the call controller 14 logs the start date and time of the call and logs the call ID and an identification of the route (i.e., audio/video path IP address) for later use in billing.

Time to Live

Figure 33A:
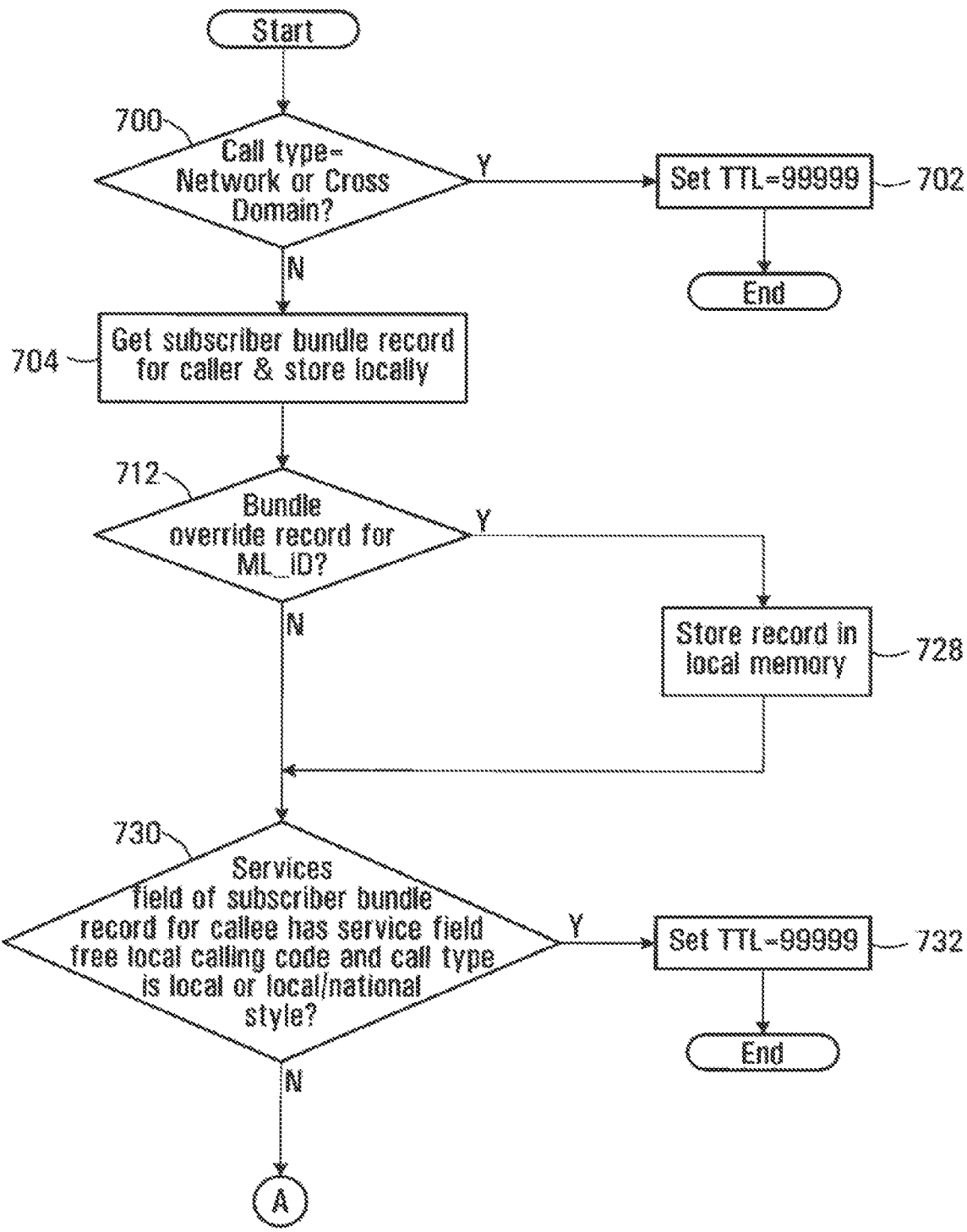
FIGS. 33A and 33B are respective portions of a flowchart of a process executed by the RC processor for determining a time to live value.
Figure 33B:
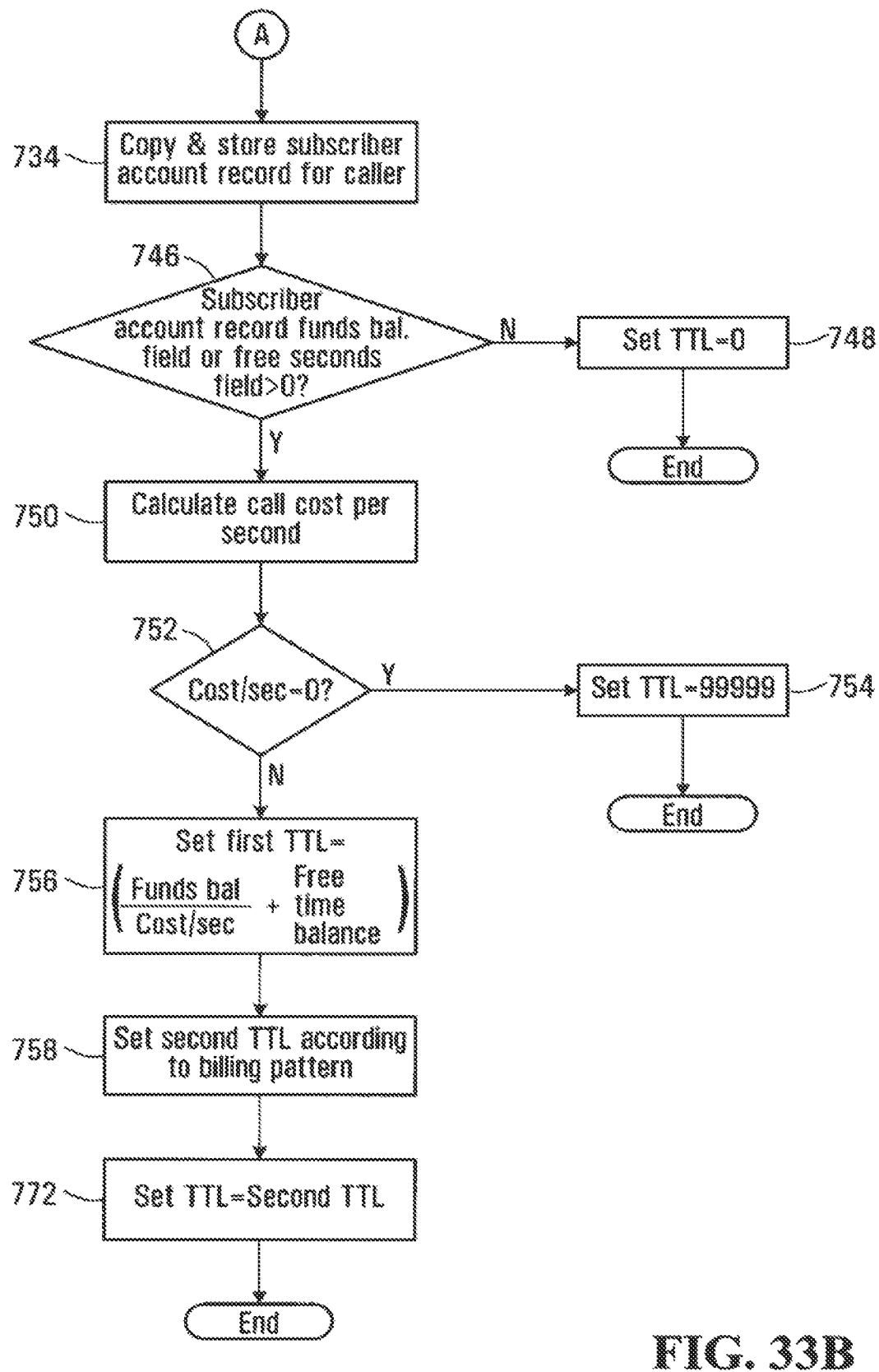

Referring to FIGS. 33A and 33B, a process for determining a time to live value for any of blocks 642 in FIG. 8C, 350 in FIG. 8A or 564 in FIG. 8D above is described. The process is executed by the processor 202 shown in FIG. 7. Generally, the process involves calculating a cost per unit time, calculating a first time value as a sum of a free time attributed to a participant in the communication session and the quotient of a funds balance held by the participant to the cost per unit time value and producing a second time value in response to the first time value and a billing pattern associated with the participant, the billing pattern including first and second billing intervals and the second time value being the time to permit a communication session to be conducted.

Referring to FIG. 33A, in this embodiment, the process begins with a first block 700 that directs the RC processor to determine whether or not the call type set at block 302 in FIG. 8A indicates the call is a network or cross-domain call. If the call is a network or cross-domain call, block 702 of FIG. 33A directs the RC processor to set the time to live equal to 99999 and the process is ended. Thus, the network or cross-domain call type has a long time to live. If at block 700 the call type is determined not to be a network or cross-domain type, block 704 directs the RC processor to get a subscriber bundle table record from the database 18 in FIG. 1 and store it locally in the subscriber bundle record buffer at the RC 14.

Referring to FIG. 34, a subscriber bundle table record is shown generally at 706. The record includes a user name field 708 and a services field 710. The user name field 708 holds a code identifying the subscriber user name and the services field 710 holds codes identifying service features assigned to the subscriber, such as free local calling, call blocking and voicemail, for example.

FIG. 35 shows an exemplary subscriber bundle record for the Vancouver caller. In this record the user name field 708 is loaded with the user name 2001 1050 8667 and the services field 710 is loaded with codes 10, 14 and 16 corresponding to free local calling, call blocking and voicemail, respectively. Thus, user 2001 1050 8667 has free local calling, call blocking and voicemail features.

Referring back to FIG. 33A, after having loaded a subscriber bundle record into the subscriber bundle record buffer, block 712 directs the RC processor to search the database (18) determine whether or not there is a bundle override table record for the master list ID value that was determined at block 410 in FIG. 8B. An exemplary bundle override table record is shown at 714 in FIG. 36. The bundle table record includes a master list ID field 716, an override type field 718, an override value field 720 a first interval field 722 and a second interval field 724. The master list ID field 716 holds a master list ID code. The override type field 718 holds an override type code indicating a fixed, percent or cent amount to indicate the amount by which a fee will be increased. The override value field 720 holds a real number representing the value of the override type. The first interval field 722 holds a value indicating the minimum number of seconds for a first level of charging and the second interval field 724 holds a number representing a second level of charging.

Referring to FIG. 37, a bundle override record for the located master list ID code is shown generally at 726 and includes a master list ID field 716 holding the code 1019 which was the code located in block 410 of FIG. 8B. The override type field 718 includes a code indicating the override type is a percentage value and the override value field 720 holds the value 10.0 indicating that the override will be 10.0% of the charged value. The first interval field 722 holds a value representing 30 seconds and the second interval field 724 holds a value representing 6 seconds. The 30 second value in the first interval field 722 indicates that charges for the route will be made at a first rate for 30 seconds and thereafter the charges will be made at a different rate in increments of 6 seconds, as indicated by the contents of the second interval field 724.

Referring back to FIG. 33A, if at block 712 the processor finds a bundle override record of the type shown in FIG. 37, block 728 directs the processor to store the bundle override record in local memory. In the embodiment shown, the bundle override record shown in FIG. 37 is stored in the bundle override record buffer at the RC as shown in FIG. 7. Still referring to FIG. 33A, block 730 then directs the RC processor to determine whether or not the subscriber bundle table record 706 in FIG. 35 has a services field including a code identifying that the user is entitled to free local calling and also directs the processor to determine whether or not the call type is not a cross domain cell, i.e. it is a local or local/national style. If both of these conditions are satisfied, block 732 directs the processor to set the time to live equal to 99999, giving the user a long period of time for the call. The process is then ended. If the conditions associated with block 730 are not satisfied, block 734 of FIG. 33B directs the RC processor to retrieve a subscriber account record associated with a participant in the call. This is done by copying and storing in the subscriber account record buffer a subscriber account record for the caller.

Referring to FIG. 38, an exemplary subscriber account table record is shown generally at 736. The record includes a user name field 738, a funds balance field 740 and a free time field 742. The user name field 738 holds a subscriber user name, the funds balance field 740 holds a real number representing the dollar value of credit available to the subscriber and the free time field 742 holds an integer representing the number of free seconds that the user is entitled to.

An exemplary subscriber account record for the Vancouver caller is shown generally at 744 in FIG. 39, wherein the user name field 738 holds the user name 2001 1050 8667, the funds balance field 740 holds the value $10.00, and the free time field 742 holds the value 100. The funds balance field holding the value of $10.00 indicates the user has $10.00 worth of credit and the free time field having the value of 100 indicates that the user has a balance of 100 free seconds of call time.

Referring back to FIG. 33B, after copying and storing the subscriber account record shown in FIG. 39 from the database to the subscriber account record buffer RC, block 746 directs the processor to determine whether or not the subscriber account record funds balance field 740 or free time field 742 are greater than zero. If they are not greater than zero, block 748 directs the processor to set the time to live equal to zero and the process is ended. The RC then sends a message back to the call controller to cause the call controller to deny the call to the caller. If the conditions associated with block 746 are satisfied, block 750 directs the processor to calculate the call cost per unit time. A procedure for calculating the call cost per unit time is described below in connection with FIG. 41.

Assuming the procedure for calculating the cost per second returns a number representing the call cost per second, block 752 directs the processor 202 in FIG. 7 to determine whether or not the cost per second is equal to zero. If so, block 754 directs the processor to set the time to live to 99999 to give the caller a very long length of call and the process is ended.

If at block 752 the call cost per second is not equal to zero, block 756 directs the processor 202 in FIG. 7 to calculate a first time to live value as a sum of a free time attributed to the participant in the communication session and the quotient of the funds balance held by the participant to the cost per unit time value. To do this, the processor 202 of FIG. 7 is directed to set a first time value or temporary time to live value equal to the sum of the free time provided in the free time field 742 of the subscriber account record shown in FIG. 39 and the quotient of the contents of the funds balance field 740 in the subscriber account record for the call shown in FIG. 39 and the cost per second determined at block 750 of FIG. 33B. Thus, for example, if at block 750 the cost per second is determined to be three cents per second and the funds balance field holds the value $10.00, the quotient of the funds balance and cost per second is 333 seconds and this is added to the contents of the free time field 742, which is 100, resulting in a time to live of 433 seconds.

Block 758 then directs the RC processor to produce a second time value in response to the first time value and the billing pattern associated with the participant as established by the bundle override record shown in FIG. 37. This process is shown in greater detail at 760 in FIG. 40 and generally involves producing a remainder value representing a portion of the second billing interval remaining after dividing the second billing interval into a difference between the first time value and the first billing interval.

Figure 40:
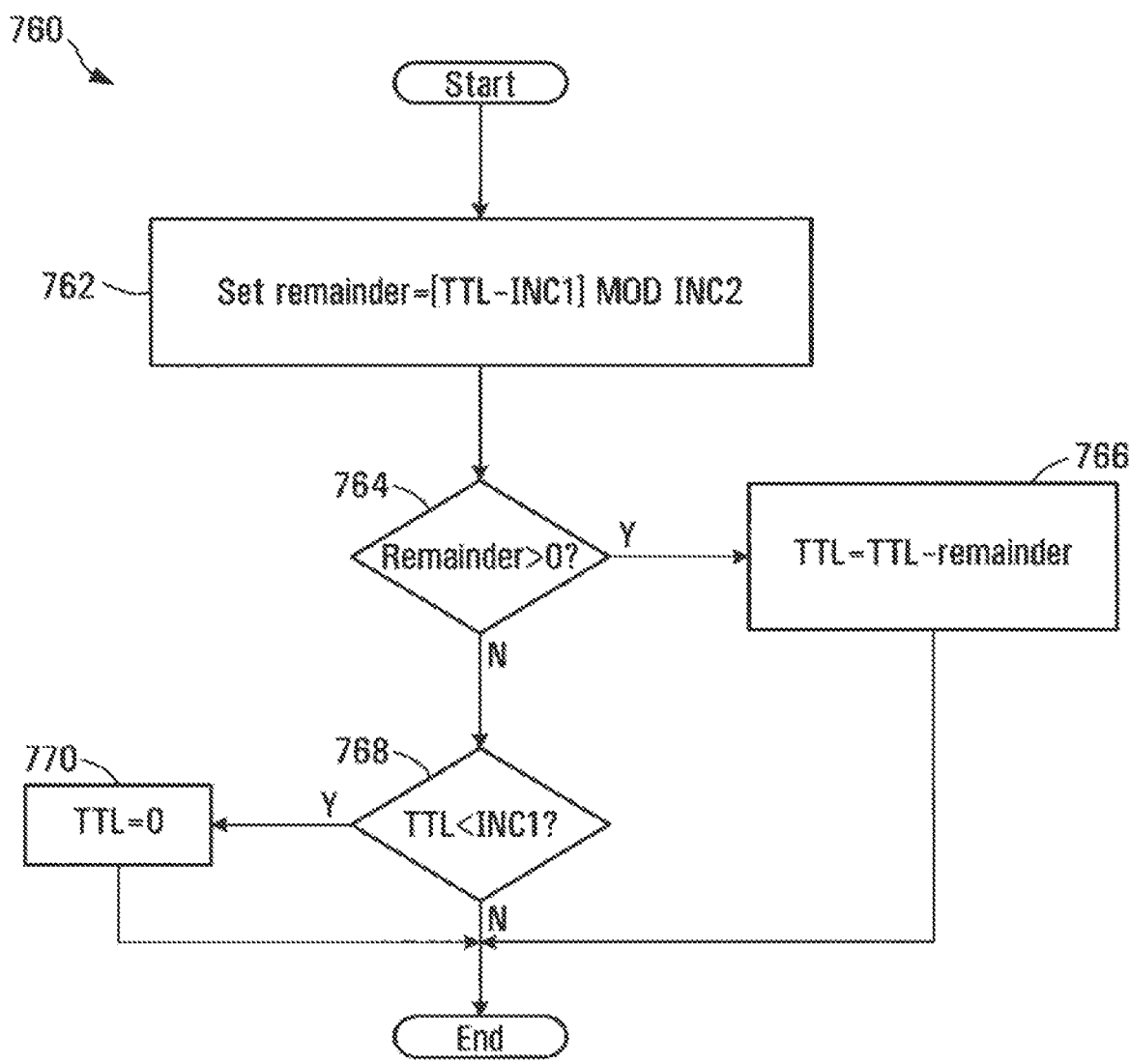
FIG. 40 is a flowchart of a process for producing a second time value executed by the RC processor circuit shown in FIG. 7.

Referring to FIG. 40, the process for producing the second time value begins with a first block 762 that directs the processor 202 in FIG. 7 to set a remainder value equal to the difference between the time to live value calculated at block 756 in FIG. 33B and the contents of the first interval field 722 of the record shown in FIG. 37, multiplied by the modulus of the contents of the second interval field 724 of FIG. 37. Thus, in the example given, the difference between the time to live field and the first interval field is 433 minus 30, which is 403 and therefore the remainder produced by the mod of 403 divided by 6 is 0.17. Block 764 then directs the processor to determine whether or not this remainder value is greater than zero and, if so, block 766 directs the processor to subtract the remainder from the first time value and set the difference as the second time value. To do this the processor is directed to set the time to live value equal to the current time to live of 403 minus the remainder of 1, i.e., 402 seconds. The processor is then returned back to block 758 of FIG. 33B.

Referring back to FIG. 40, if at block 764 the remainder is not greater than zero, block 768 directs the processor 202 of FIG. 7 to determine whether or not the time to live is less than the contents of the first interval field 722 in the record shown in FIG. 37. If so, then block 770 of FIG. 40 directs the processor to set the time to live equal to zero. Thus, the second time value is set to zero when the remainder is greater than zero and the first time value is less than the free time associated with the participant in the call. If at block 768 the conditions of that block are not satisfied, the processor returns the first time to live value as the second time to live value.

Thus, referring to FIG. 33B, after having produced a second time to live value, block 772 directs the processor to set the time to live value for use in blocks 342, 350 or 564.

Cost Per Second

Referring back to FIG. 33B, at block 750 it was explained that a call cost per unit time is calculated. The following explains how that call cost per unit time value is calculated.

Figure 41:
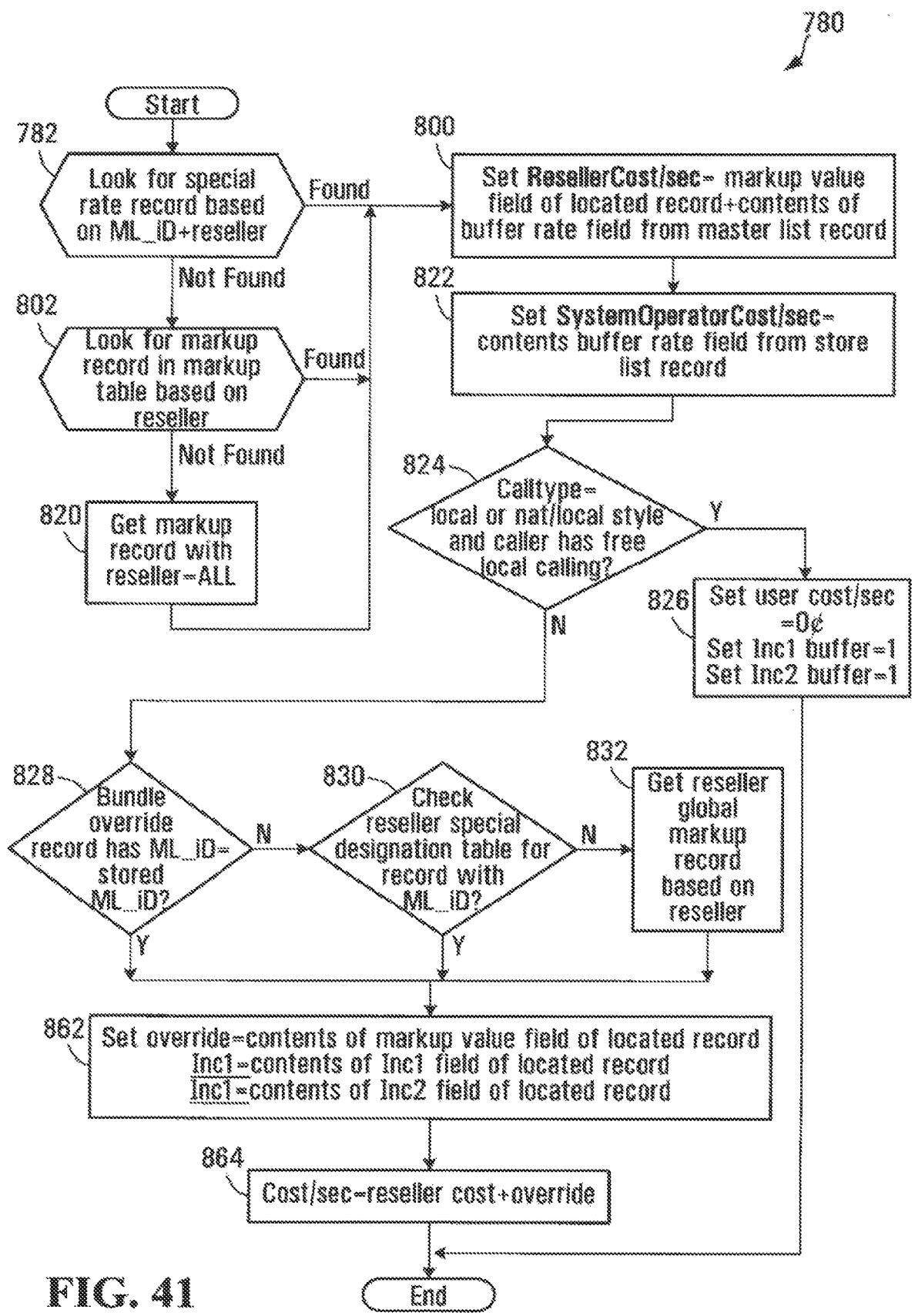
FIG. 41 is a flowchart for calculating a call cost per unit time.

Referring to FIG. 41, a process for calculating a cost per unit time is shown generally at 780. The process is executed by the processor 202 in FIG. 7 and generally involves locating a record in a database, the record comprising a markup type indicator, a markup value and a billing pattern and setting a reseller rate equal to the sum of the markup value and the buffer rate, locating at least one of an override record specifying a route cost per unit time amount associated with a route associated with the communication session, a reseller record associated with a reseller of the communications session, the reseller record specifying a reseller cost per unit time associated with the reseller for the communication session and a default operator markup record specifying a default cost per unit time and setting as the cost per unit time the sum of the reseller rate and at least one of the route cost per unit time, the reseller cost per unit time and the default cost per unit time.

The process begins with a first set of blocks 782, 802 and 820 which direct the processor 202 in FIG. 7 to locate at least one of a record associated with a reseller and a route associated with the reseller, a record associated with the reseller, and a default reseller mark-up record. Block 782, in particular, directs the processor to address the database 18 to look for a record associated with a reseller and a route with the reseller by looking for a special rate record based on the master list ID established at block 410 in FIG. 8C.

Referring to FIG. 42, a system operator special rate table record is shown generally at 784. The record includes a reseller field 786, a master list ID field 788, a mark-up type field 790, a mark-up value field 792, a first interval field 794 and a second interval field 796. The reseller field 786 holds a reseller ID code and the master list ID field 788 holds a master list ID code. The mark-up type field 790 holds a mark-up type such as fixed percent or cents and the mark-up value field 792 holds a real number representing the value corresponding to the mark-up type. The first interval field 794 holds a number representing a first level of charging and the second interval field 796 holds a number representing a second level of charging.

An exemplary system operator special rate table for a reseller known as "Klondike" is shown at 798 in FIG. 43. In this record, the reseller field 786 holds a code indicating the retailer ID is Klondike, the master list ID field 788 holds the code 1019 to associate the record with the master list ID code 1019. The mark-up type field 790 holds a code indicating the mark-up type is cents and the mark-up value field 792 holds a mark-up value indicating $\frac{1}{10}$ of one cent. The first interval field 794 holds the value 30 and the second interval field 796 holds the value 6, these two fields indicating that the operator allows 30 seconds for free and then billing is done in increments of 6 seconds after that.

Referring back to FIG. 41, if at block 782 a record such as the one shown in FIG. 43 is located in the system operator special rates table, the processor is directed to block 800 in FIG. 41. If such a record is not found in the system operator special rates table, block 802 directs the processor to address the database 18 to look in a system operator mark-up table for a mark-up record associated with the reseller.

Referring to FIG. 44, an exemplary system operator mark-up table record is shown generally at 804. The record includes a reseller field 806, a mark-up type field 808, a mark-up value field 810, a first interval field 812 and a second interval field 814. The reseller mark-up type, mark-up value, first interval and second interval fields are as described in connection with the fields by the same names in the system operator special rates table shown in FIG. 42.

FIG. 45 provides an exemplary system operator mark-up table record for the reseller known as Klondike and therefore the reseller field 806 holds the value "Klondike", the mark-up type field 808 holds the value cents, the mark-up value field holds the value 0.01, the first interval field 812 holds the value 30 and the second interval field 814 holds the value 6. This indicates that the reseller "Klondike" charges by the cent at a rate of one cent per minute. The first 30 seconds of the call are free and billing is charged at the rate of one cent per minute in increments of 6 seconds.

FIG. 46 provides an exemplary system operator mark-up table record for cases where no specific system operator mark-up table record exists for a particular reseller, i.e., a default reseller mark-up record. This record is similar to the record shown in FIG. 45 and the reseller field 806 holds the value "all", the mark-up type field 808 is loaded with a code indicating mark-up is based on a percentage, the mark-up value field 810 holds the percentage by which the cost is marked up, and the first and second interval fields 812 and 814 identify first and second billing levels.

Referring back to FIG. 41, if at block 802 a specific mark-up record for the reseller identified at block 782 is not located, block 820 directs the processor to get the mark-up record shown in FIG. 46, having the "all" code in the reseller field 806. The processor is then directed to block 800.

Referring back to FIG. 41, at block 800, the processor 202 of FIG. 7 is directed to set a reseller rate equal to the sum of the mark-up value of the record located by blocks 782, 802 or 820 and the buffer rate specified by the contents of the buffer rate field 516 of the master list record shown in FIG. 20. To do this, the RC processor sets a variable entitled "reseller cost per second" to a value equal to the sum of the contents of the mark-up value field (792, 810) of the associated record, plus the contents of the buffer rate field (516) from the master list record associated with the master list ID. Then, block 822 directs the processor to set a system operator cost per second variable equal to the contents of the buffer rate field (516) from the master list record. Block 824 then directs the processor to determine whether the call type flag indicates the call is local or national/local style and whether the caller has free local calling. If both these conditions are met, then block 826 sets the user cost per second variable equal to zero and sets two increment variables equal to one, for use in later processing. The cost per second has thus be calculated and the process shown in FIG. 41 is ended.

If at block 824 the conditions of that block are not met, the processor 202 of FIG. 7 is directed to locate at least one of a bundle override table record specifying a route cost per unit time associated with a route associated with the communication session, a reseller special destinations table record associated with a reseller of the communications session, the reseller record specifying a reseller cost per unit time associated with the reseller for the communication session and a default reseller global markup record specifying a default cost per unit time.

To do this block 828 directs the processor 202 of FIG. 7 to determine whether or not the bundle override record 726 in FIG. 37 located at block 712 in FIG. 33A has a master list ID equal to the stored master list ID that was determined at block 410 in FIG. 8B. If not, block 830 directs the processor to find a reseller special destinations table record in a reseller special destinations table in the database (18), having a master list ID code equal to the master list ID code of the master list ID that was determined at block 410 in FIG. 8B. An exemplary reseller special destinations table record is shown in FIG. 47 at 832. The reseller special destinations table record includes a reseller field 834, a master list ID field 836, a mark-up type field 838, a mark-up value field 840, a first interval field 842 and a second interval field 844. This record has the same format as the system operator special rates table record shown in FIG. 42, but is stored in a different table to allow for different mark-up types and values and time intervals to be set according to resellers' preferences. Thus, for example, an exemplary reseller special destinations table record for the reseller "Klondike" is shown at 846 in FIG. 48. The reseller field 834 holds a value indicating the reseller as the reseller "Klondike" and the master list ID field holds the code 1019. The mark-up type field 838 holds a code indicating the mark-up type is percent and the mark-up value field 840 holds a number representing the mark-up value as 5%. The first and second interval fields identify different billing levels used as described earlier.

Referring back to FIG. 41, the record shown in FIG. 48 may be located at block 830, for example. If at block 830 such a record is not found, then block 832 directs the processor to get a default operator global mark-up record based on the reseller ID.

Referring to FIG. 49, an exemplary default reseller global mark-up table record is shown generally at 848. This record includes a reseller field 850, a mark-up type field 852, a mark-up value field 854, a first interval field 856 and a second interval field 858. The reseller field 850 holds a code identifying the reseller. The mark-up type field 852, the mark-up value field 854 and the first and second interval fields 856 and 858 are of the same type as described in connection with fields of the same name in FIG. 47, for example. The contents of the fields of this record 860 may be set according to system operator preferences, for example.

Referring to FIG. 50, an exemplary reseller global mark-up table record is shown generally at 860. In this record, the reseller field 850 holds a code indicating the reseller is "Klondike", the mark-up type field 852 holds a code indicating the mark-up type is percent, the mark-up value field 854 holds a value representing 10% as the mark-up value, the first interval field 856 holds the value 30 and the second interval field 858 holds the values 30 and 6 respectively to indicate the first 30 seconds are free and billing is to be done in 6 second increments after that.

Referring back to FIG. 41, should the processor get to block 832, the reseller global mark-up table record as shown in FIG. 50 is retrieved from the database and stored locally at the RC. As seen in FIG. 41, it will be appreciated that if the conditions are met in blocks 828 or 830, or if the processor executes block 832, the processor is then directed to block 862 which causes it to set an override value equal to the contents of the mark-up value field of the located record, to set the first increment variable equal to the contents of the first interval field of the located record and to set the second increment variable equal to the contents of the second interval field of the located record. (The increment variables were alternatively set to specific values at block 826 in FIG. 41.)

It will be appreciated that the located record could be a bundle override record of the type shown in FIG. 37 or the located record could be a reseller special destination record of the type shown in FIG. 48 or the record could be a reseller global mark-up table record of the type shown in FIG. 50. After the override and first and second increment variables have been set at block 862, the processor 202 if FIG. 7 is directed to set as the cost per unit time the sum of the reseller rate and at least one of the route cost per unit time, the reseller cost per unit time and the default cost per unit time, depending on which record was located. To do this, block 864 directs the processor to set the cost per unit time equal to the sum of the reseller cost set at block 800 in FIG. 41, plus the contents of the override variable calculated in block 862 in FIG. 41. The cost per unit time has thus been calculated and it is this cost per unit time that is used in block 752 of FIG. 33B, for example.

Terminating the Call

In the event that either the caller or the callee terminates a call, the telephone of the terminating party sends a SIP bye message to the controller 14. An exemplary SIP bye message is shown at 900 in FIG. 51 and includes a caller field 902, a callee field 904 and a call ID field 906. The caller field 902 holds a twelve digit user name, the callee field 904 holds a PSTN compatible number or user name, and the call ID field 906 holds a unique call identifier field of the type shown in the call ID field 65 of the SIP invite message shown in FIG. 3.

Thus, for example, referring to FIG. 52, a SIP bye message for the Calgary callee is shown generally at 908 and the caller field 902 holds a user name identifying the caller, in this case 2001 1050 8667, the callee field 904 holds a user name identifying the Calgary callee, in this case 2001 1050 2222, and the call ID field 906 holds the code FA10 @ 192.168.0.20, which is the call ID for the call.

Figure 53:
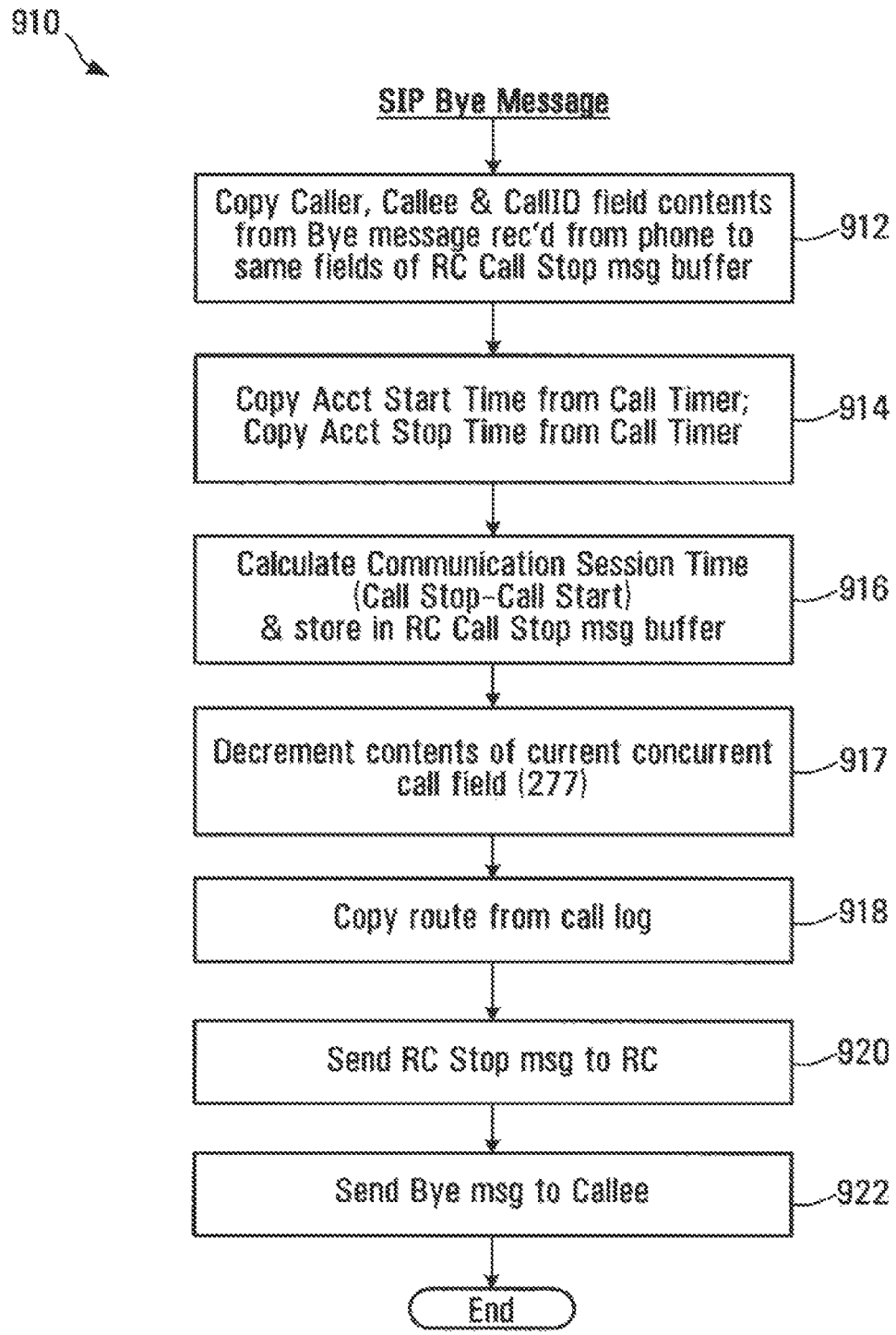
FIG. 53 is a flowchart of a process executed by the call controller for producing a RC stop message in response to receipt of a SIP bye message.

The SIP bye message shown in FIG. 52 is received at the call controller 14 and the call controller executes a process as shown generally at 910 in FIG. 53. The process includes a first block 912 that directs the call controller processor 202 of FIG. 7 to copy the caller, callee and call ID field contents from the SIP bye message received from the terminating party to corresponding fields of an RC stop message buffer (not shown). Block 914 then directs the processor to copy the call start time from the call timer and to obtain a call stop time from the call timer. Block 916 then directs the call controller to calculate a communication session time by determining the difference in time between the call start time and the call stop time. This session time is then stored in a corresponding field of the RC call stop message buffer. Block 917 then directs the processor to decrement the contents of the current concurrent call field 277 of the dialing profile for the caller as shown in FIG. 10, to indicate that there is one less concurrent call in progress. A copy of the amended dialing profile for the caller is then stored in the database 18 of FIG. 1. Block 918 then directs the processor to copy the route from the call log. An RC call stop message produced as described above is shown generally at 1000 in FIG. 54. An RC call stop message specifically associated with the call made to the Calgary callee is shown generally at 1020 in FIG. 55.

Referring to FIG. 54, the RC stop call message includes a caller field 1002, callee field 1004, a call ID field 1006, an account start time field 1008, an account stop time field 1010, a communication session time 1012 and a route field 1014. The caller field 1002 holds a username, the callee field 1004 holds a PSTN-compatible number or system number, the call ID field 1006 hold the unique call identifier received from the SIP invite message shown in FIG. 3, the account start time field 1008 holds the date and start time of the call, the account stop time field 1010 holds the date and time the call ended, the communication session time field 1012 holds a value representing the difference between the start time and the stop time, in seconds, and the route field 1014 holds the IP address for the communications link that was established.

Referring to FIG. 55, an exemplary RC stop call message for the Calgary callee is shown generally at 1020. In this example the caller field 1002 holds the user name 2001 1050 8667 identifying the Vancouver-based caller and the callee field 1004 holds the user name 2001 1050 2222 identifying the Calgary callee. The contents of the call ID field 1006 are FA10@ 192.168.0.20. The contents of the account start time field 1008 are 2006-12-30 12:12:12 and the contents of the account stop time field are 2006-12-30 12:12:14. The contents of the communication session time field 1012 are 2 to indicate 2 seconds call duration and the contents of the route field are 72.64.39.58.

Referring back to FIG. 53, after having produced an RC call stop message, block 920 directs the processor 202 in FIG. 7 to send the RC stop message compiled in the RC call stop message buffer to the RC 16 of FIG. 1. Block 922 directs the call controller 14 to send a "bye" message back to the party that did not terminate the call.

Figure 56A:
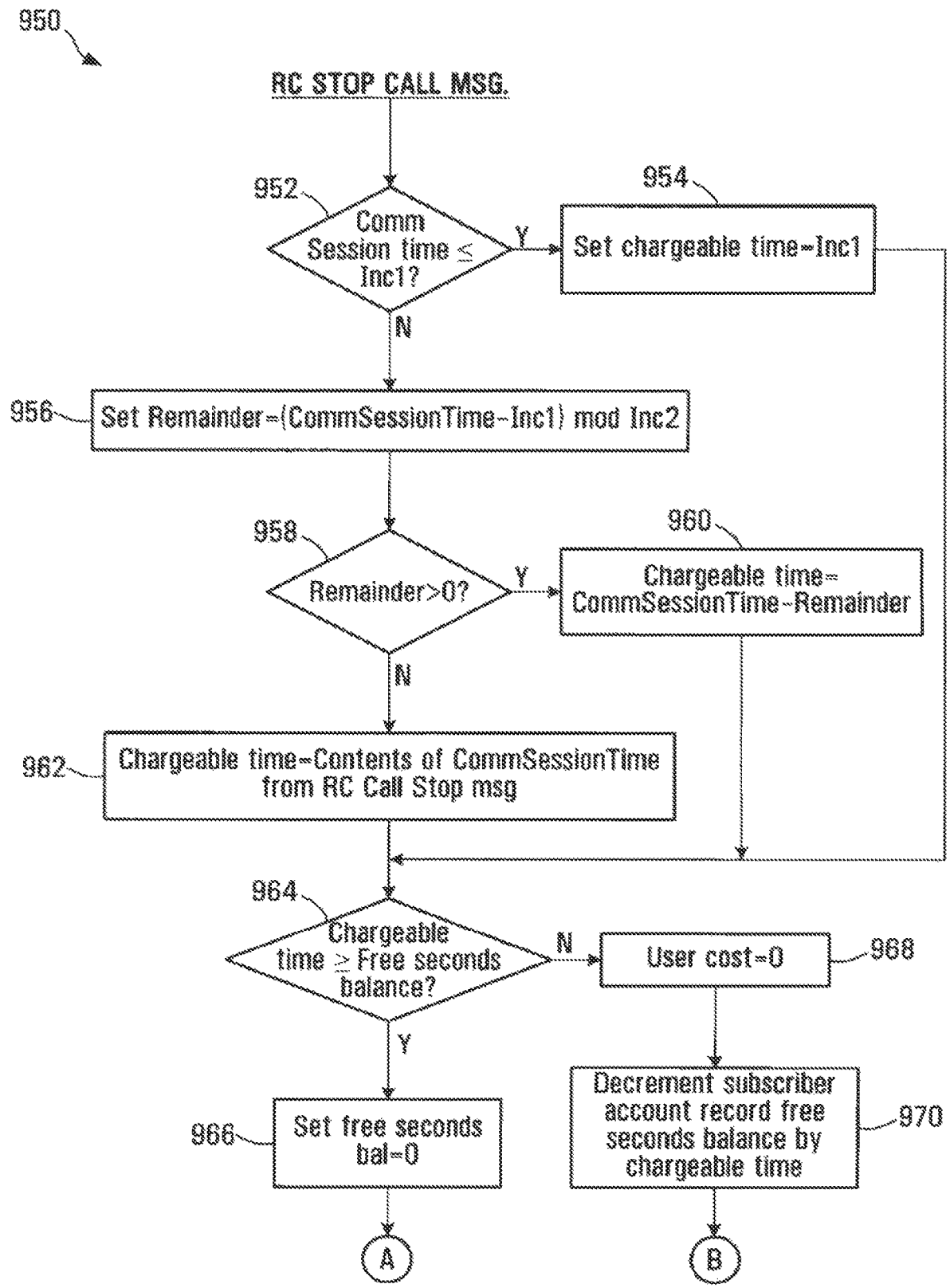
FIGS. 56A and 56B are respective portions of a flowchart of a RC call stop message handling routine executed by the RC shown in FIG. 1.
Figure 56B:
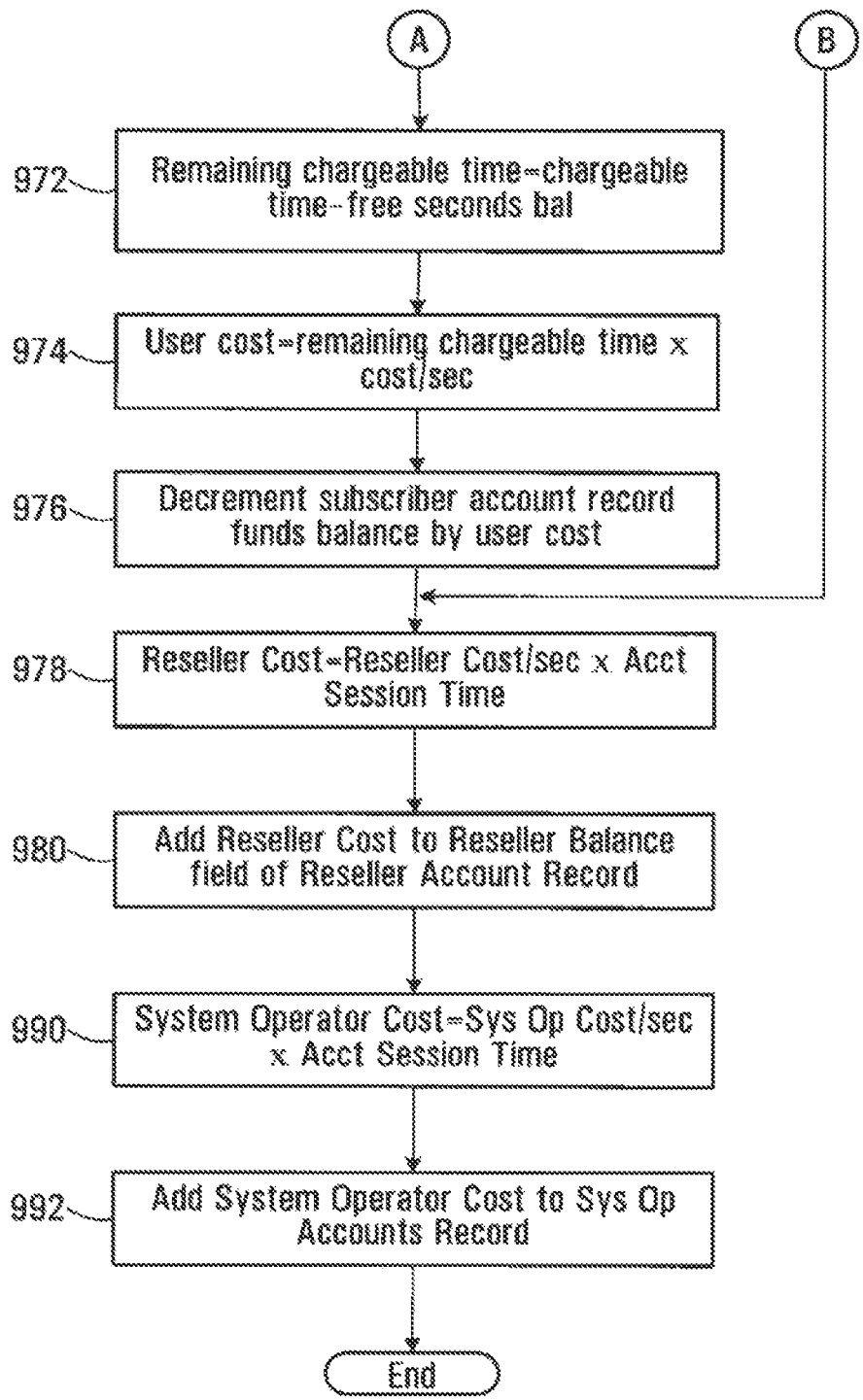

The RC 16 of FIG. 1 receives the call stop message and an RC call stop message process is invoked at the RC, the process being shown at 950 in FIGS. 56A, 56B and 56C. Referring to FIG. 56A, the RC stop message process 950 begins with a first block 952 that directs the processor 202 in FIG. 7 to determine whether or not the communication session time is less than or equal to the first increment value set by the cost calculation routine shown in FIG. 41, specifically blocks 826 or 862 thereof. If this condition is met, then block 954 of FIG. 56A directs the RC processor to set a chargeable time variable equal to the first increment value set at block 826 or 862 of FIG. 41. If at block 952 of FIG. 56A the condition is not met, block 956 directs the RC processor to set a remainder variable equal to the difference between the communication session time and the first increment value mod the second increment value produced at block 826 or 862 of FIG. 41. Then, the processor is directed to block 958 of FIG. 56A which directs it to determine whether or not the remainder is greater than zero. If so, block 960 directs the RC processor to set the chargeable time variable equal to the difference between the communication session time and the remainder value. If at block 958 the remainder is not greater than zero, block 962 directs the RC processor to set the chargeable time variable equal to the contents of the communication session time from the RC stop message. The processor is then directed to block 964. In addition, after executing block 954 or block 960, the processor is directed to block 964.

Block 964 directs the processor 202 of FIG. 7 to determine whether or not the chargeable time variable is greater than or equal to the free time balance as determined from the free time field 742 of the subscriber account record shown in FIG. 39. If this condition is satisfied, block 966 of FIG. 56A directs the processor to set the free time field 742 in the record shown in FIG. 39, to zero. If the chargeable time variable is not greater than or equal to the free time balance, block 968 directs the RC processor to set a user cost variable to zero and Block 970 then decrements the free time field 742 of the subscriber account record for the caller by the chargeable time amount determined by block 954, 960 or 962.

If at Block 964 the processor 202 of FIG. 7 was directed to Block 966 which causes the free time field (742 of FIG. 39) to be set to zero, referring to FIG. 56B, Block 972 directs the processor to set a remaining chargeable time variable equal to the difference between the chargeable time and the contents of the free time field (742 of FIG. 39). Block 974 then directs the processor to set the user cost variable equal to the product of the remaining chargeable time and the cost per second calculated at Block 750 in FIG. 33B. Block 976 then directs the processor to decrement the funds balance field (740) of the subscriber account record shown in FIG. 39 by the contents of the user cost variable calculated at Block 974.

After completing Block 976 or after completing Block 970 in FIG. 56A, block 978 of FIG. 56B directs the processor 202 of FIG. 7 to calculate a reseller cost variable as the product of the reseller rate as indicated in the mark-up value field 810 of the system operator mark-up table record shown in FIG. 45 and the communication session time determined at Block 916 in FIG. 53. Then, Block 980 of FIG. 56B directs the processor to add the reseller cost to the reseller balance field 986 of a reseller account record of the type shown in FIG. 57 at 982.

The reseller account record includes a reseller ID field 984 and the aforementioned reseller balance field 986. The reseller ID field 984 holds a reseller ID code, and the reseller balance field 986 holds an accumulated balance of charges.

Referring to FIG. 58, a specific reseller accounts record for the reseller "Klondike" is shown generally at 988. In this record the reseller ID field 984 holds a code representing the reseller "Klondike" and the reseller balance field 986 holds a balance of $100.02. Thus, the contents of the reseller balance field 986 in FIG. 58 are incremented by the reseller cost calculated at block 978 of FIG. 56B.

Still referring to FIG. 56B, after adding the reseller cost to the reseller balance field as indicated by Block 980, Block 990 directs the processor to 202 of FIG. 7 calculate a system operator cost as the product of the system operator cost per second, as set at block 822 in FIG. 41, and the communication session time as determined at Block 916 in FIG. 53. Block 992 then directs the processor to add the system operator cost value calculated at Block 990 to a system operator accounts table record of the type shown at 994 in FIG. 59. This record includes a system operator balance field 996 holding an accumulated charges balance. Referring to FIG. 60 in the embodiment described, the system operator balance field 996 may hold the value $1,000.02 for example, and to this value the system operator cost calculated at Block 990 is added when the processor executes Block 992 of FIG. 56B.

Ultimately, the final reseller balance 986 in FIG. 58 holds a number representing an amount owed to the reseller by the system operator and the system operator balance 996 of FIG. 59 holds a number representing an amount of profit for the system operator.

While specific embodiments of the invention have been described and illustrated, such embodiments should be considered illustrative of the invention only and not as limiting the invention as construed in accordance with the accompanying claims.

What is claimed is:

1. A method for routing a communication in a communication system between a first participant device, on an Internet Protocol (IP) network, associated with a first participant, and a second participant device associated with a second participant, the method comprising:
in response to initiation of the communication by the first participant device, receiving, by at least one processor, a second participant identifier associated with the second participant device;
causing the at least one processor to access a user profile that is specific to the first participant and stored in at least one memory, the user profile being associated with a plurality of first participant attributes;
comparing at least a portion of the second participant identifier with at least one of the plurality of first participant attributes associated with the user profile of the first participant, using the at least one processor and identifying whether at least one route exists whereby the communication may be routed to the second participant device;
when the at least one route is associated with a first communication network, producing a message comprising route information identifying an Internet Protocol (IP) address, on the first communication network, associated with the second participant device, using the at least one processor, and causing the communication to be established to the second participant device using the first communication network; and
when the at least one route is associated with a second communication network, producing message comprising route information identifying an Internet Protocol (IP) address associated with a gateway to the second communication network, using the at least one processor, and causing the communication to the second participant device to be established using the gateway to the second communication network.

2. The method of claim 1, wherein:
the first communication network is an Internet protocol (IP) network; and
the second communication network is a switched circuit network, and wherein the method further comprises:
producing a device identifier representing a communication device on one of the first communication network or the second communication network; and
causing a database of subscribers to be searched to identify whether the device identifier is associated with a subscriber of the first network, wherein:
if the device identifier is found in the database of subscribers, causing the Internet Protocol (IP) address to identify a network element on the first communication network; and
if the device identifier is not found in the database of subscribers, causing the Internet Protocol (IP) address to identify the gateway to the second communication network.

3. The method of claim 2, wherein the Internet address, on the first communication network, associated with the second participant device comprises an address of a communication system node associated with the second participant device, the communication system node being one of a plurality of communication system nodes each operably configured to provide communications services to a plurality of communication system subscribers.

4. The method of claim 3 further comprising determining whether the first participant device and the second participant device are associated with the same communication system node, and if so, selecting the at least one route to carry the communication to the second participant device using the first communication network.

5. The method of claim 2, further comprising:
accessing at least one database to locate communication blocking information associated with the second participant, using the at least one processor; and
blocking the communication when the communication blocking information associated with the second participant identifies the first participant identifier.

6. The method of claim 2, further comprising:
accessing at least one database to locate communication forwarding information associated with the second participant, using the at least one processor; and
forwarding the communication to at least one destination communication device based on the communication forwarding information.

7. The method of claim 6, wherein the communication forwarding information for the second participant comprises identifiers for a plurality of destination communication devices.

8. The method of claim 2, further comprising:
processing a plurality of communications from the first participant device to a plurality of destination communication devices to identify respective available routes associated with establishing each of the plurality of communications as a first network communication or a second network communication; and
producing a respective plurality of messages, each respective message comprising route information identifying an IP address, on the first communication network, associated with a respective communication device or identifying an IP address associated with a gateway to the second communication network;

wherein each message causes the respective communication to be established to the respective destination communication device based on the identified respective available route.

9. The method of claim 1, further comprising:
(a) processing a plurality of communication device identifiers produced by comparing a plurality of participant identifiers with the user profile for the first participant, to determine whether each respective communication device identifier is associated with a subscriber to the communication system, wherein:
   (i) when the respective communication device identifier is associated with a subscriber to the communication system, producing a respective message comprising route information identifying an address, on the first communication network, associated with the second participant device; and
   (ii) when the respective communication device identifier is not associated with a subscriber to the communication system, producing a respective message comprising route information identifying an address of a gateway to the second communication network; and
(b) establishing communications to communication devices respectively associated with the plurality of communication device identifiers in response to each of the respective messages.

10. The method of claim 9 further comprising identifying the at least one route by determining whether the second participant identifier corresponds to a pre-defined username format, and if so, causing the route information in the message to identify a network element in the first communication network operable to carry the communication to the second participant device using the first communication network.

11. The method of claim 9 further comprising querying a plurality of gateways regarding whether each of the gateways is able to handle the communication until at least one gateway from the plurality of gateways indicates that it is available to carry the communication, and establishing the communication to the second participant device using at least one IP address associated with the gateway that indicates that it is available to carry the communication.

12. The method of claim 9 further comprising, if the second participant device does not receive the communication in response to initiation of the communication, storing the communication on a server in association with the second participant identifier to facilitate the second participant device retrieving the communication from the server.

13. The method of claim 1, further comprising identifying the at least one route by causing a database of records to be searched to locate a Direct-Inward-Dial (DID) record associating a public telephone number with said second participant device; and
   if said DID record is found, selecting the at least one route to carry the communication to the second participant device using the first communication network and if said DID record is not found, selecting the at least one route to carry the communication to the second participant device using the second communication network.

14. The method of claim 1 further comprising:
(a) identifying route information representing a plurality of possible paths for routing the communication from the first participant device to the second participant device;
(b) processing a routing cost associated with each of the plurality of possible paths for routing the communication; and
(c) producing a routing message comprising at least some of the route information and a time to live for the communication, based on the step of processing the routing cost.

15. The method of claim 1, further comprising:
processing at least one user-specific first participant attribute, using the at least one processor, to determine whether a further communication that was initiated by the first participant to a third participant device is allowed to proceed;
if the at least one processor determines that the further communication is not allowed to proceed based on the at least one user-specific first participant attribute, preventing the further communication from being established;
if the further communication is allowed to proceed, causing a database of subscribers to be searched to identify a device identifier associated with the second participant device, wherein if a registration of the device identifier in the database of subscribers is found, causing the Internet Protocol (IP) address to identify a network element on the first communication network, and if the registration in the database of subscribers is not found, causing the Internet Protocol (IP) address to identify the gateway to the second communication network.

16. The method of claim 15, wherein:
if the further communication is allowed to proceed based on the userspecific first participant attribute, causing the at least one processor to search a database for communication blocking information associated with the third participant device, and if the communication blocking information is found, preventing the further communication from being established; and
if the further communication is allowed to proceed based on the at least one user-specific first participant attribute and no communication blocking information associated with the third participant device is found in the database, causing the at least one processor to produce a corresponding message comprising route information to cause the further communication to be established to the third participant device;
wherein the device identifier in the database of subscribers comprises at least one of a username and a Direct-Inward-Dial (DID) number.

17. A non-transitory computer readable medium encoded with instructions for directing at least one processor to execute the method of claim 15.

18. The method of claim 1, further comprising causing the at least one processor to:
determine whether the user profile for the second participant exists in at least one database; and
if the user profile for the second participant does not exist in the at least one database, cause the communication to be established to the second communication device via the second communication network.

19. The method of claim 18, further comprising causing the at least one processor to:
if the user profile for the second participant exists in the at least one database, cause the communication to be established to the second communication device via the first communication network.

20. The method of claim 19 further comprising using information associated with the user profile for the second participant to identify at least one IP address of a network element capable of carrying the communication to the second participant device.

21. The method of claim 1 wherein the message comprising route information identifying an Internet Protocol (IP) address is produced in parts, and wherein at least one part of the message comprising route information causes the communication to be established.

22. The method of claim 21 further comprising collecting data comprising the route information in a buffer prior to causing the communication to be established.

23. The method of claim 1 wherein producing the message comprising route information identifying an Internet Protocol (IP) address comprises identifying a plurality of network element addresses representing a plurality of routes for routing the communication, and using at least one of the plurality of routes to cause the communication to be established.

24. The method of claim 1 wherein identifying whether at least one route exists comprises locating at least one Direct-Inward-Dial (DID) record associating a public telephone number of the second participant device with an identifier of a network element with which the second participant device is currently associated, and causing the communication to be routed to the second participant device based on the identifier of the network element with which the second participant device is currently associated.

25. The method of claim 1 wherein identifying whether at least one route exists comprises causing at least one database to be searched to locate information associating a public telephone number of the second participant device with a user profile of the second participant that identifies a network elements with which the second participant device is currently associated, and causing the communication to be routed to the second participant device based on the identifier of the network element with which the second participant device is currently associated.

26. The method of claim 1 further comprising causing at least one database to be searched to locate information associating a public telephone number of the second participant device with an address of a network element with which the second participant device is currently associated, and sending the message comprising route information to the network element to facilitate the communication being routed to the second participant device.

27. A method for routing communications in a packet switched communication system between a first participant device associated with a first participant, and a second participant device associated with a second participant, the method comprising:
in response a communication being initiated from the first participant device to the second participant device, receiving, by at least one processor, a second participant identifier associated with the second participant device;
causing the at least one processor to load a plurality of first participant attributes obtained from a user profile for the first participant into at least one memory;
comparing at least a portion of the second participant identifier with at least one of the plurality of first participant attributes obtained from the user profile for the first participant, using the at least one processor, to produce a device identifier for use in identifying availability of a route whereby the communication may be routed to the second participant device;
identifying at least a portion of the route whereby the communication may be routed to the second participant device by causing a database of records to be searched to locate a Direct-Inward-Dial (DID) record associating a public telephone number with said second participant device, wherein if said DID record is found, identifying the at least one portion of the route to carry the communication to the second participant device using the first communication network, and wherein if said DID record is not found, identifying the at least portion of the route to carry the communication to the second participant device using the second communication network;
causing a message to be produced comprising route information identifying an Internet Protocol (IP) address associated with the at least a portion of the route to cause the communication to be established to the second participant device, wherein the route information is associated with either the first communication network or the second communication network;
wherein, when the at least a portion of the route is associated with the first communication network, the Internet Protocol (IP) address is used by a communication controller to cause the communication to be established to the second participant device using the first communication network; and
wherein, when the at least a portion of the route is associated with a second communication network, the Internet Protocol (IP) address is used by the communication controller to cause the communication to be established to the second participant device through a gateway to the second communication network.

28. A system for routing a communication between a first participant device associated with a first participant, and a second participant device associated with a second participant, the system comprising:
means for receiving a second participant identifier associated with the second participant device, in response to initiation of the communication by the first participant device;
means for causing a user profile to be accessed in at least one memory, the user profile being specific to the first participant and associated with a plurality of first participant attributes;
at least one processor for comparing at least a portion of the second participant identifier with at least one of the plurality of first participant attributes associated with the user profile of the first participant, to produce a second participant device identifier or identify a username associated with the second participant;
means for identifying at least one route to the second participant device, based on the second participant device identifier or username, whereby the communication may be routed to the second participant device on a first communication network or a second communication network, the means for identifying at least one route to the second participant device comprising at least one system subscriber database for identifying subscribers and at least one route database for providing route information comprising at least one of an Internet protocol (IP) address or domain name associated with the at least one route to the second participant device; and at least one server causing a message comprising the route information to be produced, the route information identifying the at least one route on the first communication network, associated with the second participant device, when the at least one route is associated with a subscriber of the system, the message comprising the route information causing the communication to be carried to the second participant device using the first communication network; and the at least one server causing a message comprising the route information to be produced identifying the at least one route to a gateway to the second communication network, when the at least one route is associated with a non-subscriber of the system, the message comprising the route information causing the communication to be carried to the second participant device using the gateway to the second communication network.

29. An apparatus for routing communications in a packet switched communication system between a first participant device associated with a first participant and a second participant device associated with a second participant, the apparatus comprising:

at least one controller comprising at least one processor in communication with at least one memory storing processor readable instructions, the at least one processor being operably configured by the processor readable instructions to:

in response to initiation of a communication to the second participant device, receive a second participant identifier;

access at least one first participant profile in the at least one memory to locate at least one first participant attribute associated with the first participant;

compare at least a portion of the second participant identifier with the at least one first participant attribute to identify a second participant device identifier associated with at least one route whereby the communication may be routed to the second participant device; and cause a message to be produced comprising route information, based on the second participant device identifier, said route information identifying an Internet Protocol (IP) address associated with the at least a portion of the route to cause the communication to be established to the second participant device;

when the at least a portion of the route is associated with a first communication network, causing the Internet Protocol (IP) address to identify a network element on the first communication network to establish the communication to the second participant device; and when the at least a portion of the route is associated with a second communication network, causing the Internet Protocol (IP) address to identify a gateway to the second communication network to establish the communication to the second participant device.

30. The apparatus of claim 29 wherein:

the first communication network is an Internet protocol (IP) network; and the second communication network is a Public Switched Telephone Network (PSTN), and the at least one processor executes instructions to cause a database of records to be searched to locate a Direct-Inward-Dial (DID) record associating a public telephone number with said second participant device, wherein:

if said DID record is found, causing the Internet Protocol (IP) address to identify the network element on the first communication network to carry the communication to the second participant device using the first communication network; and if said DID record is not found, causing the Internet Protocol (IP) address to identify the gateway to the second communication network to carry the communication to the second participant device using the second communication network.

31. The apparatus of claim 30, wherein the at least one processor is configured to:

access at least one database to locate communication blocking information associated with the second participant; and block the communication when the communication blocking information associated with the second participant identifies the first participant.

32. The apparatus of claim 30, wherein the at least one processor is configured to identify forwarding information associated with the communication, the forwarding information identifying a plurality of destination communication devices.

33. The apparatus of claim 30 wherein the at least one processor is configured to:

(a) identify a plurality of Internet Protocol (IP) addresses for routing the communication to the second participant device; and (b) causing the communication to be received at one of the plurality of Internet Protocol (IP) addresses for routing the communication.

34. The apparatus of claim 29, wherein the at least one processor is further operably configured to:

(a) in response to initiation of a further communication to a third participant device, receive a third participant identifier associated with the third participant device;

(b) process an attribute associated with the first participant profile to determine whether the further communication is allowed to proceed;

(c) if the further communication is not allowed to proceed, cause the further communication not to be established to the third participant device;

(d) if the further communication is allowed to proceed, causing a database of subscribers to be searched to identify a subscriber device identifier, wherein if an entry associated with the subscriber device identifier is found in the database of subscribers, causing the Internet Protocol (IP) address to identify a network element on the first communication network, and if an entry associated with the subscriber device identifier is not found, causing the Internet Protocol (IP) address to identify the gateway to the second communication network.

35. The apparatus of claim 34 wherein the at least one processor is further operably configured to:

cause a query to be sent to a plurality of gateways to determine whether at least one gateway from the plurality of gateways is available to carry the further communication to the third participant device.

36. The apparatus of claim 34 wherein the at least one processor is further operably configured to:

cause the further communication to be routed to a server operable to store the further communication to facilitate delivery of the communication to the third participant device at a later time.

37. The apparatus of claim 29 wherein the at least one processor is operably configured by the processor readable instructions to: cause at least one database to be searched to locate information associating a public telephone number of the second participant device with an identifier of a network element with which the second participant device is currently associated, and causing the communication to be routed to the second participant device based on the identifier of the network element with which the second participant device is currently associated.

38. The apparatus of claim 37 wherein the at least one database comprises a Direct-Inward-Dial (DID) database associating the public telephone number of the second participant device with an identifier of the network element, wherein the network element facilitates routing of the communication to the second participant device.

39. The apparatus of claim 29 wherein the at least one processor is operably configured by the processor readable instructions to: cause at least one database to be searched to locate information associating a public telephone number of the second participant device with a user profile of the second participant that identifies a network element with which the second participant device is currently associated, and causing the communication to be routed to the second participant device based on the identifier of the network element with which the second participant device is currently associated.

40. The apparatus of claim 39 wherein the at least one database comprises a Direct-Inward-Dial (DID) database associating the public telephone number of the second participant device with an identifier of the network element, wherein the network element facilitates routing of the communication to the second participant device.

* * * * *